(12) United States Patent
Jiang et al.

(10) Patent No.: US 11,883,679 B2
(45) Date of Patent: Jan. 30, 2024

(54) SYSTEMS AND METHODS FOR ULTRASOUND INDUCED THROMBOLYSIS WITH MAGNETIC MICROBUBBLES, OPTIONAL NANODROPLETS, AND A ROTATIONAL MAGNETIC FIELD

(71) Applicant: North Carolina State University, Raleigh, NC (US)

(72) Inventors: Xiaoning Jiang, Raleigh, NC (US); Bohua Zhang, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 410 days.

(21) Appl. No.: 17/068,343

(22) Filed: Oct. 12, 2020

(65) Prior Publication Data

US 2021/0106841 A1 Apr. 15, 2021

Related U.S. Application Data

(60) Provisional application No. 62/913,944, filed on Oct. 11, 2019.

(51) Int. Cl.
| | | |
|---|---|---|
| *A61N 2/00* | (2006.01) | |
| *A61N 7/00* | (2006.01) | |
| *A61N 2/12* | (2006.01) | |
| *A61K 41/00* | (2020.01) | |
| *A61P 7/02* | (2006.01) | |

(Continued)

(52) U.S. Cl.
CPC ............ *A61N 2/004* (2013.01); *A61K 9/5094* (2013.01); *A61K 41/0028* (2013.01); *A61N 2/002* (2013.01); *A61N 2/12* (2013.01); *A61N 7/00* (2013.01); *A61P 7/02* (2018.01); *B06B 1/0611* (2013.01); *A61N 2007/0004* (2013.01); (Continued)

(58) Field of Classification Search
CPC .......... A61N 7/00; A61N 2/004; A61N 2/002; A61N 2/12; A61N 2007/0004; A61N 2007/0039; A61N 2007/0078; A61P 7/02; A61K 9/5094; A61K 41/0028; B06B 1/0611; B06B 2201/76
See application file for complete search history.

(56) References Cited

U.S. PATENT DOCUMENTS

| | | | |
|---|---|---|---|
| 8,308,628 B2 | 11/2012 | Creighton | |
| 2005/0100930 A1* | 5/2005 | Wang | B82Y 15/00 436/526 |

(Continued)

OTHER PUBLICATIONS

Molina, Carlos A., et al. "Transcranial ultrasound in clinical sonothrombolysis (TUCSON) trial." Annals of Neurology: Official Journal of the American Neurological Association and the Child Neurology Society 66.1 (2009): 28-38.

(Continued)

*Primary Examiner* — Samuel G Gilbert
(74) *Attorney, Agent, or Firm* — Thomas | Horstemeyer, LLP

(57) ABSTRACT

The disclosure provides systems for ultrasound-induced thrombolysis with magnetic microbubbles under a rotational/alternating magnetic field, sonothrombolysis systems with magnetic microbubbles and optional nanodroplets for inducing thrombolysis under an acoustic field, and a rotational/alternating magnetic field, and methods of treating patients with blood clots using the sonothrombolysis systems of the present disclosure.

24 Claims, 18 Drawing Sheets

(51) Int. Cl.
 B06B 1/06 (2006.01)
 A61K 9/50 (2006.01)
(52) U.S. Cl.
 CPC .............. *A61N 2007/0039* (2013.01); *A61N 2007/0078* (2013.01); *B06B 2201/76* (2013.01)

(56) References Cited

U.S. PATENT DOCUMENTS

| | | | | |
|---|---|---|---|---|
| 2011/0172486 | A1* | 7/2011 | Pankhurst | A61K 49/223 73/24.01 |
| 2015/0045724 | A1* | 2/2015 | Chen | A61K 41/0047 604/22 |
| 2015/0272601 | A1* | 10/2015 | Dixon | A61N 7/00 604/24 |
| 2016/0346809 | A1* | 12/2016 | Zhang | B06B 1/0648 |
| 2018/0344872 | A1* | 12/2018 | Callan | A61K 47/545 |
| 2020/0360711 | A1* | 11/2020 | Kidd | A61N 2/002 |

OTHER PUBLICATIONS

Goel, Leela; et al. "Advances in Sonothrombolysis Techniques Using Piezoelectric Transducers." Sensors 20.5 (2020): 1288.
Sirsi, S. R.; et al. "Microbubble compositions, properties and biomedical applications." Bubble Science, Engineering & Technology 1.1-2 (2009): 3-17.
Sheeran, Paul S., et al. "Design of ultrasonically-activatable nanoparticles using low boiling point perfluorocarbons." Biomaterials 33.11 (2012): 3262-3269.
Martz, Thomas D., et al. "Microfluidic generation of acoustically active nanodroplets." Small 8.12 (2012): 1876-1879.
Paproski, Robert J., et al. "Porphyrin nanodroplets: Sub-micrometer ultrasound and photoacoustic contrast imaging agents." Small 12.3 (2016): 371-380.
Xu, Yurui, et al. "Nanosized Phase-Changeable "Sonocyte" for Promoting Ultrasound Assessment." Small 16.34 (2020): 2002950.
Moyer, Linsey C., et al. "High-intensity focused ultrasound ablation enhancement in vivo via phase-shift nanodroplets compared to microbubbles." Journal of therapeutic ultrasound 3.1 (2015): 7.
Guo, Shifang, et al. "Reduced clot debris size in sonothrombolysis assisted with phase-change nanodroplets." Ultrasonics sonochemistry 54 (2019): 183-191.
Ni, Zhenyi, et al. "Plasmonic silicon quantum dots enabled high-sensitivity ultrabroadband photodetection of graphene-based hybrid phototransistors." ACS nano 11.10 (2017): 9854-9862.
Ma, Ling, et al. "Deep Penetration of Targeted Nanobubbles Enhanced Cavitation Effect on Thrombolytic Capacity." Bioconjugate Chemistry 31.2 (2019): 369-374.
Kim, Jinwook, et al. "A Comparison of Sonothrombolysis in Aged Clots between Low-Boiling-Point Phase-Change Nanodroplets and Microbubbles of the Same Composition." Ultrasound in Medicine & Biology 46.11 (2020): 3059-3068.
Reznik, Nikita, et al. "The efficiency and stability of bubble formation by acoustic vaporization of submicron perfluorocarbon droplets." Ultrasonics 53.7 (2013): 1368-1376.
Kang, Shih-Tsung; et al. "Mechanical bioeffects of acoustic droplet vaporization in vessel-mimicking phantoms." Ultrasonics sonochemistry 21.5 (2014): 1866-1874.
Wang, Siyu, et al. "Targeting and deep-penetrating delivery strategy for stented coronary artery by magnetic guidance and ultrasound stimulation." Ultrasonics Sonochemistry (2020): 105188.
Zhang, Bo, et al. "Ultrasound monitoring of magnet-guided delivery of mesenchymal stem cells labeled with magnetic lipid-polymer hybrid nanobubbles." Biomaterials Science (2020).
Liu, Zhe, et al. "Iron oxide nanoparticle-containing microbubble composites as contrast agents for MR and ultrasound dual-modality imaging." Biomaterials 32.26 (2011): 6155-6163.
Wu, Juefei, et al. "Efficacy of contrast-enhanced US and magnetic microbubbles targeted to vascular cell adhesion molecule-1 for molecular imaging of atherosclerosis." Radiology 260.2 (2011): 463-471.
Cai, Xiaowei; et al. "Applications of magnetic microbubbles for theranostics." Theranostics 2.1 (2012): 103.
De Saint Victor, Marie, et al. "Sonothrombolysis with magnetically targeted microbubbles." Ultrasound in medicine & biology 45.5 (2019): 1151-1163.
Chen, Xiaoqiang, et al. "Magnetic targeting improves the therapeutic efficacy of microbubble-mediated obstructive thrombus sonothrombolysis." Thrombosis and haemostasis 119.11 (2019): 1752-1766.
Wang, Siyu, et al. "Accelerating thrombolysis using a precision and clot-penetrating drug delivery strategy by nanoparticle-shelled microbubbles." Science advances 6.31 (2020): eaaz8204.
Zhang, Bohua; et al. "Ultrasound Thrombolysis with Magnetic Microbubbles Under a Rotational Magnetic Field." 2018 IEEE 13th Nanotechnology Materials and Devices Conference (NMDC). IEEE, 2018.
Zhang, Bohua, et al. "Sonothrombolysis with magnetic microbubbles under a rotational magnetic field." Ultrasonics 98 (2019): 62-71.
Benjamin, Emelia J., et al. "Heart disease and stroke statistics—2018 update: a report from the American Heart Association." Circulation (2018).
Virani, Salim S., et al. "Heart disease and stroke statistics-2020 update: a report from the American Heart Association." Circulation (2020): E139-E596.
Xie, Feng, et al. "Diagnostic ultrasound combined with glycoprotein 2b/3a targeted microbubbles improve microvascular recovery following acute coronary thrombotic occlusions." Circulation 119.10 (2009): 1378.
Zhong, Yixin, et al. "Low-intensity focused ultrasound-responsive phase-transitional nanoparticles for thrombolysis without vascular damage: a synergistic nonpharmaceutical strategy." ACS nano 13.3 (2019): 3387-3403.
Truelsen, Thomas; et al. "The global burden of cerebrovascular disease." Geneva: World Health Organisation (2000) pp. 1-67.
Rha, Joung-Ho; et al. "The impact of recanalization on ischemic stroke outcome: a meta-analysis." Stroke 38.3 (2007): 967-973.
Hacke, Werner, et al. "Thrombolysis with alteplase 3 to 4.5 hours after acute ischemic stroke." New England journal of medicine 359.13 (2008): 1317-1329.
National Institute of Neurological Disorders and Stroke rt-PA Stroke Study Group. "Tissue plasminogen activator for acute ischemic stroke." New England Journal of Medicine 333.24 (1995): 1581-1588.
American College of Emergency Physicians, and American Academy of Neurology. "Clinical Policy: Use of intravenous tPA for the management of acute ischemic stroke in the emergency department." Annals of emergency medicine 61.2 (2013): 225.
Campbell, Bruce CV, et al. "Endovascular therapy for ischemic stroke with perfusion-imaging selection." New England Journal of Medicine 372.11 (2015): 1009-1018.
Ricci, Stefano, et al. "Sonothrombolysis for acute ischaemic stroke." Cochrane database of systematic reviews 6 (2012).
Berkhemer, Olvert A., et al. "A randomized trial of intraarterial treatment for acute ischemic stroke." n Engl J Med 372 (2015): 11-20.
Auboire, Laurent, et al. "Microbubbles combined with ultrasound therapy in ischemic stroke: A systematic review of in-vivo preclinical studies." PloS one 13.2 (2018): e0191788.
Porter, Thomas R., et al. "Thrombolytic enhancement with perfluorocarbon-exposed sonicated dextrose albumin microbubbles." American heart journal 132.5 (1996): 964-968.
Datta, Saurabh, et al. "Ultrasound-enhanced thrombolysis using Definity? as a cavitation nucleation agent." Ultrasound in medicine & biology 34.9 (2008): 1421-1433.
Alonso, Angelika, et al. "Molecular imaging of human thrombus with novel abciximab immunobubbles and ultrasound." Stroke 38.5 (2007): 1508-1514.
Martin, Matthew J., et al. "Enhanced detection of thromboemboli with the use of targeted microbubbles." Stroke 38.10 (2007): 2726-2732.
Schumann, Patricia A., et al. "Targeted-microbubble binding selectively to GPIIb IIIa receptors of platelet thrombi." Investigative radiology 37.11 (2002): 587-593.

(56) References Cited

OTHER PUBLICATIONS

Wang, Xiaowei, et al. "Novel single-chain antibody-targeted microbubbles for molecular ultrasound imaging of thrombosis: validation of a unique noninvasive method for rapid and sensitive detection of thrombi and monitoring of success or failure of thrombolysis in mice." Circulation 125.25 (2012): 3117-3126.
Dayton, Paul, et al. "Acoustic radiation force in vivo: a mechanism to assist targeting of microbubbles." Ultrasound in medicine & biology 25.8 (1999): 1195-1201.
Zhao, Shukui, et al. "Radiation-force assisted targeting facilitates ultrasonic molecular imaging." Molecular imaging 3.3 (2004): 15353500200404115.
Rychak, Joshua J., et al. "Enhanced targeting of ultrasound contrast agents using acoustic radiation force." Ultrasound in medicine & biology 33.7 (2007): 1132-1139.
Chertok, Beata; et al. "Circulating magnetic microbubbles for localized real-time control of drug delivery by ultrasonography-guided magnetic targeting and ultrasound." Theranostics 8.2 (2018): 341.
De Saint Victor, Marie, et al. "Magnetic targeting to enhance microbubble delivery in an occluded microarterial bifurcation." Physics in Medicine & Biology 62.18 (2017): 7451.
Drozdov, Andrey S., et al. "Leach-proof magnetic thrombolytic nanoparticles and coatings of enhanced activity." Scientific reports 6 (2016): 28119.
Gao, Yu, et al. "Controlled nanoparticle release from stable magnetic microbubble oscillations." NPG Asia Materials 8.4 (2016): e260-e260.
Mannell, Hanna, et al. "Site directed vascular gene delivery in vivo by ultrasonic destruction of magnetic nanoparticle coated microbubbles." Nanomedicine: Nanotechnology, Biology and Medicine 8.8 (2012): 1309-1318.
Torno, Michael D., et al. "Improvement of in vitro thrombolysis employing magnetically-guided microspheres." Thrombosis research 121.6 (2008): 799-811.
Bi, Feng, et al. "Chemical conjugation of urokinase to magnetic nanoparticles for targeted thrombolysis." Biomaterials 30.28 (2009): 5125-5130.
Owen, Joshua, et al. "Magnetic targeting of microbubbles against physiologically relevant flow conditions." Interface focus 5.5 (2015): 20150001.
Kim, Jinwook, et al. "Intravascular forward-looking ultrasound transducers for microbubble-mediated sonothrombolysis." Scientific reports 7.1 (2017): 1-10.
Arruebo, Manuel, et al. "Magnetic nanoparticles for drug delivery." Nano today 2.3 (2007): 22-32.
Karlsson, Hanna L., et al. "Size-dependent toxicity of metal oxide particles—a comparison between nano- and micrometer size." Toxicology letters 188.2 (2009): 112-118.
Gupta, Ajay Kumar; et al. "Surface modified superparamagnetic nanoparticles for drug delivery: interaction studies with human fibroblasts in culture." Journal of Materials Science: Materials in Medicine 15.4 (2004): 493-496.
Otsuka, Hidenori; et al. "PEGylated nanoparticles for biological and pharmaceutical applications." Advanced drug delivery reviews 55.3 (2003): 403-419.
Chilkoti, Ashutosh; et al. "Design of thermally responsive, recombinant polypeptide carriers for targeted drug delivery." Advanced drug delivery reviews 54.8 (2002): 1093-1111.

Yang, Fang, et al. "Superparamagnetic iron oxide nanoparticle-embedded encapsulated microbubbles as dual contrast agents of magnetic resonance and ultrasound imaging." Biomaterials 30.23-24 (2009): 3882-3890.
Vlaskou, Dialechti, et al. "Magnetic and acoustically active lipospheres for magnetically targeted nucleic acid delivery." Advanced Functional Materials 20.22 (2010): 3881-3894.
Chen, Cherry C.; et al. "The role of poly (ethylene glycol) brush architecture in complement activation on targeted microbubble surfaces." Biomaterials 32.27 (2011): 6579-6587.
Barrefelt, Åsa, et al. "Biodistribution, kinetics, and biological fate of SPION microbubbles in the rat." International Journal of Nanomedicine 8 (2013): 3241.
Karlsson, Hanna L., et al. "Copper oxide nanoparticles are highly toxic: a comparison between metal oxide nanoparticles and carbon nanotubes." Chemical research in toxicology 21.9 (2008): 1726-1732.
Ankamwar, Balaprasad, et al. "Biocompatibility of Fe3O4 nanoparticles evaluated by in vitro cytotoxicity assays using normal, glia and breast cancer cells." Nanotechnology 21.7 (2010): 075102.
Anzai, Yoshimi, et al. "Evaluation of neck and body metastases to nodes with ferumoxtran 10-enhanced MR imaging: phase III safety and efficacy study." Radiology 228.3 (2003): 777-788.
Weissleder, Ret al., et al. "Superparamagnetic iron oxide: pharmacokinetics and toxicity." American Journal of Roentgenology 152.1 (1989): 167-173.
Owens, Charles A. "Ultrasound-enhanced thrombolysis: EKOS EndoWave infusion catheter system." Seminars in Interventional radiology. vol. 25. No. 1. Thieme Medical Publishers, 2008.
Kucher, Nils, et al. "Randomized, controlled trial of ultrasound-assisted catheter-directed thrombolysis for acute intermediate-risk pulmonary embolism." Circulation 129.4 (2014): 479-486.
Rapoport, Natalya. "Phase-shift, stimuli-responsive perfluorocarbon nanodroplets for drug delivery to cancer." Wiley Interdisciplinary Reviews: Nanomedicine and Nanobiotechnology 4.5 (2012): 492-510.
Duan, Lei, et al. "A multi-gradient targeting drug delivery system based on RGD-I-TRAIL-labeled magnetic microbubbles for cancer theranostics." Advanced Functional Materials 26.45 (2016): 8313-8324.
Barnsley, Lester C., et al. "A Combined Magnetic-Acoustic Device for Simultaneous, Coaligned Application of Magnetic and Ultrasonic Fields." Advanced materials technologies 3.7 (2018): 1800081.
Nordström, M., et al. "A prospective study of the incidence of deep-vein thrombosis within a defined urban population." Journal of internal medicine 232.2 (1992): 155-160.
Bulger, Christopher M; et al. "Epidemiology of acute deep vein thrombosis." Techniques in vascular and interventional radiology 7.2 (2004): 50-54.
Longstaff, Colin; et al. "Basic mechanisms and regulation of fibrinolysis." Journal of Thrombosis and Haemostasis 13 (2015): S98-S105.
Miller, Daniel J.; et al. "Safety of thrombolysis in acute ischemic stroke: a review of complications, risk factors, and newer technologies." The Neurohospitalist 1.3 (2011): 138-147.
Devries, James T., et al. "Catheter-based therapy for acute ischemic stroke: A national unmet need." Catheterization and Cardiovascular Interventions 72.5 (2008): 705-709.

\* cited by examiner

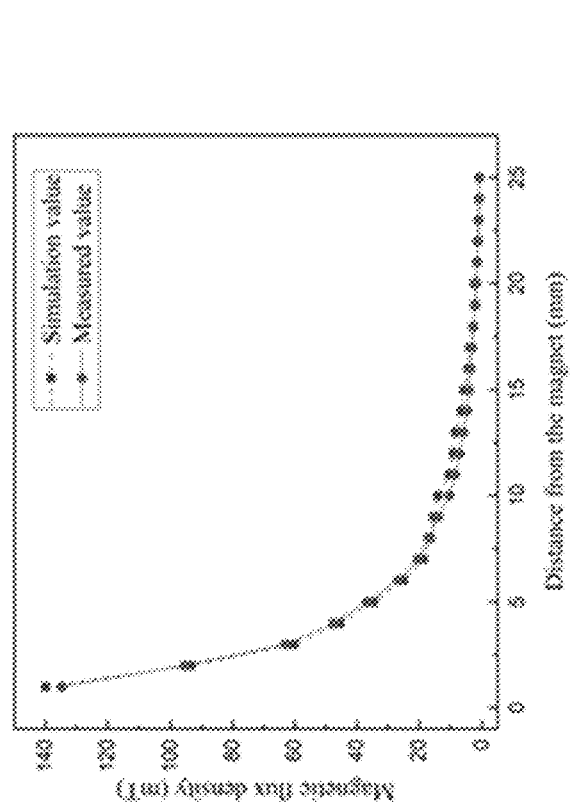
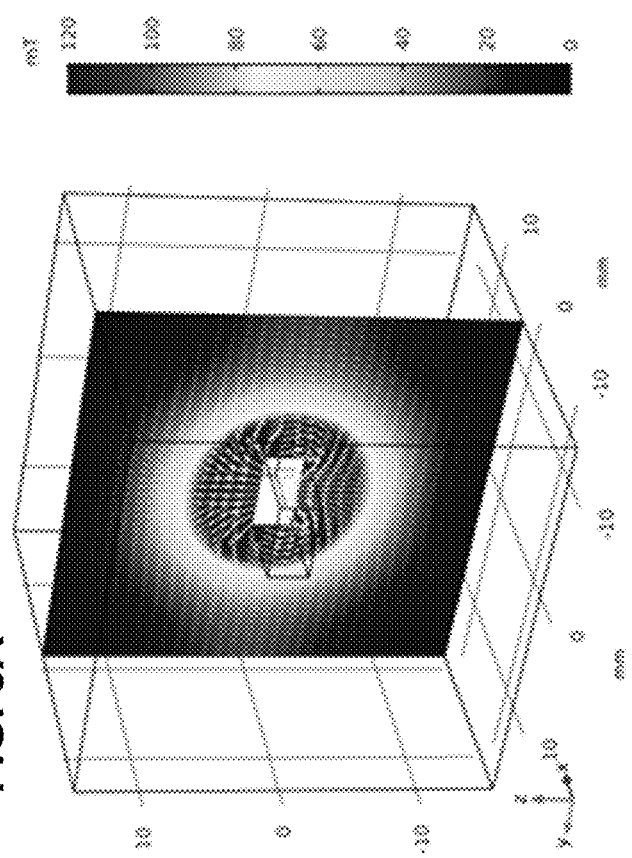
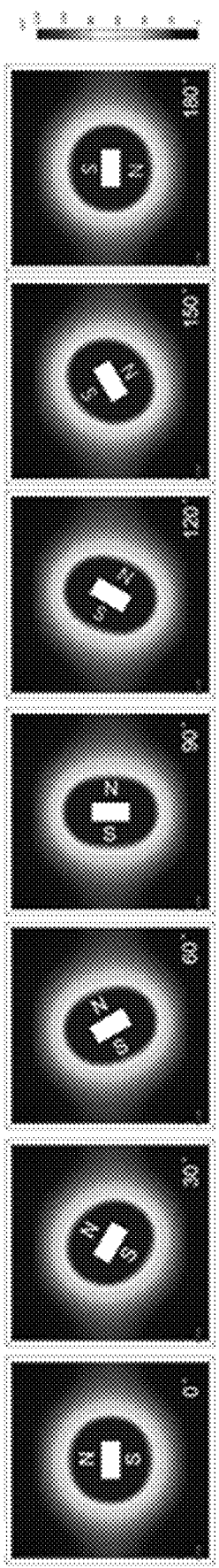
FIG. 3A
FIG. 3B
FIG. 3C

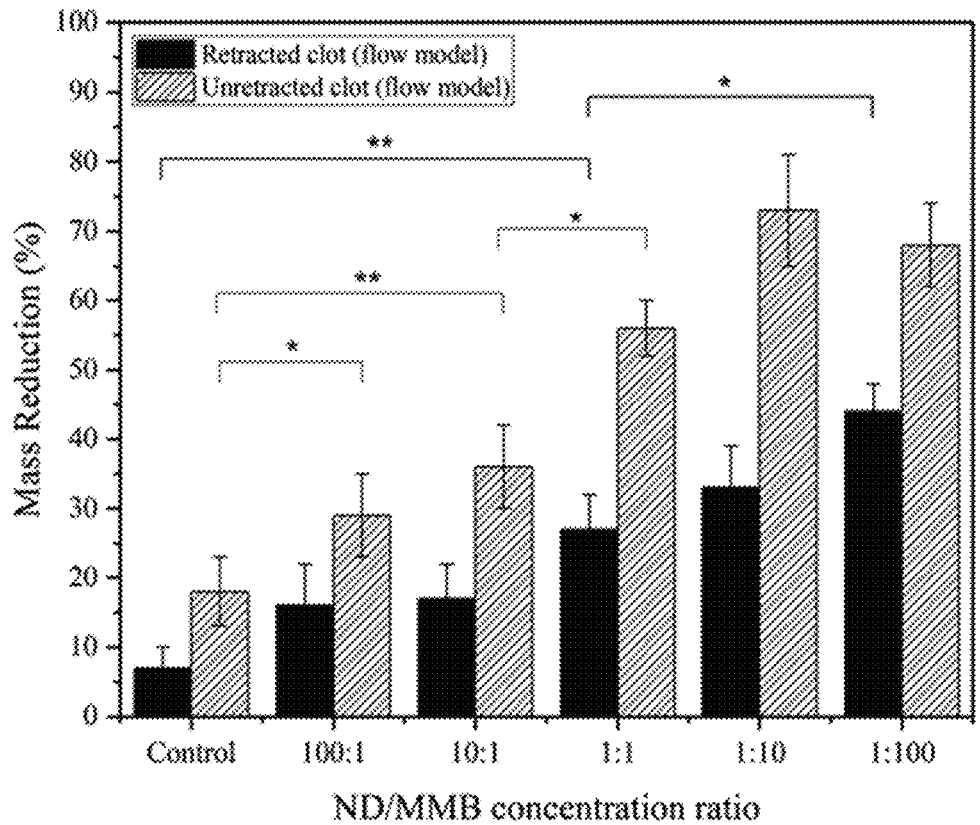
FIG. 21
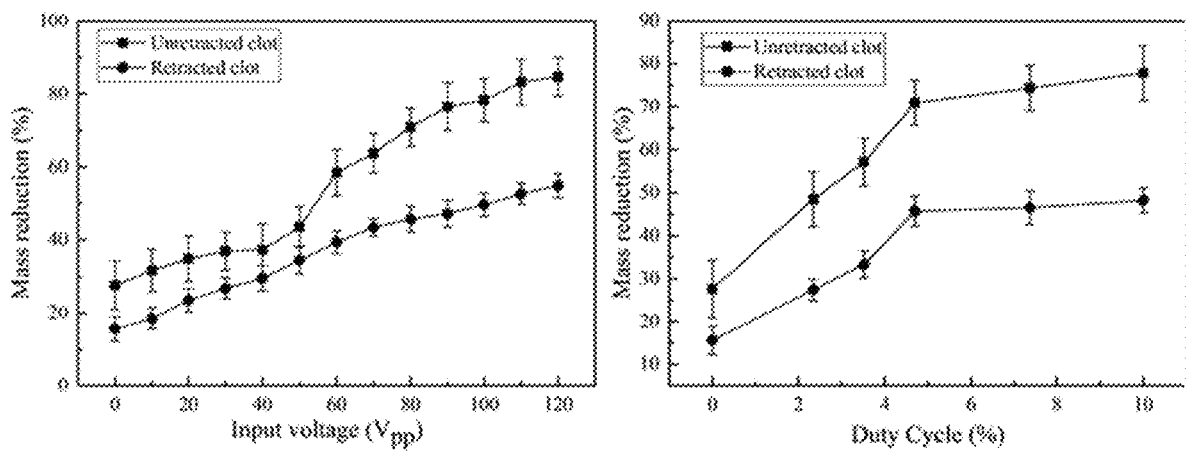
FIG. 22A          FIG. 22B

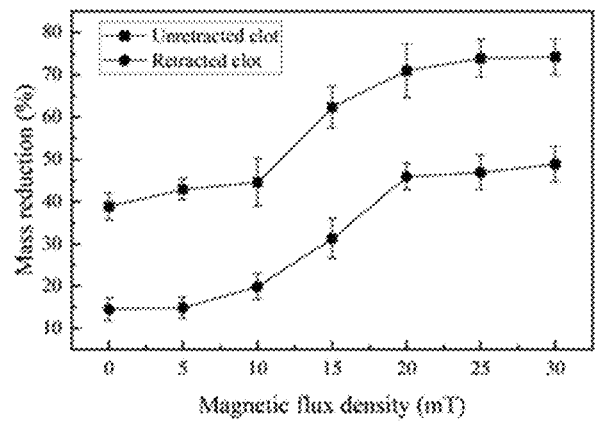
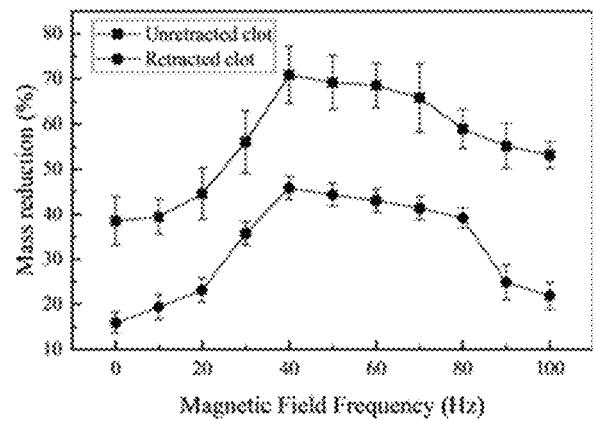
FIG. 23A    FIG. 23B
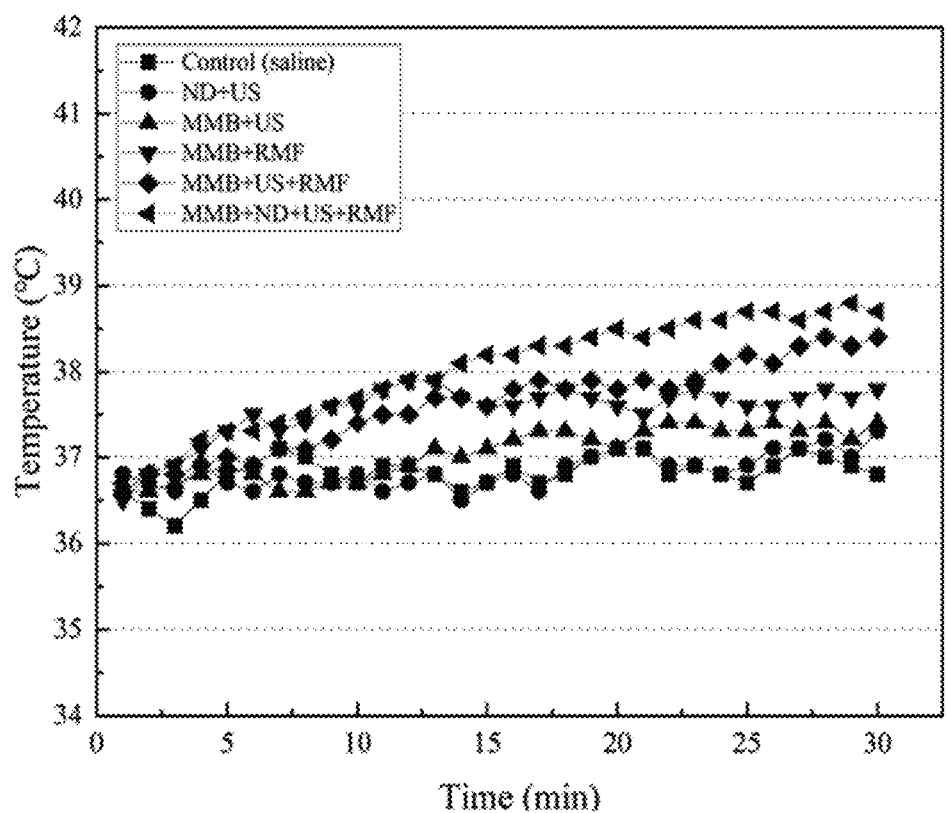
FIG. 24

SYSTEMS AND METHODS FOR ULTRASOUND INDUCED THROMBOLYSIS WITH MAGNETIC MICROBUBBLES, OPTIONAL NANODROPLETS, AND A ROTATIONAL MAGNETIC FIELD

CROSS-REFERENCE TO RELATED APPLICATIONS

This application claims the benefit of and priority to U.S. Provisional Patent Application No. 62/913,944, filed on Oct. 11, 2019, entitled "SYSTEMS AND METHODS FOR ULTRASOUND INDUCED THROMBOLYSIS WITH MAGNETIC MICROBUBBLES AND A ROTATIONAL MAGNETIC FIELD," the contents of which is incorporated by reference herein in its entirety.

STATEMENT REGARDING FEDERALLY SPONSORED RESEARCH OR DEVELOPMENT

This invention was made with government support under grant number HL141967 awarded by the National Institutes of Health. The government has certain rights in the invention.

BACKGROUND

Stroke represents a significant cause of death worldwide. Thrombosis is a severe clinical condition in which a blood clot forms in a blood vessel, blocking blood flow through the cardiovascular system, which can lead to stroke, myocardial infarction, pulmonary embolism, and other potentially fatal conditions. Thrombolysis refers to a treatment to dissolve blood clots in vessels. A currently FDA approved thrombolytic agent for the treatment of blood clots that can cause stroke is recombinant tissue-type plasminogen (rt-PA). However, rt-PA based treatment may trigger off-target effects such as the increased risk of intracranial hemorrhage (ICH). Patients who are ineligible for rt-PA are usually treated with thrombectomy, which is currently only performed at comprehensive stroke centers and limited to a large diameter artery. Alternative or combined therapies include ultrasound thrombolysis methods using microbubbles, but such methods have typically had a relatively low lysis efficiency due to the low microbubble concentration at the clot region due to reduced blood flow in the vessel. The field needs new approaches to treating blood clots.

SUMMARY

In various aspects described herein, sonothrombolysis systems, kits, and methods of making and using the sonothrombolysis systems and treating a blood clot are provided.

In some aspects described herein, the present disclosure provides systems including a plurality of magnetic microbubbles (MMBs) having a gas core and a layer of superparamagnetic nanoparticles around the gas core, an ultrasound transducer effective to induce cavitation of the MMBs, and a rotational magnetic field generator effective to accumulate MMBs in a target region and increase cavitation of the MMBs induced by the ultrasound transducer. In embodiments, the system is a sonothrombolysis system and the ultrasound transducer and the rotational magnetic field generator are adapted for placement near a target clot region of a patient. In embodiments, such systems can further include a catheter configured for in vivo intravascular delivery of the MMBs to the target clot region of the patient. In these systems, the rotational magnetic field generator is configured to be effective to accumulate the MMBs in the target clot region and increase cavitation of the MMBs induced by the ultrasound transducer, such that cavitating MMBs are effective to induce partial or complete thrombolysis of a blood clot in the target clot region. According to some aspects of the present disclosure, systems can further include nanodroplets (NDs) that can also be induced to movement (e.g., cavitation) by the ultrasound transducer.

According to embodiments of the present disclosure for treating blood clots, the methods can include administering MMBs intravascularly to a patient in need of treatment for a blood clot in a blood vessel, where the MMBs have a gas core and a layer of superparamagnetic nanoparticles around the gas core. The methods further include localizing the MMBs to a target clot region in the blood vessel by application of a magnetic field and generating a rotational magnetic field in the target clot region to retain the MMBs in the target clot region and enhance ultrasound-induced movement of the MMBs. The methods further include using an ultrasound transducer to acoustically activate the MMBs to generate movement of the MMBs within the blood vessel in the target clot region, where movement of the MMBs induced by the ultrasound is increased under the rotational magnetic field, such that the movement of the MMBs is effective to reduce the size of the blood clot. Embodiments of the methods can also include administration of NDs to the subject/patient within the blood vessel in the target clot region.

The present disclosure also provides kits for treatment of a subject for conditions such as, but not limited to, a blood clot. Embodiments of a kit of the present disclosure can include an ultrasound transducer effective to induce in vivo cavitation of a plurality of MMBs and optional NDs in a target region of a subject, a portable, targeted rotational magnetic field generator effective to accumulate MMBs in a target region and increase cavitation of the MMBs and optional NDs induced by the ultrasound transducer, and instructions for using the ultrasound transducer and portable, targeted rotational magnetic field generator with a composition of MMBs and optional NDs to treat a subject.

Other systems, methods, features, and advantages of the coating compositions, coated articles, and methods of making thereof will be apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIGS. 3A-3C illustrate a simulation of the magnetic field created by a permanent magnet bar in the YZ plane. The magnetic flux density of the permanent magnet (arrows represent the direction of magnetic flux) is illustrated in FIG. 3A, and the graph in FIG. 3B shows a plot of the simulated and measured values of the rotational magnetic flux density of the magnet used for generating a rotational magnetic field at different distances. FIG. 3C is a series of panels illustrating the change in the magnetic flux density as the magnet rotates 180 degrees.

FIG. 10A illustrates MMBs injected through the catheter and trapped near the clot region under the rotational magnetic field. FIG. 10B illustrates the approach of sonothrombolysis with magnetic microbubbles under a rotational magnetic field. The MMBs can penetrate the clot surface and bind to the fibrin network of the clot under ultrasound exposure. When the rotational magnetic field is then activated, the MMBs start to rotate and vibrate, and the resulting shear force can cause mechanical injury to the fibrin network. Then the MMBs can be activated by the ultrasound exposure and induce the cavitation effects, leading to the disruption of the clot.

FIG. 13A shows the 3D schematic view of a flow model in the center of the Helmholtz coil, FIG. 13B is a 3D view of the magnetic flux density of the Helmholtz coil in XY plane, and FIG. 13C is a series of panels illustrating the magnetic flux density of the rotational magnetic field generated by the Helmholtz coil with a sine-wave input voltage signal (gray horizontal arrow represents the direction of the magnetic flux density norm, and the vertical arrows represent the current direction in the coils).

FIG. 21 is a graph illustrating in vitro test results using ND+MMB+US+RMF treatment method with different NDs/MMBs concentration ratio for retracted and unretracted clot in a flow model. (NDs concentration: $10^8$/mL, MMBs concentration varies from $10^6$/mL to $10^{10}$/mL, Treatment time:

30 min, ultrasound parameters: 80 $V_{pp}$ input voltage, 4.7% duty cycle, f=850 kHz, magnetic field: B=20 mT, f=40 Hz) (*P<0.05, **P<0.01).

FIGS. 22A-22B are graphs illustrating in vitro test results using ND+MMB+US+RMF treatment method with different ultrasound input (A) input voltage, (B) duty cycle (Treatment time: 30 min, ultrasound parameters: f=850 kHz, magnetic field: B=20 mT, f=40 Hz).

FIG. 23A-23B are graphs illustrating in vitro test results using the ND+MMB+US+RMF treatment method with different magnetic field (A) flux density, (B) frequency (Treatment time: 30 min, ultrasound parameters: 80 $V_{pp}$ input voltage, 4.7% duty cycle).

FIG. 24 is a graph illustrating measured temperature changes of the clot region with different treatment methods. Treatment time: 30 min, ultrasound parameters: 80 $V_{pp}$ input voltage, 4.7% duty cycle, f=850 kHz, magnetic field: B=20 mT, f=40 Hz.

Figure 25A:
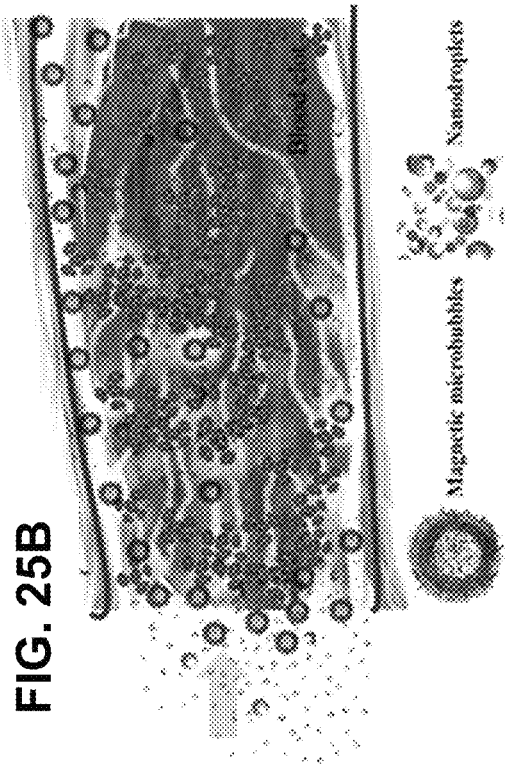
Figure 25B:
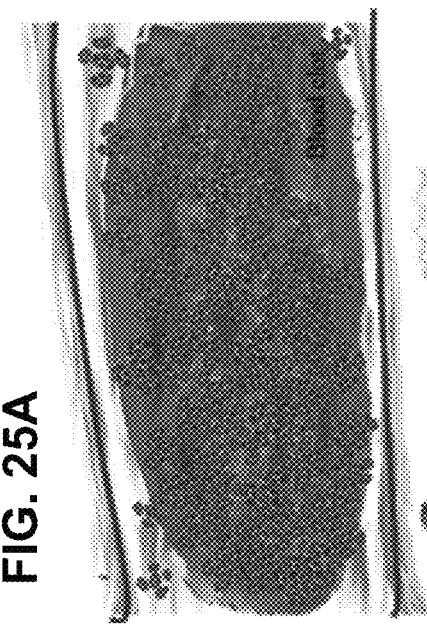
Figure 25C:
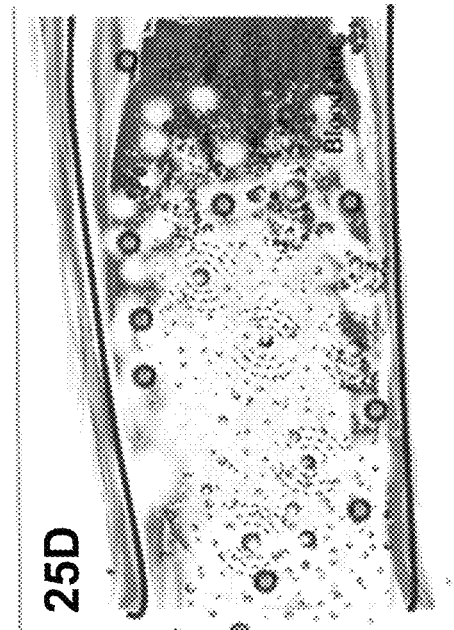
Figure 25D:
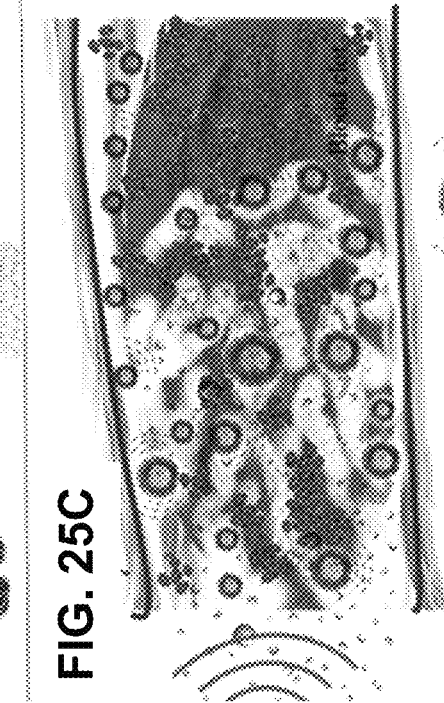

FIGS. 25A-25D are schematic illustrations of sonothrombolysis with NDs and MMBs under a rotational magnetic field. FIG. 25A illustrates a blood clot with red blood cells and fibrin network. FIG. 25B shows MMBs and NDs injected through the catheter, and MMBs were trapped near the clot region under the rotational magnetic field. FIG. 25C illustrates that the MMBs were rotating and cavitating under the rotational magnetic field and ultrasound wave to generate microstreaming for clot lysis. FIG. 25D illustrates the NDs penetrating the clot fibrin network and cavitating under ultrasound waves to induce further clot lysis.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to a tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, nanotechnology, biochemistry, biology, medicine, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, the temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

All publications and patents cited in this specification are cited to disclose and describe the methods and/or materials in connection with which the publications are cited. Publications and patents incorporated by reference, where noted, are incorporated by reference as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. Any terms not specifically defined within the instant application, including terms of art, are interpreted as would be understood by one of ordinary skill in the relevant art; thus, is not intended for any such terms to be defined by a lexicographical definition in any cited art, whether or not incorporated by reference herein, including but not limited to, published patents and patent applications. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

It must be noted that, as used in the specification and the appended claims, the singular forms "a," "an," and "the" include plural referents unless the context clearly dictates otherwise. Thus, for example, the reference to "a cell" includes a plurality of cells. In this specification and in the claims that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components, or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed As used herein, the term "magnetic microbubble" (MMB) indicates micro-sized particles "bubbles" having a gas core, a layer of magnetic nanoparticles located generally around the core, and a surface coating or shell made of materials to hold the microbubble together and/or decrease toxicity, increase biocompatibility, etc. Surface coatings of the MMBs can include materials, such as, but not limited to, oil, polymers, surfactants, lipids, or combinations of one or more of these.

The term "nanodroplets" (also abbreviated herein as NDs), as used herein, indicates nano-sized droplets of materials, generally having both a liquid core and an outers shell. The liquid core can be made of materials, such as, but not limited to decafluorobutane (DFB) ($C_4F_{10}$), perfluorohexane (PFH) ($C_6F_{14}$), octafluoropropane (OFP) ($C_3F_8$), perfluoropentane (PFP) ($C_5F_{12}$), mesoporous silica nanoparticles (MSNs) and magnetic nanodroplets (MNDs). The outer shell can include materials, such as, but not limited to, oil, polymers, surfactants, lipids, albumin, fluorosurfactant (Zonyl FSO), MSPC, DSPC, DPPC, DSPG, DSPE-PEG-2000, DSPE-PEG-5000, cholesterol, and 1,2-distearoyl-sn-glycero-3-phosphocholine.

As used herein, the term "target clot region" indicates an area in a vessel near the location of a blood clot that is blocking or partially blocking fluid flow through the vessel.

The term "biocompatible", as used herein, refers to a material that along with any metabolites or degradation products thereof that are generally non-toxic to the recipient and do not cause any significant adverse effects to the recipient. Generally speaking, biocompatible materials are materials that do not elicit a significant inflammatory or immune response when administered to a patient.

The term "nanoparticle" as used herein includes a nanoscale deposit of homogenous or heterogeneous material. Nanoparticles may be regular or irregular in shape and may be formed from a plurality of co-deposited particles that form a composite nanoscale particle. Nanoparticles may be generally spherical in shape or have a composite shape formed from a plurality of co-deposited generally spherical particles. Exemplary shapes for the nanoparticles include, but are not limited to, spherical, rod, elliptical, cylindrical, disc, and the like. In some embodiments, the nanoparticles have a substantially spherical shape.

As used interchangeably herein, "subject," "individual," or "patient" can refer to a vertebrate organism, such as a mammal (e.g., human). "Subject" can also refer to a cell, a population of cells, a tissue, an organ, or an organism, preferably to human and constituents thereof.

As used herein, the terms "optional" or "optionally" means that the subsequently described event or circumstance can or cannot occur, and that the description includes instances where said event or circumstance occurs and instances where it does not.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "synergistic effect," "synergism," or "synergy" can refer to an effect arising between two or more molecules, compounds, substances, factors, or compositions that that is greater than or different from the sum of their individual effects.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can generally refer to obtaining a desired pharmacological and/or physiological effect. The effect can be, but does not necessarily have to be, prophylactic in terms of preventing or partially preventing a disease, symptom or condition thereof, such as blood clots, stroke, and the like. The effect can be therapeutic in terms of a partial or complete cure of a disease, condition, symptom or adverse effect attributed to the disease, disorder, or condition. The term "treatment" as used herein covers any treatment of blood clots, in a subject, particularly a human, and can include any one or more of the following: (a) preventing the condition from occurring in a subject which may be predisposed to the condition but has not yet been diagnosed as having it; (b) inhibiting the condition, i.e., arresting its development; and (c) relieving the condition, i.e., mitigating or ameliorating the disease/condition and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

Discussion

In accordance with the purpose(s) of the present disclosure, as embodied and broadly described herein, embodiments of the present disclosure, in some aspects, relate to systems and methods for ultrasound-induced thrombolysis with magnetic microbubbles under a rotational magnetic field. Embodiments include sonothrombolysis systems adapted for in vivo thrombolysis of a clot in a patient and methods of using the systems to treat a clot in a patient. Embodiments also include systems and methods for ultrasound-induced thrombolysis with magnetic microbubbles and nanodroplets under a rotational magnetic field.

Thrombosis is an extremely critical clinical condition where a clot forms inside a blood vessel which blocks the blood flow through the cardiovascular system. Sonothrombolysis (STL), a technique involving the use of microbubbles (MBs) combined with ultrasound (US) to enhance clot dissolution, is under therapeutic assessment as a method for recanalization of occluded blood vessels. Over the past twenty years, case-control studies and clinical trials have demonstrated the relative safety and efficacy of sonothrombolysis with microbubbles as a thrombolytic treatment in ischemic stroke, as compared to conventional rt-PA based therapy [8, 9]. However, certain limitations of this technology have prevented its widespread acceptance.

A recent study showed that acoustic waves with a frequency range from sub-MHz to 1 MHz and intensities below the threshold of inertial cavitation facilitate stable cavitation of microbubbles [10]. On the other hand, an earlier study showed that higher microbubble concentration could lead to greater clot disruption because of the higher number of microbubbles cavitating in response to US pressures [11]. Thus, to promote and sustain the nucleation of cavitation during US treatment process, a higher dose ($>1.2\times10^{10}$ MBs/mL) of MBs is recommended for better thrombolytic treatment [12].

However, the presently available microbubble-mediated thrombolysis systems and methods lack mechanisms for preferential accumulation of higher concentration of microbubbles in the targeted clot region. The low concentration of microbubbles in the area due to the reduced blood flow will potentially decrease the thrombolysis rate. Magnetic microbubbles (MMBs) are microbubbles coated with superparamagnetic iron oxide nanoparticles that not only maintain the acoustic properties of MBs but also possess the sensitivity to magnetic fields [12-24]. The dual-modality functionality makes MMBs useful for potential applications such as targeted drug delivery [25] and precise-t-PA delivery in drug-mediated thrombolysis [27, 27]. These methods used static magnetic fields to locate the magnetic microbubble to release the t-PA drug.

The present disclosure describes the first systems and methods to utilize magnetic microbubbles for ultrasound thrombolysis under a rotational magnetic field (RMF). The Examples below demonstrate that magnetic microbubble can be a useful adjuvant to the current microbubble-mediated sonothrombolysis treatment. As described in greater detail in the examples below, it appears that, by oscillating magnetic microbubbles in the rotational magnetic field, a vortex-like microstreaming in clot region enhances microbubble cavitation under sonication. The present disclosure provides systems and methods including low-dose intravenous injection of MMBs, which then systemically circulate but are subsequently magnetically concentrated at the clot region. In addition, systems and methods of the present disclosure utilize both alternating magnetic force and sonication to penetrate and dissolve the thrombus. In methods and systems of the present disclosure, MMBs are trapped and shaken by external rotational magnetic field within the ultrasound beam and near the target clot. The MMB's act as nuclei for cavitation and the pressure threshold is reduced, thereby resulting in improved lytic rate with lower ultrasound exposure. Example 1 below demonstrates the use of a rotational magnetic field to entrap and oscillate the MMBs with intravascular forward-looking ultrasound transducers for sonothrombolysis in vitro. Additional sonothrombolysis systems and methods were also developed and tested according to the present disclosure that further includes nanodroplets (NDs) in combination with MMBs under a rotational magnetic field and activated with an ultrasound transducer, which further enhanced the thrombolytic efficiency of the approach, as described in greater detail in Example 2, below.

MMB+US+RMF and MMB+ND+US+RMF Sonothrombolysis Systems

Figure 1A:
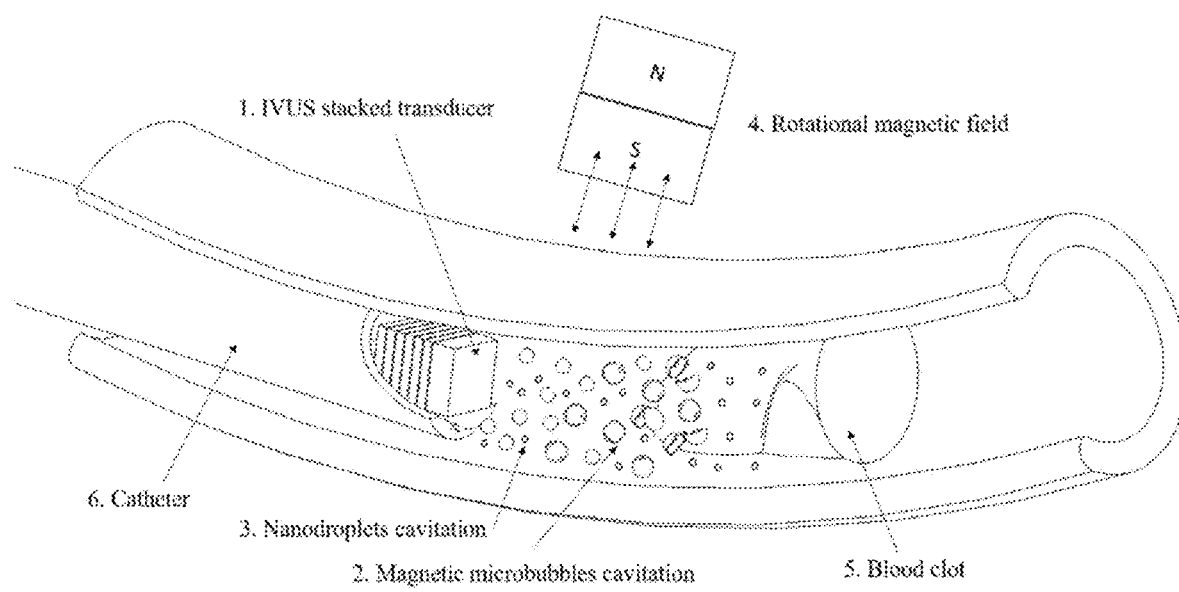
FIGS. 1A-1B illustrate schematics of embodiments of a magnetic microbubble thrombolysis system of the present disclosure with an IVUS stacked transducer (FIG. 1A) or a HIFU transducer (FIG. 1B).
Figure 1B:
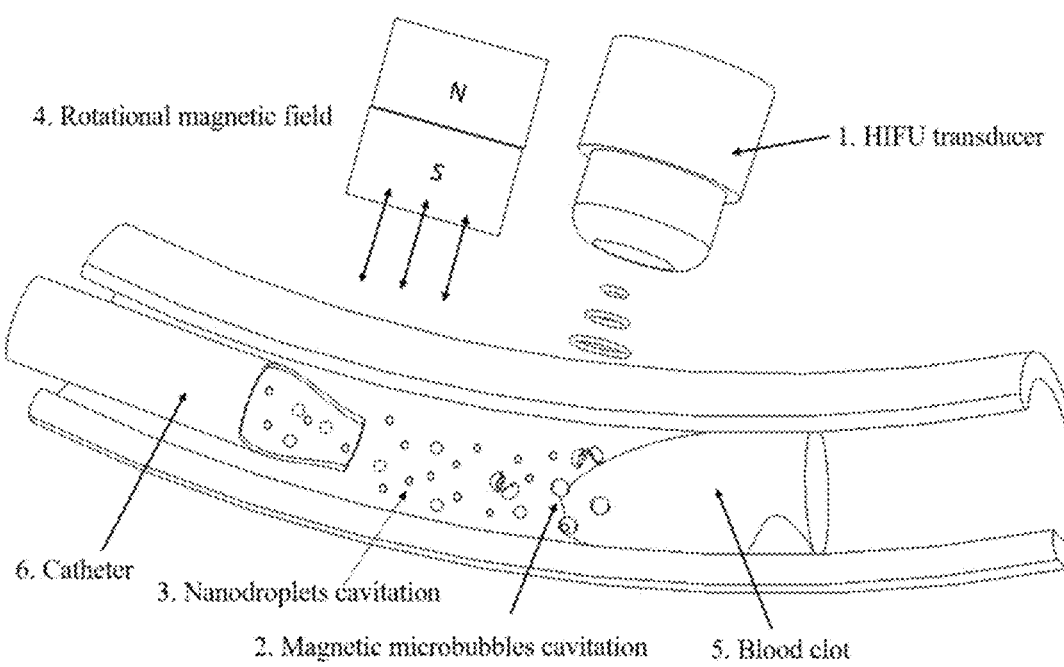

Briefly described and as generally illustrated in FIGS. 1A-1B, sonothrombolysis systems of the present disclosure include an ultrasound transducer (1), a plurality of magnetic microbubbles (MMBs) (2), an optional plurality of nanodroplets (NDs) (3), and a rotational magnetic field generator (4) in the vicinity of a vascular blood clot (5) (e.g., a "target clot region"). Embodiments of sonothrombolysis systems of the present disclosure also include a catheter (6) for intravascular delivery of the magnetic microbubbles.

According to some aspects of the present disclosure, the system includes a plurality of MMBs (2), an ultrasound transducer (1), and a rotational magnetic field generator (4) (such systems may also be referred to in the examples below as MMB+US+RMF). The MMBs have a gas core and a magnetic responsiveness agent and can be delivered to a target region. The ultrasound transducer is effective to induce cavitation of the MMBs, and the rotational magnetic field generator is effective to accumulate MMBs in a target region as well as to increase cavitation of the MMBs induced by the ultrasound transducer. According to some aspects of the present disclosure, the system also includes a plurality of NDs (3) (such systems may also be referred to in the examples below as MMB+ND+US+RMF). The NDs can also be delivered to the target region (e.g., in combination with the MMBs or simultaneously but via different delivery). In systems that include both the MMBs and the NDs, the ultrasound transducer is effective to induce cavitation of both the MMBs and the NDs at the target region effective to result in at least partial lysis of a clot at the target region.

The MMBs (2) in the systems of the present disclosure have a gas core and plurality of superparamagnetic nanoparticles that generally form a layer around the gas core. The MMBs are, in embodiments, multi-scale composite particles of microbubbles (MBs) and superparamagnetic nanoparticles, such as but not limited to superparamagnetic iron oxide nanoparticles (SPIONs). The superparamagnetic nanoparticles endow the microbubbles with magnetic responsiveness. In embodiments, the MMBs also have an outer surface coating or shell made of materials to hold the microbubble together and/or decrease toxicity, increase biocompatibility, etc. Surface coatings of the MMBs can include film or membrane-forming materials, such as, but not limited to oil, polymers, surfactants, lipids, albumin, fluorosurfactant (Zonyl FSO), MSPC, DSPC, DPPC, DSPG, DSPE-PEG-2000, DSPE-PEG-5000, cholesterol, 1,2-distearoyl-sn-glycero-3-phosphocholine or combinations of one or more of these. According to aspects of the disclosure, the superparamagnetic nanoparticles in the MMBs have an average size of about 10 nm-100 nm. In embodiments, the superparamagnetic nanoparticles are metal oxides, such as, but not including iron oxides. In embodiments, the MMBs are made from magnetic nanoparticles, such as but not limited to $Fe_3O_4$ nanoparticles, and such $Fe_3O_4$ nanoparticles can have a diameter of about 10 nm-100 nm. In embodiments, the MMBs have an average diameter of about 3 μm to 100 μm. In embodiments, the MMBs have an average diameter of about 3-6 μm. In embodiments, the magnetic microbubbles are prepared as described in Gao, et al., NPG Asia Mater. 8 (2016), incorporated herein by reference. In embodiments, magnetic nanoparticles, such as $Fe_3O_4$ nanoparticles are mixed with dodecyl sulfate (SDS) and water to prepare the MMBs.

In embodiments the MMBs are made by combining superparamagnetic nanoparticles (e.g., $Fe_3O_4$ nanoparticles with a diameter of about 10-100 nm) with deionized water to create a stock mixture and dispersing (e.g., with ultrasound) for a time (e.g., about 10-30 min). Then the stock mixture of nanoparticles is combined with a solution of SDS and water, or other appropriate solution, and mixed to form MMBs. The formed MMBs can be washed before use. The resulting MMBs can have an average diameter as described above.

In embodiments the MMBs are included in a fluid composition for delivery. For instance, the MMBs can be combined with one or more pharmaceutically acceptable carriers, such as but not limited to pyrogen-free water, phosphate buffer solutions, ringer's solution, isotonic saline solution, hypotonic saline solution, and the like. In embodiments, the MMBs and/or the compositions can further include thrombolytic drugs, targeting agents, other therapeutic agents, imaging agents, and the like. In embodiments, the MMBs can be used for applications other than sonothrombolysis, such as targeted drug delivery, imaging, cancer tumor ablation, and the like.

According to some aspects of the disclosure, the NDs are nano-sized droplets having a liquid core and an outer coating. In embodiments, the liquid core can be made of one or more materials such as, but not limited to, decafluorobutane (DFB) ($C_4F_{10}$), perfluorohexane (PFH) ($C_6F_{14}$), octafluoropropane (OFP) ($C_3F_8$), perfluoropentane (PFP) ($C_5F_{12}$), mesoporous silica nanoparticles (MSNs) and magnetic nanodroplets (MNDs). In embodiments, the outer shell can include materials or combinations of materials, such as, but not limited to, oil, polymers, surfactants, lipids, albumin, fluorosurfactant (Zonyl FSO), MSPC, DSPC, DPPC, DSPG, DSPE-PEG-2000, DSPE-PEG-5000, cholesterol, and 1,2-distearoyl-sn-glycero-3-phosphocholine. In embodiments, the NDs are made of decafluorobutane (DFB) ($C_4F_{10}$) as the liquid core and DPPC, DPPE-PEG-2000, as the outer shell. The NDs can have a size of about 150 nm-350 nm, and some nanodroplets can have a relatively low vaporing point (<0° C.-37° C.), such as the NDs described in Kim, et al., Ultrasound Med. Biol., 2020, which is hereby incorporated herein by reference.

In some embodiments of the disclosure, DFB nanodroplets can be prepared by forming nanodroplet precursors by mechanical agitation of a mixture of decafluorobutane and dodecafluoropentane (e.g., in a 1:1 ratio). The mixture can then be condensed under pressure and low temperature to form droplets having a diameter of about 150-350 nm (e.g., 240±65 nm diameter). In embodiments, the NDs can be included in a fluid composition for delivery. In embodiments, such fluid ND composition can include a plurality of NDs and one or more pharmaceutically acceptable carriers, such as described above. In embodiments, the MMBs and NDs can be combined in a single composition or can be delivered in separate compositions.

In embodiments of systems of the present disclosure, the ultrasound transducer (1) can be an intravascular ultrasound (IVUS) transducer (FIG. 1A), and in other embodiments, the ultrasound transducer (1) can be an external HIFU transducer (FIG. 1B). In embodiments, such as illustrated in FIG. 1A, the IVUS transducer is a forward-looking stacked IVUS transducer such as described in Kim, et al., Sci. Rep. 7 (2017) 1-10 (incorporated herein by reference), as described in greater detail below. In embodiments the IVUS transducer includes a stacked piezoelectric resonator made of stacked piezoelectric plates (e.g., PZT-5A ceramic plates) with alternating poling directions. In embodiments the transducer includes about 2 to about 20, or more, stacked plates; in embodiments it includes 6-8 stacked plates. In embodiments, the thickness of each layer (e.g., plate) has a thickness from about 100 μm to 0.5 mm; from about 100 μm to 300 μm; from about 0.05 mm to 0.5 mm, and other intermediate ranges. In embodiments the thickness of each layer is about 250 μm. In embodiments, the total thickness of the transcoder is from about 0.6 mm to 1.8 mm; in embodiments from about 1 mm to 5 mm; and in embodiments it is about 1.6 mm. In embodiments, the lateral dimensions of the transducer are optimized for intravascular dimensions (e.g., from about 1 mm to 3 mm, from about 1 mm to 1.5 mm, or such as about 1.2 mm) and to generate a pure longitudinal vibration mode.

In embodiments, the ultrasound (US) transducer generates an acoustic frequency of about 100 kHz to about 5 MHz, such as about 300 kHz to 900 kHz. In some embodiments, the ultrasound transducer is configured to have an ultrasound duty cycle of about 0.5% to about 25%, such as about 4% to 12%. According to aspects of the disclosure, the ultrasound transducer has an input voltage of about 10 $V_{pp}$ to 250 $V_{pp}$, such as about 25 $V_{pp}$ to 125 $V_{pp}$, In embodiments the US is integrated into a catheter for simplified intravascular delivery and use, such as the ultrasound transducer catheter and array described in international patent application WO 2018/014021 A2 (corresponding to U.S. application Ser. No. 16/317,983), which are hereby incorporated herein by reference. In embodiments, the transducer the system can further include a catheter configured for in vivo intravascular delivery of the MMBs or the MMBs and the NDs to the target clot region of a patient. In embodiments the catheter and IVUS transducer are integrated together, such as described in WO 2018/014021 incorporated above. For instance, in embodiments the catheter can include a conduit for the IVUS transducer as well as a separate drug delivery lumen for delivery of MMBs, NDs, and/or other compositions.

In embodiments, the rotational magnetic field is provided by a rotational magnetic field generator. The rotational magnetic field can be generated by different magnet assemblies, such as an electromagnet with coils, a rotating permanent magnet, and the like. In embodiments, the rotational magnetic field generator includes a cylindrical permanent magnet and a power source to rotate the magnet cylinder. In embodiments, the rotational magnetic field is generated by rotating a permanent magnet cylinder (e.g., a NdFeB permanent magnet cylinder). Rotating permanent magnets provide advantages such as the generation of high magnetic flux density without the need for a large power supply or the need to cool parts (such as coils in some electromagnets). In embodiments, the permanent magnet cylinder is rotated by a power source, such as, but not limited to, a DC motor (e.g., a 12V DC motor). In embodiments, changing the rotational speed of the magnet cylinder generates various frequencies of alternating magnetic fields, such as about 1 to 300 Hz, (e.g., about 1-150 Hz, such as, but not limited to, about 1 Hz to 7 Hz). In embodiments, the rotational magnetic field has a magnetic flux density of about 1 mT to 80 mT, such as, but not limited to about 45 mT. In embodiments, the cylindrical permanent magnet has a diameter of about 5 mm to 20 mm, such as about 12.7 mm. In embodiments, the cylindrical permanent magnet has a length of about 10 mm to 100 mm, such as about 63.5 mm. In embodiments, the rotational magnetic field generators is a portable, targeted device that can be used by a practitioner in a clinical setting. In embodiments, a portable, targeted rotational magnetic field generator can apply a rotational magnetic field to a targeted area of a subject, as opposed to a more general magnetic field, such as with an MRI. In embodiments, such device could be handheld and could be used by a practitioner to target a very specific area, such as occlusion of a blood vessel.

In embodiments of the systems of the present disclosure, the system is a sonothrombolysis system and the ultrasound transducer and the rotational magnetic field generator are adapted for placement near a target clot region of a patient, and the system includes one or more catheters configured for in vivo intravascular delivery of the MMBs, or MMBs+NDs (together or separately) to the target clot region of the patient. In such embodiments, the ultrasound transducer is effective to induce cavitation (and possibly microstreaming) of the MMBs, as well as any NDs. The rotational magnetic field generator is effective to accumulate the MMBs in the target clot region and increase cavitation of the MMBs induced by the ultrasound transducer, such that cavitating MMBs (alone or in combination with NDs) are effective to induce partial or complete thrombolysis of a blood clot in the target clot region. The combined ultrasound frequency and the rotational magnetic field is effective to induce cavitation of the MMBs that is greater than that induced by US alone. In embodiments, the combined US and RMF induces increased cavitation and microstreaming of the MMBs, such that the combined US and RMF produces a synergistic effect with respect to the anti-thrombolytic effect of the MMBs. In embodiments, the combined activity of the MMBs and NDs is greater than the anti-thrombolytic effects of the MMBs alone. In some aspects, the combined activity of the MMBs and NDs may interact such that microstreaming of the MMBs allows greater penetration of NDs into a clot, the cavitation of which creates more clot lysis and more room for greater penetration of MMBs, resulting in a synergistic effect. Additional aspects will be described in greater detail in reference to the sonothrombolysis methods of the disclosure and in the examples below.

In addition to the systems described above, the present disclosure also provides devices and kits including the ultrasound transducers and rotational magnetic field generators of the present disclosure for use in conjunction with MMBs, and optionally NDs, for treatment of a subject, such as for Sonothrombolysis of a blood clot. In embodiments, a kit of the present disclosure can include an ultrasound transducer, as described above, effective to induce in vivo cavitation of a plurality of magnetic microbubbles (MMBs) and optional nanodroplets (NDs) in a target region of a subject and a portable, targeted rotational magnetic field generator, as described above, effective to accumulate MMBs in a target region and increase cavitation of the MMBs and optional NDs induced by the ultrasound transducer. In embodiments, such kits include the device(s) described here along with instructions for using the ultrasound transducer and portable, targeted rotational magnetic field generator with a composition of MMBs and optional NDs to treat a subject, such as described in the methods below. In embodiments of kits of the present disclosure, the ultrasound transducer is an intravascular ultrasound (IVUS) transducer that is integrated into a catheter, and in embodiments, the catheter also includes an integrated delivery lumen for administration of a composition comprising MMBs to the target region of the subject. In some embodiments, the instructions describe the use of the IVUS transducer, the portable, targeted rotational magnetic field generator and a composition of MMBs and optional NDs for intravascular sonothrombolysis of a blood clot in a subject, such as described above, and in the methods and examples below.

MMB+US+RMF and MMB+ND+US+RMF Sonothrombolysis Methods

The present disclosure also provides methods of treating blood clots with the MMB or MMB+ND sonothrombolysis systems of the present disclosure under a rotational magnetic field. Methods of the present disclosure, in embodiments, include providing MMBs to a patient in need of treatment for a blood clot, localizing the MMBs to the vicinity of the clot (a "target clot region") by application of a magnetic field, optionally also administering a plurality of NDs to the patient (mixed with, concurrently with, or subsequently to the administration of the MMBs), generating a rotational magnetic field in the vicinity of the clot to retain the MMBs in the target clot region while inducing vibrational movement of the MMBs, and using an ultrasound transducer to acoustically activate the MMBs and optional NDs. The acoustic activation of the MMBs and optional NDs induces movement of the particles, such as, but not limited to cavitation/oscillation of the MMBs, microstreaming of the MMBs, cavitation/oscillation of the NDs, microstreaming of the NDs, and combinations of these. The oscillation/cavitation/microstreaming of the MMBs, and optional NDs, under the rotational magnetic field is effective to break up at least a portion of the blood clot, resulting in a reduction in size or elimination of the blood clot (e.g., thrombolysis).

In embodiments, acoustic activation of the MMBs under the rotational magnetic field increases the lysis rate as compared to non-magnetic microbubbles activated via an ultrasound transducer alone. It is believed that oscillating the MMBs with the ultrasound transducer while under a rotational magnetic field in the target clot region creates a vortex-like microstreaming in the target clot region, enhances microbubble cavitation, and increases thrombolysis rate. In embodiments where NDs are also co-administered to the patient with the MMBs, it is believed that the combined oscillation of the MMBs and NDs and microstreaming of the NDs as a combined and/or synergistic effect where the oscillations of both types of particles enhance the penetration of the other particles resulting in increased thrombolysis as compared to MMBs or NDs alone under US and/or RMF induced activity.

In embodiments, the MMBs and optional NDs are administered to a subject intravascularly, e.g., via injection, catheter, etc. In embodiments, the ultrasound transducer is an internal transducer that is placed intravascularly in the patient in the vicinity of the clot. In embodiments both the transducer and the MMB/ND composition are introduced via a catheter to an affected blood vessel of a patient. In embodiments, a catheter is configured to accommodate the US transducer as well as administer a composition of MMBs/NDs. For instance, as described in greater detail below, a catheter may include two conduits, the first conduit with an internal diameter sufficient to accommodate an intravascular US transducer and another integrated lumen through which a composition of MMBs/NDs (or two separate compositions) can be administered. Additional embodiments and details of such configurations are described below.

In embodiments, the magnetic frequency of the rotational magnetic field is from about 1 Hz to 300 Hz, or more, such as from about 1 Hz to 100 Hz, or about 40 Hz. In the Examples below, it was found that higher frequencies can increase the oscillation magnitude of the MMBs, resulting in greater activation by ultrasound, greater cavitation effect and microstreaming. In embodiments the magnetic flux density is from about 1 mT to 80 mT, such as from about 2 mT to 45 mT.

In embodiments of the methods of the present disclosure, the ultrasound produces an acoustic frequency of about 100 kHz to about 5 MHz (or greater), such as from about 300 kHz to 900 kHz. In embodiments, the ultrasound frequency is about 600 kHz to 850 kHz. In embodiments, the ultrasound duty cycle can be from about 0.5% to about 25%. In embodiments a duty cycle of about 5% or more is used (e.g., about 6.45%, about 10%, etc.). In other embodiments, the duty cycle is about 4-5%, such as about 4.7%. In embodiments, the input voltage for the ultrasound is about 10 $V_{pp}$ or more, e.g., about 10-250 $V_{pp}$. In embodiments, the input voltage is from about 26 $V_{pp}$ to 120 $V_{pp}$. The Examples below demonstrate that increased duty cycle and input voltage increase percent mass loss of a blood clot. Additionally, treatment time affects thrombolytic outcome, with increased treatment times increasing percent mass loss. Treatment time can be from about 5 min to about 90 min (such as about 15 min, about 30 min, about 45 min, about 60 min, etc.). Treatment times, ultrasound input voltage, ultrasound duty cycle, magnetic flux density, and magnetic frequency can be varied and optimized for specific treatment plans.

In embodiments, acoustic activation of the MMBs under the rotational magnetic field increases a lysis rate of the blood clot as compared to acoustic activation of non-magnetic MBs with an ultrasound transducer alone. Also, as discussed above and explained in the examples below, in some embodiments, the acoustic activation of the MMBs and the NDs with the addition of the RMF further increases a lysis rate of the blood clot as compared to just MMBs with US and RMF without NDs. This is believed to be the result of a combined and/or synergistic effect of the cavitation and/or microstreaming of both the MMBs and the NDs that increase the thrombolytic effect of each other.

As described in Example 2, below, the concentration of MMBs, NDs and the ratio of NDs to MMBs also affects the lytic efficiency of the system and methods of the present disclosure. In embodiments the MMBs are administered at a concentration of about $10^7$-$10^{12}$ MMBs/mL. In embodiments, the NDs are administered at a concentration of about $10^8$-$10^{12}$ NDs/mL. In embodiments the MMBs and NDs are administered at a concentration ratio of NDs/MMBs of about 1:100 to 100:1, such as about 1:10 to 10:1, or about 1:1.

In embodiments the methods of the present disclosure described above can also be combined with other clot treatment methods, such as traditional drug-mediated thrombolysis through agents such as tPA. In embodiments, tPA can be co-administered with MMBs and/or NDs. In embodiments, MMBs or NDs of the present disclosure can include tPA or other thrombolytic active ingredients within the MMBs or NDs or combined with the MMB/ND composition.

Additional details regarding the methods, compositions, and organisms of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, the temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'."

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1—Sonothrombolysis with Magnetic Microbubbles Under a Rotational Magnetic Field The present example describes an embodiment of a new method using the rotational magnetic field to trap and vibrate magnetic microbubbles at the target clot region and then using an intravascular forward-looking ultrasound transducer to activate them acoustically. In this study, the influence of different blood flow conditions, vessel occlusion conditions (partial and fully occluded), clot ages (fresh, retracted), ultrasound parameters (input voltage, duty cycle), and rotational magnetic field parameters (amplitude, frequency) on the thrombolysis rate was investigated. Results demonstrated that the additional use of magnetic microbubbles significantly enhances in vitro lysis of blood clots.

Over the past twenty years, many case-control studies and clinical trials have demonstrated that sonothrombolysis with microbubbles is a relatively safe and effective thrombolytic treatment in ischemic stroke compared to rt-PA only based therapy [8,9]. Ultrasound thrombolysis with injected microbubble agents may allow a reduced administered rt-PA dose and minimize the side-effects on tissue and blood vessels, enabling the thrombolysis treatment to become more efficient and safer. The current study showed that acoustic waves with frequencies range from sub-MHz to 1 MHz and intensities below the threshold of inertial cavitation are critical to stable cavitation of microbubbles [10]. Furthermore, the previous study showed that a higher microbubble concentration would lead to greater clot disruption because of the higher number of microbubbles cavitating in response to US pressure [11]. Besides, to promote and sustain the nucleation of cavitation during US treatment process, a higher dose ($>1.2 \times 10^{10}$ MBs/mL) of MBs are recommended for better thrombolytic treatment [12].

One of the significant challenges in the process of sonothrombolysis treatment is to control the hydrodynamic conditions in occluded vessels since they mostly limit the number of microbubbles that can be retained and cavitated at the site of a blood clot during ultrasound exposure. The low concentration of microbubbles due to the blood flow will potentially decrease the thrombolysis rate. Therefore, there are emerging studies focusing on the development of microbubble targeting technique which is a promising method that could increase the proximity between microbubble agents and the blood clot surface, thus increasing the thrombolysis rate and reducing the required drug dose. There are biological methods using microbubbles with antibody conjugation on their surface for targeting thrombus treatment, but those methods still rely on the passive blood flow to accumulate the microbubbles to the thrombus surface [13-17]. The acoustic radiation force can also be used to increase the accumulation efficacy of targeted microbubbles since the microbubbles can travel in the direction of sound wave propagation and aggregate at the thrombus surface [18-20]. However, the above methods are mostly dependent on the blood flow conditions and precise alignment of the beam with a target vessel, which may be challenging with complex vessels in vivo treatment.

As an alternative, some investigations in recent years have focused on the development of magnetic microbubbles (MMBs) [21-24]. Magnetic microbubbles are microbubbles coated with superparamagnetic iron oxide nanoparticles that can maintain the acoustic properties of MBs and possess the sensitivity to magnetic fields. The dual-modality functionality makes MMBs useful for a broad range of application such as targeted drug delivery [21,25] and thrombolysis [26,27]. However, there are some challenging problems of using MMBs for targeted thrombolysis such as how to build a controllable magnetic system with enough strength of magnetic field and gradient to counteract blood flow in a blood vessel. Although recent studies showed the lipid-coated microbubbles with iron oxide nanoparticles can be retained with a magnet against clinically relevant flow conditions [28], there is a lack of systematic study of ultrasound thrombolysis using MMBs under magnetic field.

The present disclosure is the first to utilize magnetic microbubbles for ultrasound thrombolysis under a rotational magnetic field (RMF). This approach investigates whether magnetic microbubbles can be a useful adjuvant to the current microbubble-mediated sonothrombolysis treatment. It is believed that by oscillating magnetic microbubbles in the rotational magnetic field, a vortex-like microstreaming in clot region will enhance microbubble cavitation under sonication. This goal of this example was to demonstrate the feasibility of using the rotational magnetic field to entrap and oscillate the MMBs with intravascular forward-looking ultrasound transducers for sonothrombolysis in vitro. First, the influence of blood flow conditions on the different thrombolysis treatment methods (MB+US, MMB+US, MMB+RMF, MMB+US+RMF) was compared. Second, the influence of different clot conditions (partial occlusion, fully occluded) and different clot ages (fresh, retracted) on the thrombolysis efficiency was investigated. Finally, to better understand the mechanism of rotational magnetic field assisted sonothrombolysis, the influence of various ultrasound parameters (input voltage, duty cycle) and magnetic field parameters (amplitude, frequency) on the thrombolysis rate was explored.

Materials and Methods

Transducer Development

This example employs the previous forward-looking stacked ultrasound transducer design [29], and the ultrasound frequency was chosen as 620 kHz. The details of the forward-looking transducer development procedure can be found in our previous work [29, incorporated herein by reference]. Briefly, a stacked piezoelectric transducer which has six layers was fabricated using PZT-5A ceramic thin plates with alternating poling directions. Each PZT-5A layer thickness was 250 µm, and the total thickness of the stacked transducer was 1.6 mm without a matching layer. To bond the layer, a conductive bond (E-solder 302) was used, and the bonding layer thickness was 30 µm. The transducer has a lateral dimension of 1.2 mm and can be mounted on an 8F catheter for the intravascular test.

Blood Clot Preparation

Figure 2:
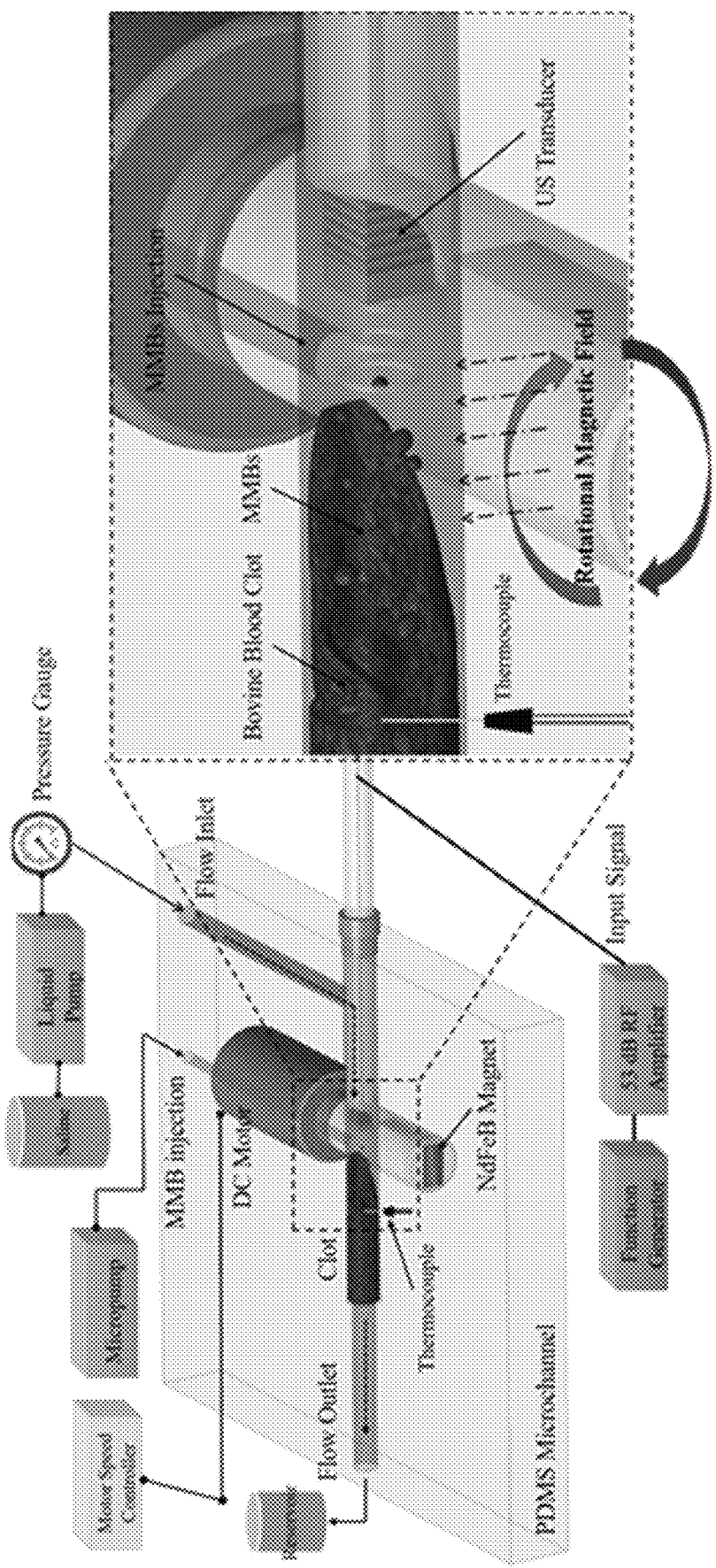
FIG. 2 is a schematic illustration of an embodiment of an in vitro ultrasound thrombolysis system with magnetic microbubbles under a rotational magnetic field according to aspects of the present disclosure.

The blood clots were prepared following a similar procedure used in our previous work [29]. First, the fresh bovine blood obtained from Densco Marketing, Inc. (Woodstock, Ill., USA) was mixed with 2.75% W/V $CaCl_2$ solution (Fisher Scientific, Fair Lawn, NJ) in a volume ratio of 10:1 (50 mL blood/5 mL $CaCl_2$ solution). Second, the mixed blood solution was drained to Tygon tubes (6.35 mm ID, 7.94 mm OD). Then the Tygon tubes were immersed in a 37° C. water bath for 3 h. Finally, the tubes with coagulated blood were stored at low temperature (4° C.) for 1 to 7 days to generate clots with different ages. Clot samples for thrombolysis tests were cut into a cylindrical shape (length: 12±2 mm, diameter 3±0.5 mm) and weighted as 130 mg±10% in mass and then positioned into a customized polydimethylsiloxane (PDMS) blood vessel mimicking phantom (microchannel, ID: 2-3 mm with 33.3% stenosis) as shown in FIG. 2.

Magnetic Microbubble Preparation

The magnetic microbubbles were prepared by a similar procedure as described in reference [24]. First, Magnetic nanoparticles ($Fe_3O_4$, with diameter around 50 nm, Sigma-Aldrich, St Louis, MO, USA) were mixed with deionized water to form a 2 mg/mL stock solution and then treated with ultrasound for 20 min. Second, a solution containing 400 μl of a stock solution of $Fe_3O_4$ nanoparticles, 150 μl of 10 mM sodium dodecyl sulfate (SDS) and 150 μl of deionized water was mixed by shaking for 1 min [24]. Finally, MMBs were left 24 hours before being washed with phosphate-buffered saline (PBS) three times before use. The MMBs had an average diameter of ~6 μm.

The Rotational Magnetic Field Generation

The rotational magnetic field was generated by rotating a NdFeB N50 permanent magnet bar (Size: 12 mm*6 mm*3 mm) which was mounted on a 3D printed fixture with a 12V DC motor (FIG. 2). By changing the rotational speed of the magnet bar, the various frequencies (0-25 Hz) alternating magnetic fields were generated. Compared with electromagnet made of coils, the permanent magnet has many advantages such as high magnetic flux density, no need for large power supply and coils cooling. As shown in FIG. 2, the DC motor was positioned below the PDMS phantom, and the magnetic field was aligned along the vertical direction. The magnetic field was measured by a gaussmeter (Model GM2, AlphaLab, Inc.) and the position of the DC motor was controlled by a 3-axis motion stage so that the amplitude of magnetic field applied to the clot can be adjusted by changing the distance between magnet bar and clot area.

To better understand the physics of the rotational magnet field, the magnetic field generated by the permanent magnet was simulated in the COMSOL® Multiphysics software. The simulated magnetic flux density of the magnet in the YZ plane is shown in FIG. 3A. The white arrow direction represents the direction of the magnetic flux density norm. FIG. 3B showed the relationship between rotational magnetic flux density (B) and the distance (d) from the rotating magnet. The measured results agree well with the simulation ones. FIG. 3C showed the magnetic flux density change when the magnet rotated from 0 degrees to 180 degrees. When the magnet was rotated by a DC motor, the rotational magnetic field could be generated in a pattern as shown in FIG. 3C. The magnetic field generated a torque $\vec{\tau}=\vec{\mu}\times\vec{B}$. This induced the rotation of the magnetic microbubbles around their own axis and the rotation speed can be controlled by changing the rotational magnetic field frequency.

In Vitro Tests Procedure

As shown in FIG. 2, for every treatment test, a 130 mg±10% clot sample was positioned into a 3 mm diameter PDMS microchannel. The PDMS microchannel was filled with saline at a temperature of 37.3±0.3° C. The saline was pumped by a peristaltic liquid pump (INTL-LAB, China) from a saline reservoir into the flow inlet of the PDMS microchannel. The liquid pressure inside the microchannel tube was measured by a low-pressure gauge (200 series, Noshok, Inc) and kept at 3.7 mmHg pressure level by controlling the speed of the pump. The flow outlet of the microchannel tube was connected to a reservoir to collect the liquid and debris after the thrombolysis treatment. A thermocouple probe (OMEGA Engineering, Norwalk, CT) was placed on the PDMS microchannel and the probe tip was positioned at the clot region to measure the temperature change during the treatment. The ultrasound transducer was inserted through the right side of the PDMS microchannel tube, and the transducer position was controlled by a 3-axis motion stage to control the distance between the transducer and the clot (~0.5 mm). The NdFeB magnet mounted on a DC motor was controlled by a motor speed controller and was positioned under the PDMS microchannel to apply the alternating magnetic field to the magnetic microbubbles. The US transducer was driven by a 53 dB RF power amplifier (75A250A, AR, Inc. Souderton, PA) and the input signal was generated by a function generator (33250A, Agilent Technologies, Inc., Loveland, CO). To pump the magnetic microbubbles into the tube, a micropump (DUAL-NE-1010-US, New Era Pump Systems Inc., Farmingdale, NY) was used, and the flow rate was maintained at 100 μL/min. Diluted magnetic microbubbles ($10^9$/mL) with average diameters of ~6 μm were used as the therapeutic agents with the treatment time of 30 min for each test.

To investigate the influence of flow pressure conditions on different thrombolysis treatment, the fully occluded blood clot flow model was used in this test. First, the blood clot was cut into the small size cylindrical shape (length: 12±2 mm, diameter 3±0.5 mm) and weighted as 130 mg±10% in mass and then positioned into a PDMS microchannel as shown in FIG. 2. Then the saline flow was pumped into the microchannel tube. Since the microchannel was fully occluded by the blood clot before the treatment, there will be no flow out from the outlet of the microchannel. The liquid pressure in the fully occluded microchannel was measured and maintained at 3.7 mmHg. Second, the magnetic microbubbles (concentration: $10^9$/mL, average diameter ~6 μm) were injected through a 1 mm PDMS microchannel tube by a micropump. Then the rotational magnetic field (RMF) with magnetic flux density B=50 mT and frequency f=20 Hz generated by rotating a NdFeB magnet was applied to the clot area to activate the magnetic microbubble. Third, the US transducer with input signal as 120 $V_{pp}$ input voltage and 10% duty cycle was position near the clot surface (~0.5 mm) to cavitate the magnetic microbubble for the thrombolysis treatment. To compare the influence of ultrasound and rotational magnetic field on the thrombolysis treatment process, different groups of treatment methods were conducted under the same procedure described above. To be specific, the control group was only injected with magnetic microbubble without any ultrasound and magnetic field exposure. The MB+US group was treated with microbubble (MB concentration: $10^9$/mL, average diameter ~6 μm) and ultrasound. The MB was prepared by a similar process in our previous work [29]. The MMB+US group was treated with magnetic microbubble and ultrasound only. The MMB+RMF group was treated with magnetic microbubble (MMB) and rotational magnetic field (RMF) only. The MMB+US+RMF was treated with magnetic microbubble and both ultrasound and rotational magnetic field. The similar treatments were also repeated without the flow pressure in fully occluded microchannel to compare the results with the presence of flow pressure.

Moreover, to clarify the influence of flow model on the thrombolysis treatment, different clot occlusion conditions were investigated. The clot was cut into different sizes to meet the requirement for different occlusion case (40% partial occlusion, 70% partial occlusion, 100% fully occluded). The similar flow pressure conditions and treatment methods as described above were used in this experiment. To investigate the influence of clot ages on the thrombolysis treatment, different clots with ages from 1 day to 7 days were used in the experiment with similar flow pressure conditions and treatment methods.

Finally, to clarify the thrombolysis effect of ultrasound, rotational magnetic field and magnetic microbubble combined treatment, various treatment cases were considered. The blood clots were exposed to ultrasound with different duty cycle (1.6%, 3.2%, 6.4%, 10%), input voltage (26 $V_{pp}$, 39 $V_{pp}$, 45 $V_{pp}$, 62 $V_{pp}$, 68 $V_{pp}$, 80 $V_{pp}$, 93 $V_{pp}$, 120 $V_{pp}$) and rotational magnetic fields with various magnetic flux density (4 mT, 10 mT, 30 mT, 50 mT, 65 mT, 80 mT), and frequency (static, 1 Hz, 5 Hz, 10 Hz, 15 Hz, 20 Hz, 25 Hz). The results presented in this study were expressed as the mean±SD (n=3). Statistical analysis was conducted using the MATLAB Statistical Toolbox (Mathworks, Natick, MA, USA). The student's t-test was used to estimate the statistical significance of tests with various treatment conditions.

Results and Discussion

Thrombolysis with Different Treatment Methods Under Flow Pressure

Figure 4:
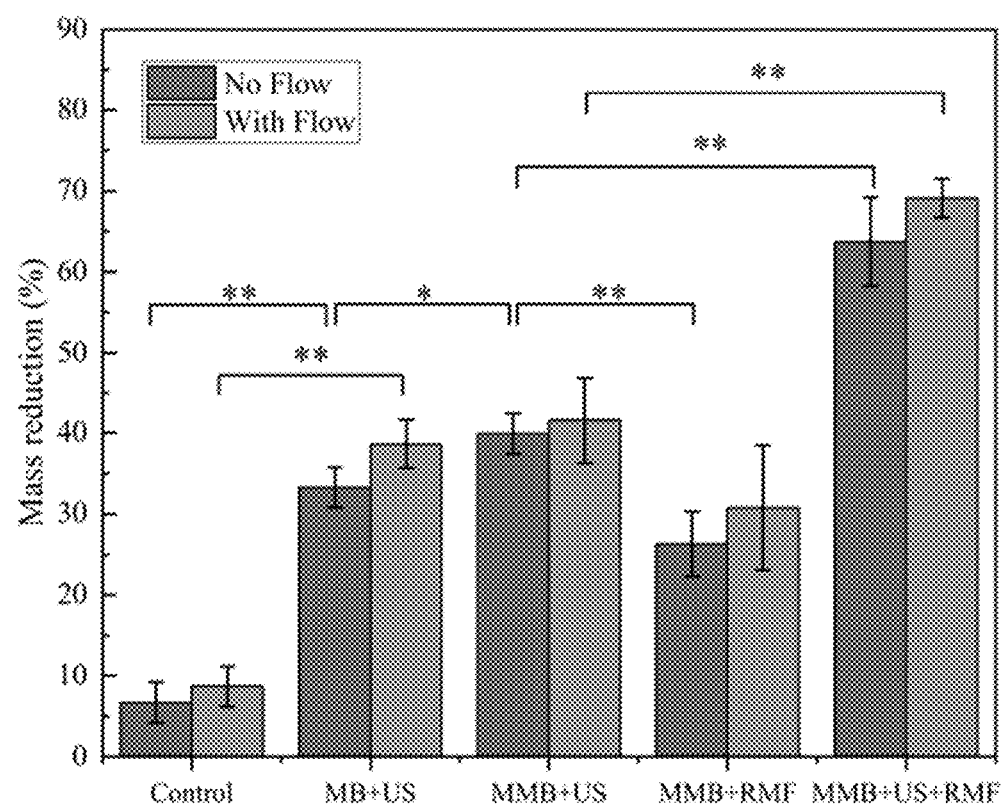
FIG. 4 is a bar graph illustrating in vitro test results using different treatment methods with or without flow pressure. Treatment time was 30 min, ultrasound parameters: 120 $V_{pp}$ input voltage, 10% duty cycle, f=620 kHz, magnetic field: B=50 mT, f=20 Hz (*P<0.05, **P<0.01).

Previously, researchers have shown that the microbubble-mediated ultrasound thrombolysis rate is also affected by blood flow pressure [29]. The flow pressure (3.7 mmHg) in this study is in the range of physiologic flow pressure in the human vein. To investigate the influence of flow pressure conditions on different thrombolysis treatment, the fully occluded blood clot flow model was used in this test. Different groups of methods (MB+US, MMB+US, MMB+RMF, MMB+US+RMF) were used for the thrombolysis treatment with the flow pressure and without the flow pressure. For each treatment, the same treatment parameters were used: 30 min treatment time, ultrasound input parameters (120 $V_{pp}$ input voltage, 10% duty cycle, f=620 kHz) and magnetic field parameters (magnetic field flux density B=50 mT, magnetic field frequency f=20 Hz). As shown in FIG. 4, among all the treatment groups, the clot mass reduction rate is slightly higher with the flow pressure than without flow pressure. This is likely because in the fully occluded flow model, the flow pressure will help the MB/MMB better penetration the clot fibrin network and achieve higher lysis rate.

Moreover, the clot mass reduction rate using magnetic microbubbles treated by the combined method of ultrasound and the rotational magnetic field is much higher than the group that treated with ultrasound only or rotational magnetic field only. The statistics result also shows there is a significant difference (p<0.01) between MMB+US group and MMB+US+RMF group. This indicates that the rotational magnetic fields applied on the magnetic microbubble could enhance the ultrasound thrombolysis treatment.

Figure 5:
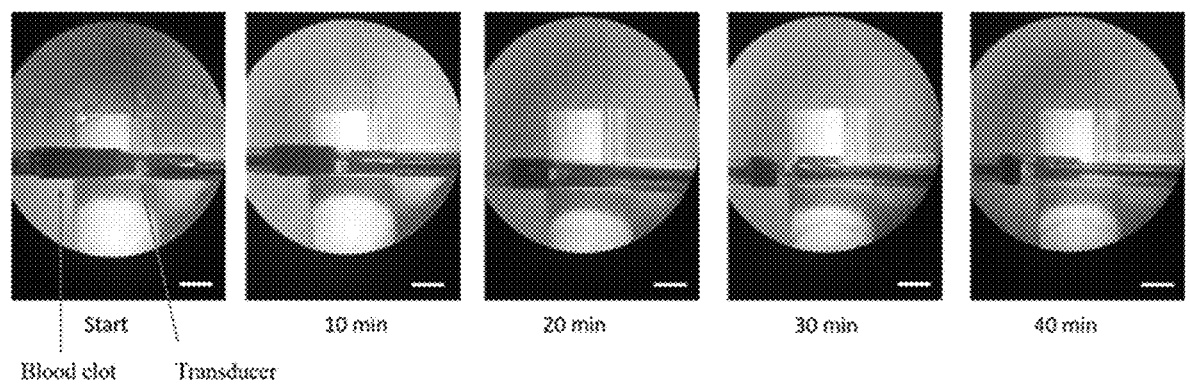
FIG. 5 is a series of images illustrating in vitro clot lysis using a system of the present disclosure with ultrasonic thrombolysis mediated by magnetic microbubbles under a rotational magnetic field. Images were captured under a microscope during 40 min treatment at 10 minute time intervals. Ultrasound parameters: 120 $V_{pp}$ input voltage, 10% duty cycle, f=620 kHz, magnetic field: B=50 mT, f=20 Hz (scale bar=3 mm).

The in vitro clot lysis results using MMB+US+RMF treatment method in a fully occluded blood clot flow model with flow pressure were shown in FIG. 5. The captured images with 10 min-interval show gradual volume reduction of the blood clot. After 40 min treatment time, the target clot size reduced to about 22.2% of its original size (mass reduction from 130 mg to 30 mg) which shows that the MMB+US+RMF combined method can improve the clot lysis rate significantly.

Thrombolysis Treatment with Different Clot Occlusion Case

Figure 6A:
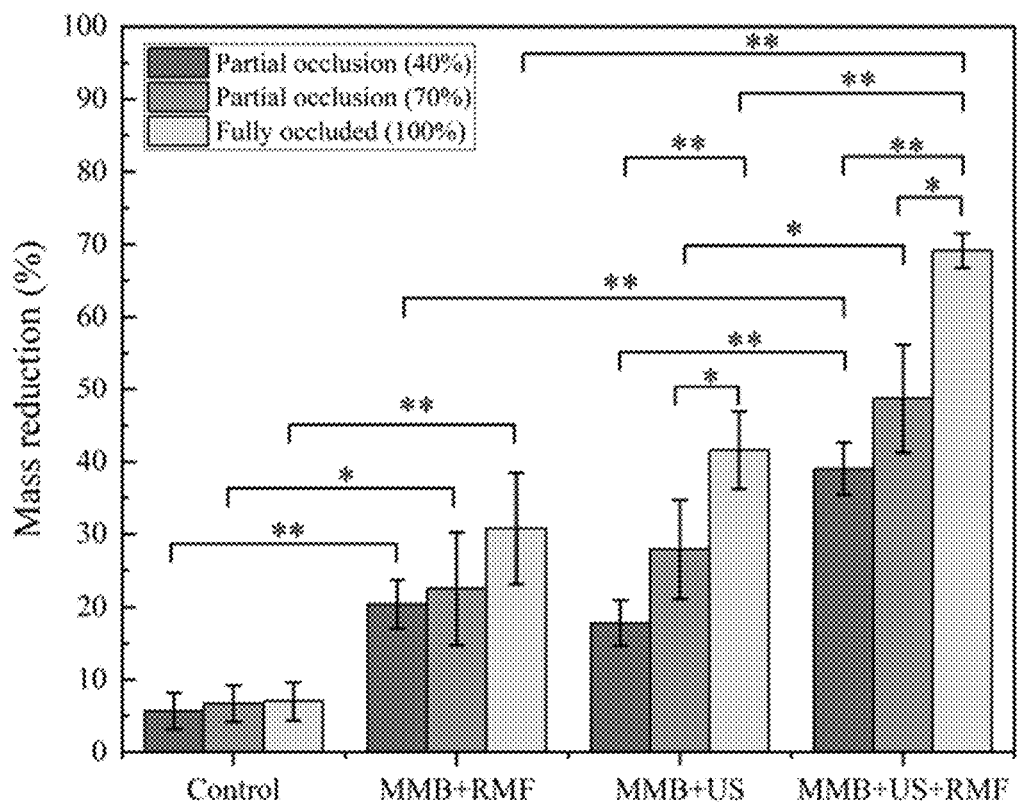
FIG. 6A is a bar graph illustrating in vitro test results using different treatment methods with different vessel occlusions. Treatment time was 30 min, ultrasound parameters: 120 $V_{pp}$ input voltage, 10% duty cycle, f=620 kHz, magnetic field: B=50 mT, f=20 Hz (*P<0.05, **P<0.01).

To clarify the influence of flow model on the thrombolysis treatment, different vessel occlusion conditions were investigated. For each treatment, the same treatment parameters were used: 30 min treatment time, ultrasound input parameters (120 $V_{pp}$ input voltage, 10% duty cycle, f=620 kHz) and magnetic field parameters (magnetic field flux density B=50 mT, magnetic field frequency f=20 Hz). The control group was only injected with magnetic microbubble without any ultrasound and magnetic field exposure. As shown in FIG. 6A, among all the treatment groups, the partial occlusion 40% case has the lowest clot mass reduction compared to the partial occlusion 70% case and fully occluded case. This is likely because the MMBs concentration in the partial occlusion flow model will drop due to the presence of flow. Therefore, the available magnetic microbubbles that retained in the clot surface area for the ultrasound treatment were limited to a low concentration due to the flow which resulted in a low thrombolysis rate. However, the group with combined treatment (MMB+US+RMF) still shows a higher mass reduction rate than the ultrasound only (MMB+US) group. Besides, the statistics result also shows that even in partial occlusion 40% case, there is still a significant difference (p<0.01) in mass reduction rate when using combined treatment (MMB+US+RMF) (39%), compared to ultrasound only (MMB+US) (17.8%).

Temperature Changes and Effects

Figure 6B:
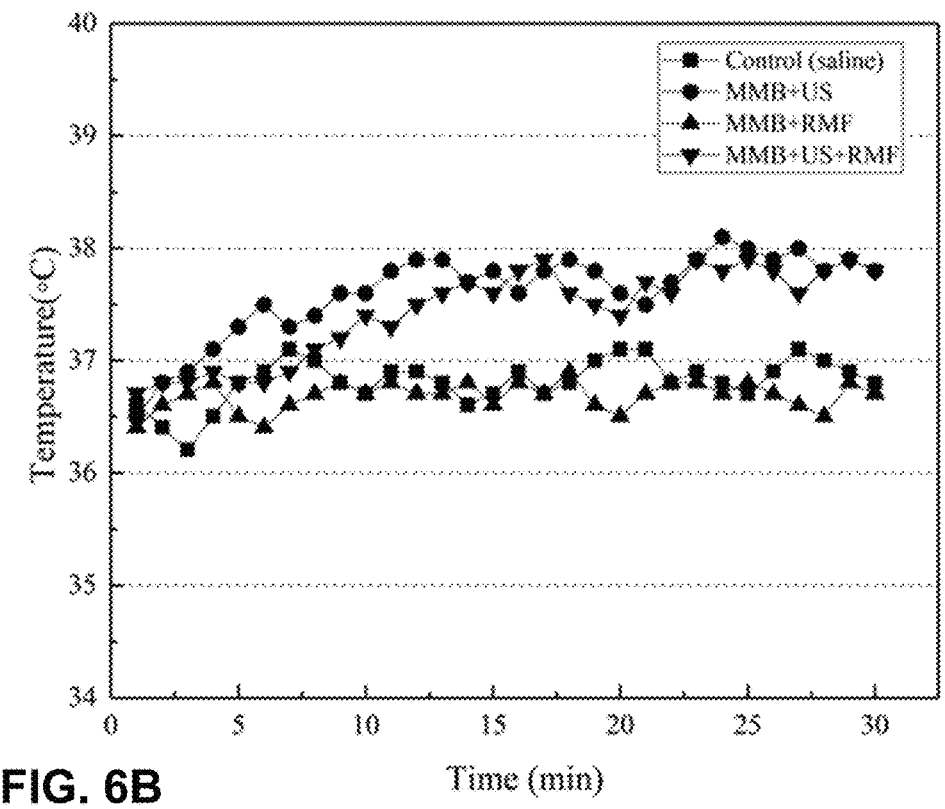
FIG. 6B is a graph illustrating measured temperature changes of the clot region with different treatment methods. Treatment time was 30 min, ultrasound parameters: 120 $V_{pp}$ input voltage, 10% duty cycle, f=620 kHz, magnetic field: B=50 mT, f=20 Hz

To better understand the temperature changes and effects during the thrombolysis treatment, we measured the temperature changes of the clot region using a thermocouple probe. As shown in FIG. 6B, the control group was only injected with saline without any ultrasound and magnetic field exposure. The MMB+RMF group is treated with magnetic microbubbles in a rotational magnetic field (B=50 mT, f=20 Hz). The temperature changes in MMB+RMF treatment group is not significant compared to the control group. This indicates that the rotational magnetic field in the low frequency range (f<25 Hz) does not induce heating above the physiological temperature range. The MMB+US group and MMB+US+RMF group both have a slight temperature increase during the 30 min treatment. This is likely due to ultrasound exposure and the associated cavitation effects during the treatment. However, no significant change in temperature was observed in either MMB+US group or MMB+US+RMF group. This further indicates that the thrombolysis rate increase in the MMB+US+RMF group is not primarily attributed by the temperature changes and effects.

Thrombolysis Treatment with Different Clot Ages

Figure 7:
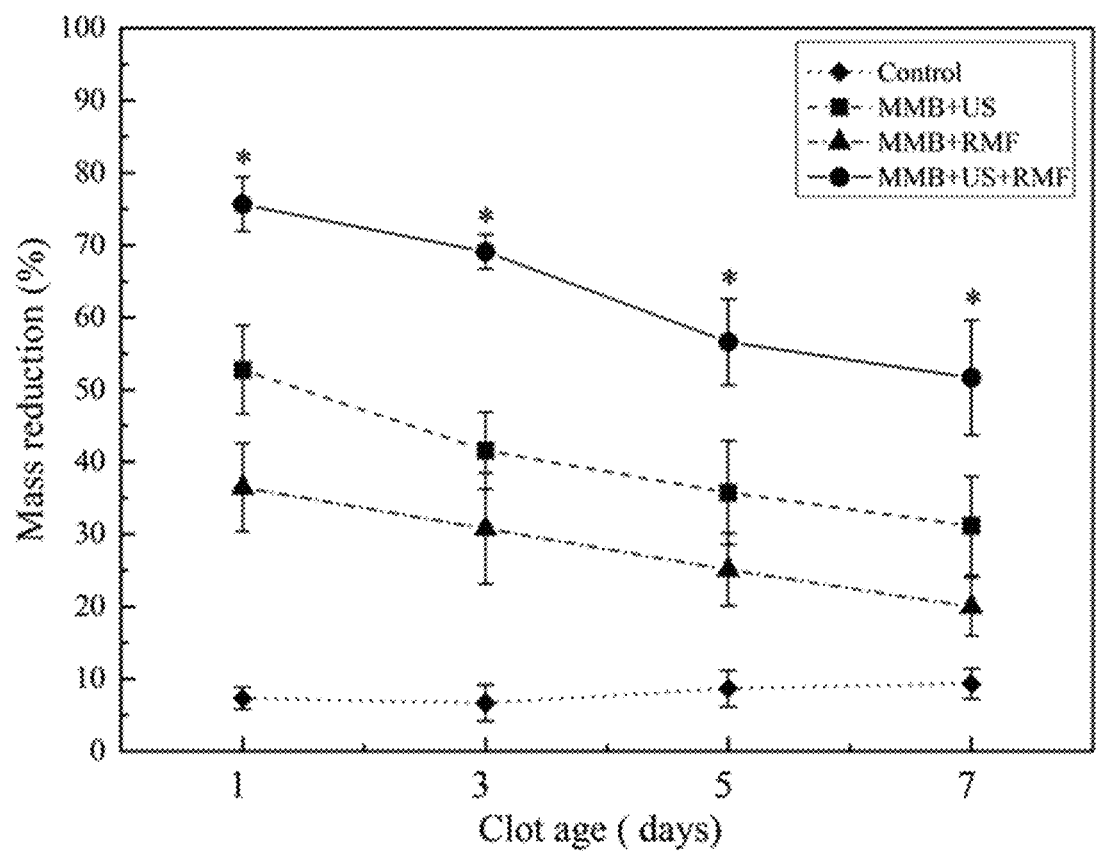
FIG. 7 is a graph illustrating in vitro test results using different treatment methods with different clot ages. Treatment time was 30 min, ultrasound parameters: 120 $V_{pp}$ input voltage, 10% duty cycle, f=620 kHz, magnetic field: B=50 mT, f=20 Hz. * indicates statistically different between group MMB+US+RMF (P<0.05).

According to our previous study [29], the fresh clot is considered as clot formed within 1 day and the retracted clot is considered as clot formed more than 3 days. Therefore, clot with ages from 1 day to 7 days was selected in this study to better understand the clot aging effect on the thrombolysis rate influence. To investigate the influence of clot ages on the thrombolysis treatment, the fully occluded blood clot flow model with flow pressure and the clot with different ages from 1 day to 7 days were used in this test. For each treatment, the same treatment parameters were used: 30 min treatment time, ultrasound input parameters (120 $V_{pp}$ input voltage, 10% duty cycle, f=620 kHz) and magnetic field parameters (magnetic field flux density B=50 mT, magnetic field frequency f=20 Hz). The control group was only injected with magnetic microbubbles without any ultrasound and magnetic field exposure. As shown in FIG. 7, the clot mass reduction rate slightly drops when clot ages increase. This is likely because as the clot ages increase, the clot condition changes from fresh to retracted. In the retracted clot, there will be more fibrin networks that prevent clot lysis. The fresh clots are much more easily to be dissolved during the treatment. However, the combined method (MMB+US+RMF) still shows a higher mass reduction rate than the ultrasound only (MMB+US) method significantly ($p<0.05$).

Thrombolysis Treatment with Different Input Parameters

Figure 8B:
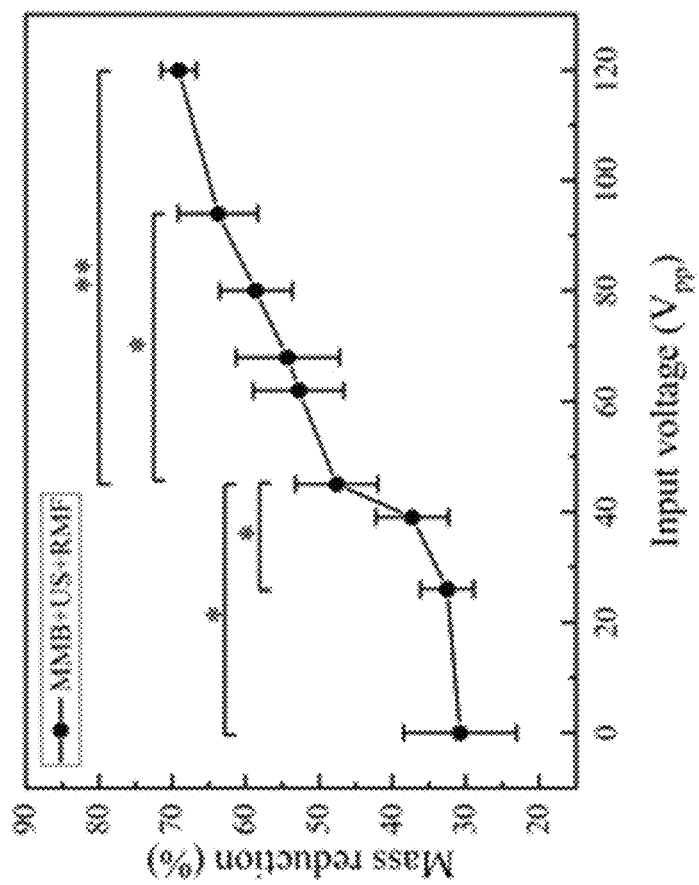
FIGS. 8A-8B are graphs illustrating in vitro test results using MMB+US+RMF treatment method with different ultrasound input: duty cycle (FIG. 8A), and the input voltage (FIG. 8B). Treatment time was 30 min, ultrasound parameters: f=620 kHz, magnetic field: B=50 mT, f=20 Hz. (*P<0.05, **P<0.01).
Figure 8A:
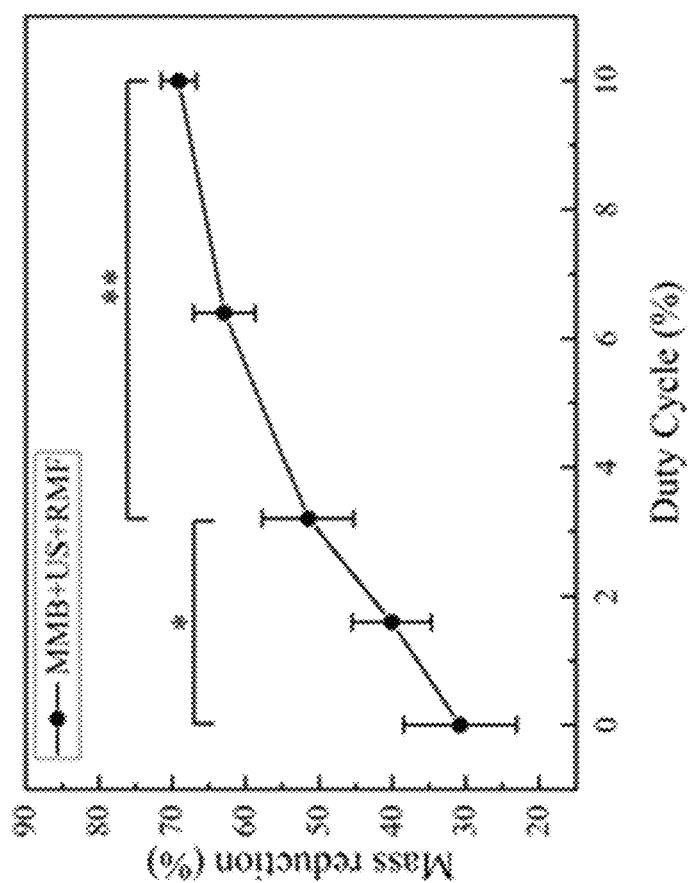

To clarify the thrombolysis effect of ultrasound, the rotational magnetic field, and magnetic microbubble combined treatment, various treatment cases were considered. As shown in FIG. 8A, different duty cycles were used as the ultrasound input parameter. The result shows that the clot mass reduction will increase when the duty cycle increase. As shown in FIG. 8B, when the input voltage increases from 0 to 120 $V_{pp}$, the clot mass reduction will increase. The in vitro test results using MMBs with various ultrasound input parameters had a similar tendency with the previously reported sonothrombolysis results obtained by using microbubbles [29]. The input voltages range from 26 $V_{pp}$ to 120 $V_{pp}$ were selected according to our previous study [29]: the higher input voltages, the higher peak negative pressure (PNP) and mechanical index (MI) can be achieved. However, due to the ultrasound transducer material limitation (45% of the AC depoling voltage for PZT-5A ceramics), 120 $V_{pp}$ was applied as an input voltage upper limit to keep the transducer working in a safe voltage range. The duty cycle ranges from 1.6% to 10% were used in this study according to our previous study [29]. The 10% (5 ms burst duration and 305 cycle-burst) was applied as a duty cycle upper limit to keep the transducer working in a safe range.

Figure 9B:
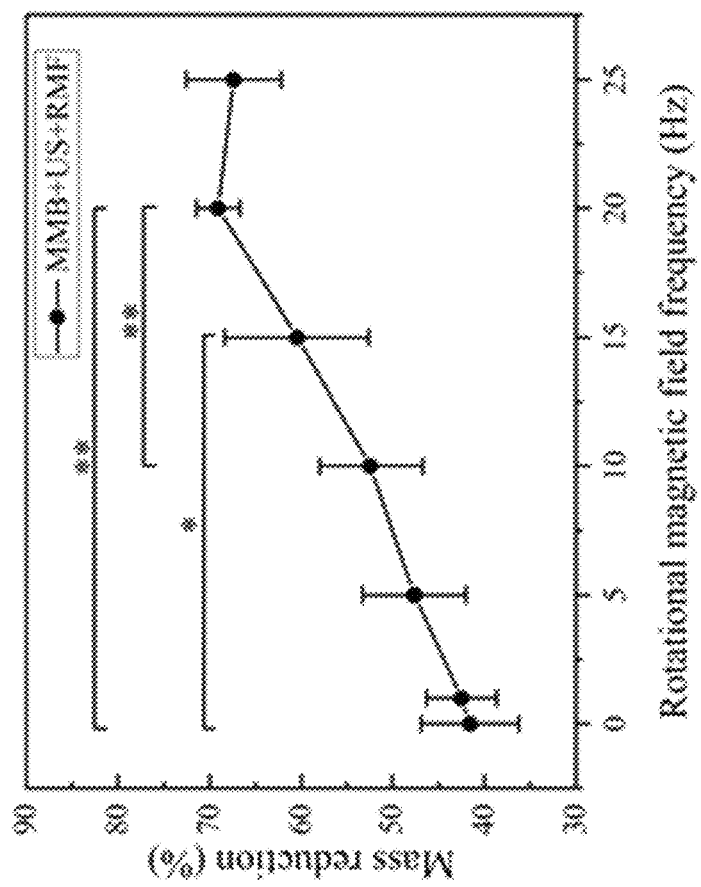
FIGS. 9A-9B are graphs illustrating in vitro test results using MMB+US+RMF treatment method with different magnetic field: flux density (FIG. 9A), and frequency (FIG. 9B). Treatment time was 30 min, ultrasound parameters: 120 $V_{pp}$ input voltage, 10% duty cycle, f=620 kHz. (*P<0.05, **P<0.01).
Figure 9A:
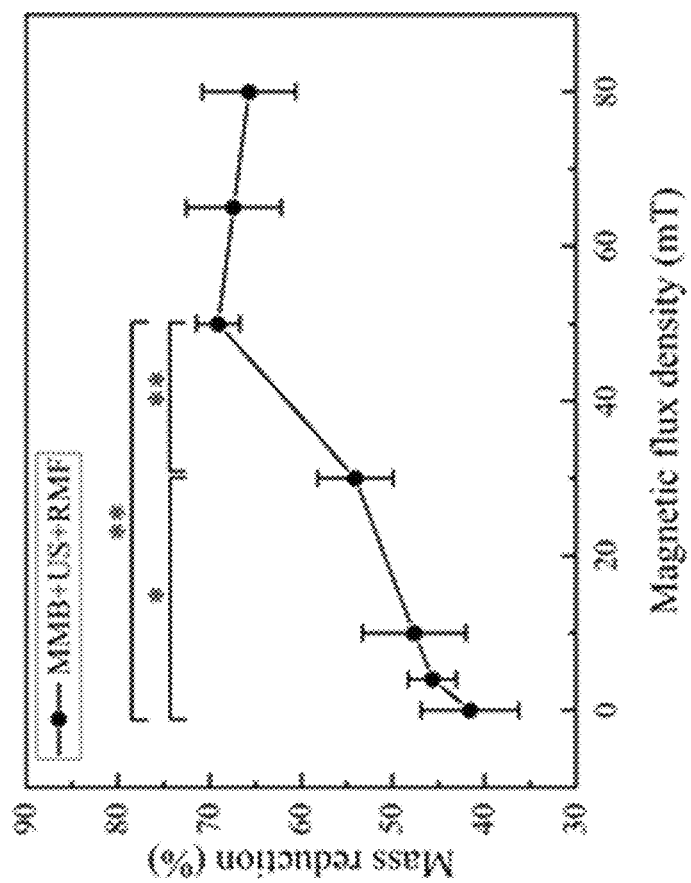

Next, the influence of magnetic field on the MMBs thrombolysis was investigated using the same ultrasound input parameter (120 $V_{pp}$ input voltage, 6.4% duty cycle, 620 kHz). As shown in FIG. 9A, the higher the magnetic field flux density, the higher clot mass reduction can be achieved. The possible reason can be explained as higher magnetic field flux density will induce the higher magnetic force applied on the magnetic microbubble, which will increase the vortex like microstreaming generated by the oscillating magnetic nanoparticles. To further investigate the influence of rotational magnetic field frequency on the lytic rate, the in vitro test was performed with different magnetic frequencies from static, 1 Hz to 25 Hz. As shown in FIG. 9B, the lytic rate was increased when a higher frequency rotational magnetic field was applied to the magnetic microbubble. This can be explained as higher frequency will increase the oscillation magnitude of magnetic microbubbles, and as a result, the magnetic microbubbles were more likely to be activated by the ultrasound and therefore induce more cavitation effect and microstreaming at the clot region.

The Mechanism of Sonothrombolysis with MMBs Under RMF

Figure 10A:
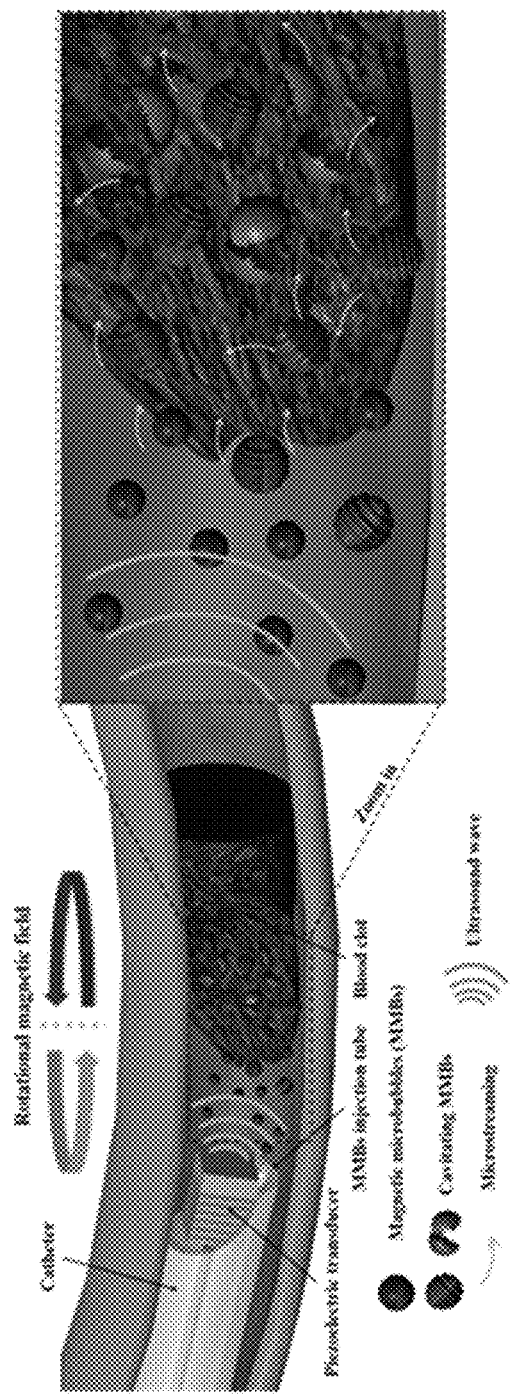
FIGS. 10A-10B illustrate schematic views of an embodiment of sonothrombolysis with magnetic microbubbles under a rotational magnetic field.
Figure 10B:
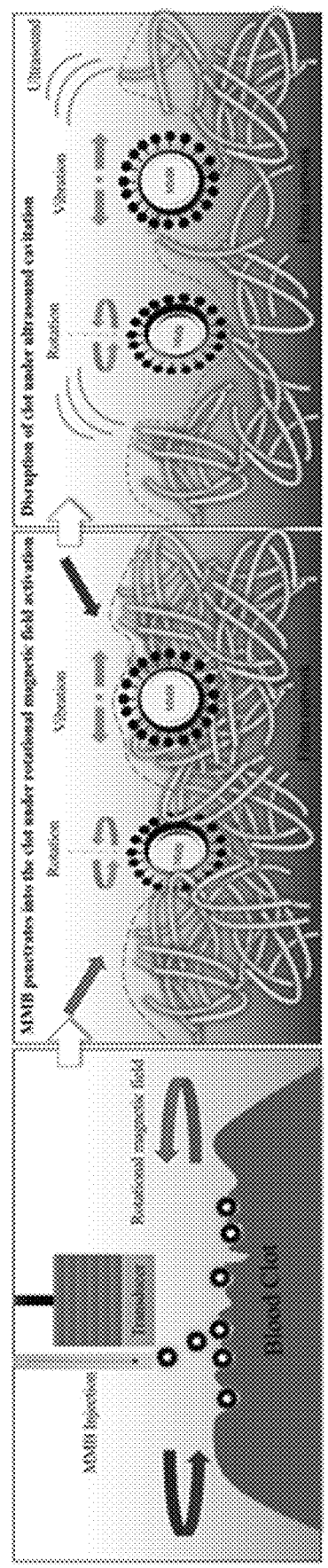

The proposed mode of magnetic microbubbles (MMBs) mediated intravascular sonothrombolysis by using a catheter-tipped forward-looking ultrasound transducer under a rotational magnetic field (RMF) is shown schematically in FIGS. 10A and 10B. First, the magnetic field can confine and trap the magnetic microbubbles around the clot region against blood flow and therefore increase the total concentration of magnetic microbubbles that retained at the clot surface for further ultrasound excitation. Second, when applied with the external rotational magnetic field, the magnetic microbubble will vibrate and oscillate at certain amplitude on the surface of the clot, resulting in a pair of counter-rotating vortices around the magnetic microbubbles, generating high shear flows, microjets, and microstreaming. Third, the fibrin network in the clot can be disrupted by the mechanical force generated from magnetic microbubble vibration and microstreaming under rotational magnetic field. Finally, the clot with disrupted fibrin network structure allows more magnetic microbubbles to diffuse beneath the clot surface and then magnetic microbubbles can be excited by ultrasound for cavitation to increase the clot lysis rate.

It is believed that sonothrombolysis with magnetic microbubbles using a catheter-tipped, forward-looking ultrasound transducer under a rotational magnetic field is more advantageous for effective thrombolysis by enhancing the disruption of fibrin network of the clot and cavitation-induced microstreaming than the conventional high frequency, catheter-based thrombolysis techniques. The current techniques for treating thrombosis disease have many disadvantages such as low thrombolytic efficiency, hemorrhage, high failure rate, vein injury and the risk of distal embolism due to the large size of clot debris. Recently, the catheter-based side-looking intravascular ultrasound thrombolysis has demonstrated the improved lytic rate using high-frequency, low-power ultrasound waves that enhance the drug diffusion [43,44]. However, this method cannot be effective for thrombolysis without a thrombolytic agent. Moreover, the side looking method still needs a relatively long treatment time (>10 hours on average) with the use of high dose of the thrombolytic agent. The methods of the present disclosure, initially realized a high thrombolysis rate (>60% mass reduction) in a short time (30 min) with in-vitro treatment without using any thrombolytic agent such as rt-PA. It is anticipated that this approach could be used for enhanced ultrasound-enhanced fibrinolysis by using rotational magnetic field in combination with magnetic microbubbles in order to lower or eliminate the dose of rt-PA thrombolytic agent while still achieving rapid thrombolysis treatment in the clinical application.

Magnetic Microbubbles Safety

Regarding safety, the magnetic microbubbles (MMBs) are similar to those microbubbles (MBs) contrast agents that were used in the clinical applications and whose toxicity profile are well understood. Any possible adverse effects of the presence of inorganic particles that were embedded in the MMBs as iron oxide magnetic nanoparticles must also be taken into consideration. Therefore, the potential risk of iron oxide nanoparticles in the human body can be investigated further. From the toxicological point of view, the toxicity of magnetic nanoparticles may depend on many factors such as the dose, size, structure, chemical composition, surface and biodegradability [30].

Size is an important factor in the toxicity assessments of nanoparticles, and for the most part, the toxicity and size of nanoparticles are inversely related [31]; that is, the smaller the size of nanoparticles, the higher the toxicity. For example, iron oxide particles are well known to be non-toxic and are finally broken down to form blood hemoglobin inside the body. However, when it comes to the nanoscale size, some studies have shown that the 30 nm sized iron oxide nanoparticles showed relatively higher toxicity compared to that of 500 nm sized particles [31].

Second, the influence of the surface coating affects the biocompatibility of nanoparticles. For example, it has been shown that the uncoated iron oxide nanoparticles caused a significant decrease (by ~64%) in the human fibroblasts cell adhesion compared to that of control cells, but the PEG-coated nanoparticles did not cause much change [32]. Studies performed on the toxicity of magnetite-loaded polymeric particles have demonstrated that polymer-coated nanoparticles had lower cytotoxicity than the uncoated magnetite nanoparticles. Moreover, many works have demonstrated that the biodegradable polymers were ideal nanoparticle surface coating materials since their minimum toxicity and the immunological response had been achieved [33,34]. Currently, in order to obtain microbubbles with high magnetic and acoustic sensitivities, iron oxide nanoparticles have been embedded into the shell of polymer and lipid-shelled microbubbles, encapsulated in the acoustically active liposphere or the surface of the shell structures [35]. However, the embedded rigid nanoparticles may increase the stiffness of the microbubble's shell and reduce their sensitivity to ultrasound [36], while a surface coating of the microbubbles with some immunogenic material may lead to the shell destabilization [37]. As a result, the stiffening effects and surface destabilization of the magnetic microbubbles could increase the risks of pulmonary entrapment [38]. Recently, researchers have found that by attaching heparin-functionalized iron oxide nanoparticles to the surface of lipid-shelled microbubbles, both the compressibility and surface stealth of microbubbles could be preserved [21].

Third, the dose of the magnetic microbubble also plays a role in the safety of clinical application. A recent study has demonstrated that iron oxide nanoparticles with a concentration below 100 µg/ml could be safe and non-cytotoxic [39]. Another in vitro cytotoxicity study showed that the iron oxide nanoparticles are nontoxic at lower concentrations from 0.1 to 10 µg/ml while cytotoxicity could be found at 100 µg/ml [40]. A previous study found that a dextran-coated iron oxide nanoparticle only induced some mild side effects like urticaria and could be degraded and cleared from systemic circulation by the iron metabolic pathways [41,42].

In summary, the magnetic microbubbles may be considered as biocompatible with additional safety parameters including, but not limited to, particle size, physicochemical composition, surface coating, dose range, and the like.

Conclusions

This example demonstrated that the additional use of magnetic microbubbles significantly enhances in vitro lysis of blood clot. The influence of blood flow conditions on the different thrombolysis treatment methods (MB+US, MMB+US, MMB+RMF, MMB+US+RMF) was compared. The influence of different vessel occlusion conditions (partial occlusion, fully occluded) and different clot ages (fresh, retracted) on the thrombolysis efficiency was also investigated. Finally, to better understand the mechanism of rotational magnetic field assisted sonothrombolysis, the influence of various ultrasound parameters (input voltage, duty cycle) and magnetic field parameters (amplitude, frequency) on the thrombolysis rate was explored. These results indicate the methods and systems of the present disclosure provide novel technology which utilizes various properties of magnetic microbubbles under both US and RMF to treat and optimize the thrombolysis of in vivo intravascular occlusions References for Example 1

[1] E. J. Benjamin, S. S. Virani, C. W. Callaway, A. M. Chamberlain, A. R. Chang, S. Cheng, S. E. Chiuve, M. Cushman, F. N. Delling, R. Deo, S. D. De Ferranti, J. F. Ferguson, M. Fornage, C. Gillespie, C. R. Isasi, M. C. Jiménez, L. C. Jordan, S. E. Judd, D. Lackland, J. H. Lichtman, L. Lisabeth, S. Liu, C. T. Longenecker, P. L. Lutsey, J. S. MacKey, D. B. Matchar, K. Matsushita, M. E. Mussolino, K. Nasir, M. O'Flaherty, L. P. Palaniappan, A. Pandey, D. K. Pandey, M. J. Reeves, M. D. Ritchey, C. J. Rodriguez, G. A. Roth, W. D. Rosamond, U. K. A. Sampson, G. M. Satou, S. H. Shah, N. L. Spartano, D. L. Tirschwell, C. W. Tsao, J. H. Voeks, J. Z. Willey, J. T. Wilkins, J. H. Y. Wu, H. M. Alger, S. S. Wong, P. Muntner, Heart disease and stroke statistics—2018 update: A report from the American Heart Association, Circulation. 137 (2018) E67-E492. doi:10.1161/CIR.0000000000000558.

[2] T. Truelsen, S. Begg, C. Mathers, The global burden of cerebrovascular disease, Glob. Burd. Dis. (2005) 1-67. doi:10.2135/cropsci2003.0425.

[3] J. H. Rha, J. L. Saver, The impact of recanalization on ischemic stroke outcome: A meta-analysis, Stroke. 38 (2007) 967-973. doi:10.1161/01.STR.000025-8112.14918.24.

[4] W. Hacke, M. Kaste, E. Bluhmki, M. Brozman, A. Dávalos, D. Guidetti, V. Larrue, K. R. Lees, Z. Medeghri, T. Machnig, D. Schneider, R. von Kummer, N. Wahlgren, D. Toni, Thrombolysis with Alteplase 3 to 4.5 Hours after Acute Ischemic Stroke, N. Engl. J. Med. 359 (2008) 1317-1329. doi:10.1056/NEJMoa0804656.

[5] T.N.I. of N.D. and S. rt-P.S.S. Group, Tissue Plasminogen Activator for Acute Ischemic Stroke, N. Engl. J. Med. 333 (1995) 1581-1588. doi:10.1056/NEJM199512-143332401.

[6] J. Edlow, Clinical Policy: Use of Intravenous tPA for the Management of Acute Ischemic Stroke in the Emergency Department., Ann. Emerg. Med. 61 (2013) 225-43. doi:10.1016/j.annemergmed.2012.11.005.

[7] B. C. V. Campbell, P. J. Mitchell, T. J. Kleinig, H. M. Dewey, L. Churilov, N. Yassi, B. Yan, R. J. Dowling, M. W. Parsons, T. J. Oxley, T. Y. Wu, M. Brooks, M. A. Simpson, F. Miteff, C. R. Levi, M. Krause, T. J. Harrington, K. C. Faulder, B. S. Steinfort, M. Priglinger, T. Ang, R. Scroop, P. A. Barber, B. McGuinness, T. Wijeratne, T. G. Phan, W. Chong, R. V. Chandra, C. F. Bladin, M. Badve, H. Rice, L. de Villiers, H. Ma, P. M. Desmond, G. A. Donnan, S. M. Davis, Endovascular Therapy for Ischemic Stroke with Perfusion-Imaging Selection, N. Engl. J. Med. 372 (2015) 1009-1018. doi:10.1056/NEJMoa1414792.

[8] S. Ricci, L. Dinia, M. Del Sette, P. Anzola, T. Mazzoli, S. Cenciarelli, C. Gandolfo, Sonothrombolysis for acute ischaemic stroke, Cochrane Database Syst. Rev. (2012). doi:10.1002/14651858.CD008348.pub3.

[9] O. A. Berkhemer, P. S. S. Fransen, D. Beumer, L. A. van den Berg, H. F. Lingsma, A. J. Yoo, W. J. Schonewille, J. A. Vos, P. J. Nederkoorn, M. J. H. Wermer, M. A. A. van Walderveen, J. Staals, J. Hofmeijer, J. A. van Oostayen, G. J. Lycklama à Nijeholt, J. Boiten, P. A. Brouwer, B. J. Emmer, S. F. de Bruijn, L. C. van Dijk, L. J. Kappelle, R. H. Lo, E. J. van Dijk, J. de Vries, P. L. M. de Kort, W. J. J. van Rooij, J. S. P. van den Berg, B. A. A. M. van Hassett, L. A. M. Aerden, R. J. Dallinga, M. C. Visser, J. C. J. Bot, P. C. Vroomen, O. Eshghi, T. H. C. M. L. Schreuder, R. J. J. Heijboer, K. Keizer, A. V Tielbeek, H. M. den Hertog, D. G. Gerrits, R. M. van den Berg-Vos, G. B. Karas, E. W. Steyerberg, H. Z. Flach, H. A. Marquering, M. E. S. Sprengers, S. F. M. Jenniskens, L. F. M. Beenen, R. van den Berg, P. J. Koudstaal, W. H. van Zwam, Y. B. W. E. M. Roos, A. van der Lugt, R. J. van Oostenbrugge, C. B. L. M. Majoie, D. W. J. Dippel, A Randomized Trial of Intraarterial Treatment for Acute Ischemic Stroke, N. Engl. J. Med. 372 (2014) 11-20. doi:10.1056/NEJMoa1411587.

[10] L. Auboire, C. A. Sennoga, J. M. Hyvelin, F. Ossant, J. M. Escoffre, F. Tranquart, A. Bouakaz, Microbubbles combined with ultrasound therapy in ischemic stroke: A systematic review of in-vivo preclinical studies, PLoS One. 13 (2018) e0191788. doi:10.1371/journal.pone.0191788.

[11] T. R. Porter, R. F. LeVeen, R. Fox, A. Kricsfeld, F. Xie, Thrombolytic enhancement with perfluorocarbon-exposed sonicated dextrose albumin microbubbles, Am. Heart J. 132 (1996) 964-968. doi:10.1016/S0002-8703(96)90006-X.

[12] S. Datta, C. C. Coussios, A. Y. Ammi, T. D. Mast, G. M. de Courten-Myers, C. K. Holland, Ultrasound-Enhanced Thrombolysis Using Definity® as a Cavitation Nucleation Agent, Ultrasound Med. Biol. 34 (2008) 1421-1433. doi:10.1016/j.ultrasmedbio.2008.01.016.

[13] A. Angelika, D. M. Alberto, S. Mark, F. Marc, G. Martin, P. Sibylle, S. Michel, H. Michael, A. Eric, M. Stephen, Molecular Imaging of Human Thrombus With Novel Abciximab Immunobubbles and Ultrasound, Stroke. 38 (2007) 1508-1514. doi:10.1161/STROKEAHA.106.471391.

[14] F. Xie, J. Lof, T. Matsunaga, R. Zutshi, T. R. Porter, Diagnostic ultrasound combined with glycoprotein IIb/IIIa-targeted microbubbles improves microvascular recovery after acute coronary thrombotic occlusions, Circulation. 119 (2009) 1378-1385. doi:10.1161/CIRCULATIONAHA.108.825067.

[15] M. J. Martin, E. M. L. Chung, A. H. Goodall, A. Della Martina, K. V. Ramnarine, L. Fan, S. V. Hainsworth, A. R. Naylor, D. H. Evans, Enhanced detection of thromboemboli with the use of targeted microbubbles, Stroke. 38 (2007) 2726-2732. doi:10.1161/STROKEAHA.107.489435.

[16] P. A. Schumann, J. P. Christiansen, R. M. Quigley, T. P. McCreery, R. H. Sweitzer, E. C. Unger, J. R. Lindner, T. O. Matsunaga, Targeted-microbubble binding selectively to GPIIb IIIa receptors of platelet thrombi, Invest. Radiol. 37 (2002) 587-593. doi:10.1097/00004424-200211000-00001.

[17] X. Wang, C. E. Hagemeyer, J. D. Hohmann, E. Leitner, P. C. Armstrong, F. Jia, M. Olschewski, A. Needles, K. Peter, I. Ahrens, Novel single-chain antibody-targeted microbubbles for molecular ultrasound imaging of thrombosis: Validation of a unique noninvasive method for rapid and sensitive detection of thrombi and monitoring of success or failure of thrombolysis in mice, Circulation. 125 (2012) 3117-3126. doi:10.1161/CIRCULATIONAHA.111.030312.

[18] P. Dayton, A. Klibanov, G. Brandenburger, K. Ferrara, Acoustic radiation force in vivo: A mechanism to assist targeting of microbubbles, Ultrasound Med. Biol. 25 (1999) 1195-1201. doi:10.1016/S0301-5629(99)00062-9.

[19] S. Zhao, M. Borden, S. H. Bloch, D. Kruse, K. W. Ferrara, P. A. Dayton, Radiation-force assisted targeting facilitates ultrasonic molecular imaging, Mol. Imaging. 3 (2004) 135-148. doi:10.1162/1535350042380317.

[20] J. J. Rychak, A. L. Klibanov, K. F. Ley, J. A. Hossack, Enhanced Targeting of Ultrasound Contrast Agents Using Acoustic Radiation Force, Ultrasound Med. Biol. 33 (2007) 1132-1139. doi:10.1016/j.ultrasmedbio.2007.01.005.

[21] B. Chertok, R. Langer, Circulating magnetic microbubbles for localized real-time control of drug delivery by ultrasonography-guided magnetic targeting and ultrasound, Theranostics. 8 (2018) 341-357. doi:10.7150/thno.20781.

[22] M. De Saint Victor, D. Carugo, L. C. Barnsley, J. Owen, C. C. Coussios, E. Stride, Magnetic targeting to enhance microbubble delivery in an occluded microarterial bifurcation, Phys. Med. Biol. 62 (2017) 7451-7470. doi:10.1088/1361-6560/aa858f.

[23] A. S. Drozdov, V. V. Vinogradov, I. P. Dudanov, V. V. Vinogradov, Leach-proof magnetic thrombolytic nanoparticles and coatings of enhanced activity, Sci. Rep. 6 (2016) 28119. doi:10.1038/srep28119.

[24] Y. Gao, C. U. Chan, Q. Gu, X. Lin, W. Zhang, D. C. L. Yeo, A. M. Alsema, M. Arora, M. S. K. Chong, P. Shi, C. D. Ohl, C. Xu, Controlled nanoparticle release from stable magnetic microbubble oscillations, NPG Asia Mater. 8 (2016) e260-10. doi:10.1038/am.2016.37.

[25] H. Mannell, J. Pircher, F. Fochler, Y. Stampnik, T. Räthel, B. Gleich, C. Plank, O. Mykhaylyk, C. Dahmani, M. Wörnle, A. Ribeiro, U. Pohl, F. Krötz, Site directed vascular gene delivery in vivo by ultrasonic destruction of magnetic nanoparticle coated microbubbles, Nanomedicine Nanotechnology, Biol. Med. 8 (2012) 1309-1318. doi:10.1016/j.nano.2012.03.007.

[26] M. D. Torno, M. D. Kaminski, Y. Xie, R. E. Meyers, C. J. Mertz, X. Liu, W. D. O'Brien, A. J. Rosengart, Improvement of in vitro thrombolysis employing magnetically-guided microspheres, Thromb. Res. 121 (2008) 799-811. doi:10.1016/j.thromres.2007.08.017.

[27] F. Bi, J. Zhang, Y. Su, Y. C. Tang, J. N. Liu, Chemical conjugation of urokinase to magnetic nanoparticles for targeted thrombolysis, Biomaterials. 30 (2009) 5125-5130. doi:10.1016/j.biomaterials.2009.06.006.

[28] J. Owen, P. Rademeyer, D. Chung, Q. Cheng, D. Holroyd, C. Coussios, P. Friend, Q. A. Pankhurst, E. Stride, Magnetic targeting of microbubbles against physiologically relevant flow conditions, Interface Focus. 5 (2015) 1-12. doi:10.1098/rsfs.2015.0001.

[29] J. Kim, B. D. Lindsey, W. Y. Chang, X. Dai, J. M. Stavas, P. A. Dayton, X. Jiang, Intravascular forward-looking ultrasound transducers for microbubble-mediated sonothrombolysis, Sci. Rep. 7 (2017) 1-10. doi:10.1038/s41598-017-03492-4.

[30] M. Arruebo, R. Fernández-Pacheco, M. R. Ibarra, J. Santamaria, Magnetic nanoparticles for drug delivery, Nano Today. 2 (2007) 22-32. doi:10.1016/S1748-0132(07)70084-1.

[31] H. L. Karlsson, J. Gustafsson, P. Cronholm, L. Möller, Size-dependent toxicity of metal oxide particles—A comparison between nano- and micrometer size, Toxicol. Lett. 188 (2009) 112-118. doi:10.1016/J.TOXLET.2009.03.014.

[32] A. K. Gupta, A. S. G. Curtis, Surface modified superparamagnetic nanoparticles for drug delivery: Interaction studies with human fibroblasts in culture, J. Mater. Sci. Mater. Med. 15 (2004) 493-496. doi:10.1023/B:JMSM.0000021126.32934.20.

[33] H. Otsuka, Y. Nagasaki, K. Kataoka, PEGylated nanoparticles for biological and pharmaceutical applications, Adv. Drug Deliv. Rev. 55 (2003) 403-419. doi:10.1016/S0169-409X(02)00226-0.

[34] A. Chilkoti, M. R. Dreher, D. E. Meyer, Design of thermally responsive, recombinant polypeptide carriers for targeted drug delivery, Adv. Drug Deliv. Rev. 54 (2002) 1093-1111. doi:10.1016/S0169-409X(02)00060-1.

[35] F. Yang, Y. Li, Z. Chen, Y. Zhang, J. Wu, N. Gu, Superparamagnetic iron oxide nanoparticle-embedded encapsulated microbubbles as dual contrast agents of magnetic resonance and ultrasound imaging, Biomaterials. 30 (2009) 3882-3890. doi:10.1016/j.biomaterials.2009.03.051.
[36] D. Vlaskou, O. Mykhaylyk, F. Krötz, N. Hellwig, R. Renner, U. Schillinger, B. Gleich, A. Heidsieck, G. Schmitz, K. Hensel, C. Plank, Magnetic and acoustically active liposphere for magnetically targeted nucleic acid delivery, Adv. Funct. Mater. 20 (2010) 3881-3894. doi:10.1002/adfm.200902388.
[37] C. C. Chen, M. A. Borden, The role of poly(ethylene glycol) brush architecture in complement activation on targeted microbubble surfaces, Biomaterials. 32 (2011) 6579-6587. doi:10.3233/MAS-2012-0234.
[38] A. Barrefelt, M. Saghafian, R. Kuiper, F. Ye, G. Egri, M. Klickermann, T. B. Brismar, P. Aspelin, M. Muhammed, L. Dähne, M. Hassan, Biodistribution, kinetics, and biological fate of SPION microbubbles in the rat, Int. J. Nanomedicine. 8 (2013) 3241-3254. doi:10.2147/IJN.549948.
[39] H. L. Karlsson, P. Cronholm, J. Gustafsson, L. Möller, Copper Oxide Nanoparticles Are Highly Toxic: A Comparison between Metal Oxide Nanoparticles and Carbon Nanotubes, Chem. Res. Toxicol. 21 (2008) 1726-1732. doi:10.1021/tx800064j.
[40] B. Ankamwar, T. C. Lai, J. H. Huang, R. S. Liu, M. Hsiao, C. H. Chen, Y. K. Hwu, Biocompatibility of Fe3O4 nanoparticles evaluated by in vitro cytotoxicity assays using normal, glia and breast cancer cells, Nanotechnology. 21 (2010) 75102. doi:10.1088/0957-4484/21/7/075102.
[41] Y. Anzai, C. W. Piccoli, E. K. Outwater, W. Stanford, D. A. Bluemke, P. Nurenberg, S. Saini, K. R. Maravilla, D. E. Feldman, U. P. Schmiedl, J. A. Brunberg, I. R. Francis, S. E. Harms, P. M. Som, C. M. Tempany, Group, Evaluation of neck and body metastases to nodes with feru-moxtran 10-enhanced MR imaging: phase III safety and efficacy study., Radiology. 228 (2003) 777-788. doi:10.1148/radiol.2283020872.
[42] R. Weissleder, D. D. Stark, B. L. Engelstad, B. R. Bacon, C. C. Compton, D. L. White, P. Jacobs, J. Lewis, Superparamagnetic iron oxide: pharmacokinetics and toxicity., AJR. Am. J. Roentgenol. 152 (1989) 167-73. doi:10.2214/ajr.152.1.167.
[43] C. A. Owens, Ultrasound-Enhanced Thrombolysis: EKOS EndoWave Infusion Catheter System., Semin. Intervent. Radiol. 25 (2008) 37-41. doi:10.1055/s-2008-1052304.
[44] N. Kucher, P. Boekstegers, O. J. Müller, C. Kupatt, J. Beyer-Westendorf, T. Heitzer, U. Tebbe, J. Horstkotte, R. Müller, E. Blessing, M. Greif, P. Lange, R.-T. Hoffmann, S. Werth, A. Barmeyer, D. Härtel, H. Grünwald, K. Empen, 1. Baumgartner, Randomized, Controlled Trial of Ultrasound-Assisted Catheter-Directed Thrombolysis for Acute Intermediate-Risk Pulmonary Embolism, Circulation. 129 (2014) 479-486. doi:10.1161/CIRCULATIONAHA.113.005544.

Example 2—Enhanced Sonothrombolysis with Combination of Magnetic Microbubbles and Nanodroplets Under a Rotational Magnetic Field The present example describes a new method using the rotational magnetic field oscillation and low-intensity sub-megahertz ultrasound stimulation of magnetic microbubbles (MMBs) to promote nanodroplets (NDs) phase transition and improve the permeation of NDs into the blood clot fibrin network to enhance the sonothrombolysis efficiency. This example demonstrates the influence of different treatment methods with a combination of MMBs and NDs on the thrombolysis rate of both unretracted and retracted clots, including factors such as stable and inertial cavitation, tPA effects, MMBs/NDs concentration ratio, sonication parameters (input voltage, duty cycle) and rotational magnetic field parameters (flux density, frequency). The results showed that the combination of MMBs and NDs could significantly enhance in vitro lysis of blood clots with an unprecedented lysis rate.

As described above, sonothrombolysis (STL), a procedure involved using microbubbles (MBs) and tPA with ultrasound to enhance thrombus dissolution, has been under clinical assessment as a method for recanalization of blocked blood vessels [9, 10]. Over the past few years, many studies have shown that sonothrombolysis with microbubbles is a comparatively safe and effective treatment method in thrombosis diseases compared to tPA-based therapy [11, 12]. The previous studies also demonstrated that a high concentration of microbubbles ($1.05 \times 10^9$ MBs/mL) would achieve a reasonable clot lysis rate (0.041 mg/min) due to a number of microbubbles cavitating in response to ultrasound [13]. However, most of the sonothrombolysis treatments are not efficient due to the fact that the limited number of microbubbles can be retained and cavitated at the site of the thrombus against blood flow during ultrasound exposure [14]. Another limitation of microbubbles for diagnostic and therapeutic applications includes their relatively rapid clearance time, low stability, poor tissue penetration, and short shelf life [15]. As an alternative, a significant amount of investigations in recent years have been focused on the development of nanodroplets [16, 17] for ultrasound imaging [18, 19], drug delivery [20], tissue ablation [21], and sonothrombolysis [22-24]. Due to the smaller size (100-300 nm) compared with microbubbles (1-10 µm), the circulation time and tissue permeability of nanodroplets are significantly enhanced [19]. While nanodroplets have demonstrated considerable potentials for various biomedical applications, the development of nanodroplets still encounters a few challenges, such as the relatively low conversion efficiency (the proportion of droplets undergoing a phase change) under low concentration or low-intensity ultrasound exposure [26]. However, high nanodroplets concentration or high ultrasound intensity would induce the risk of tissue and vessel damage [27]. Therefore, there is a need for a new thrombolysis technique that can enhance microbubble concentration and improve the nanodroplet conversion efficiency on the clot site, thus improving the thrombolysis rate.

Figure 11:
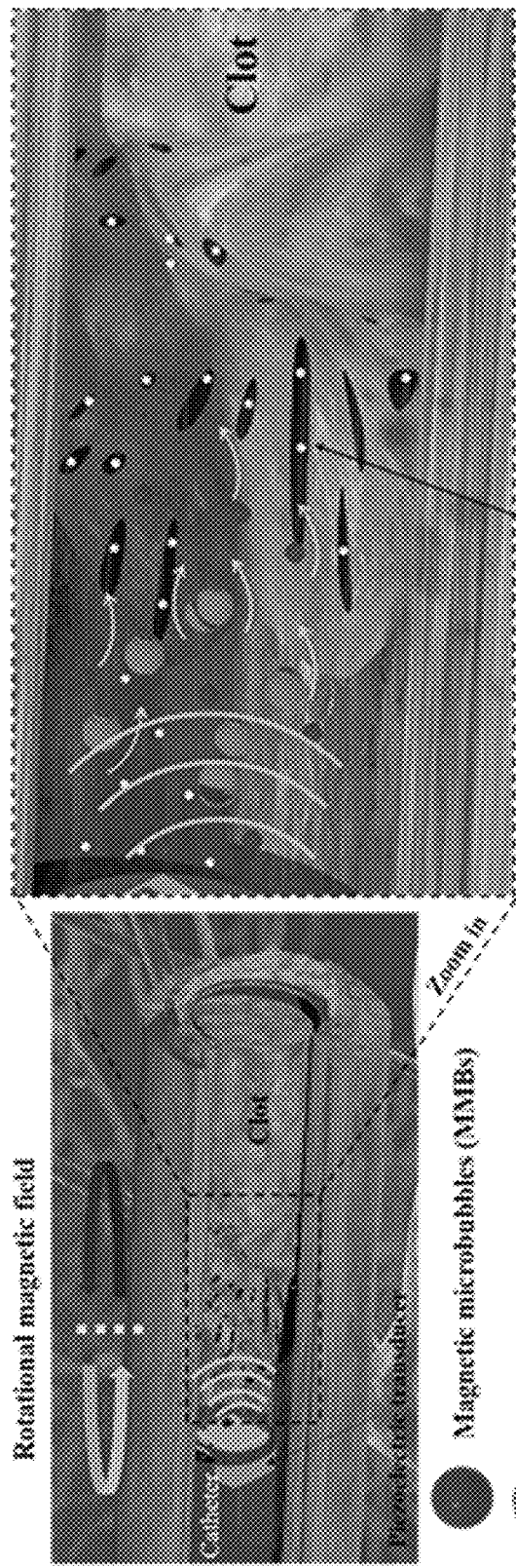
FIG. 11 is a schematic illustration of sonothrombolysis with nanodroplets and magnetic microbubbles under a rotational magnetic field. NDs and MMBs were injected through the catheter and trapped near the clot region under the rotational magnetic field. The cavitation and rotation of MMBs induce the microstreaming to the clot surface and cause mechanical injury to the fibrin network of the clot, which created the micro-channels to the clot surface. The NDs went through the micro-channels and could be activated by the ultrasound exposure and induce the cavitation effects inside the fibrin network, leading to the disruption of the clot

As described above, MMBs are microbubbles coated with superparamagnetic iron oxide nanoparticles (SPIONs) that can preserve the ultrasound acoustic response of microbubbles and retain the sensitivity to magnetic fields. The dual-modality functionality makes the MMBs advantageous for a broad range of applications, such as targeted drug delivery [28-31], contrast-enhanced ultrasonography [32-35], and sonothrombolysis [36-39]. However, there are still some challenges of using MMBs for targeted thrombolysis, such as the necessity of a controllable magnetic system to accumulate high concentration of MMBs precisely at the clot region and stimulate them with sufficient magnetic field strength and ultrasound power. To address these issues, a new approach of using MMBs for sonothrombolysis with intravascular forward-looking ultrasound transducer under a rotational magnetic field (RMF) was described above and in Example 1. Moreover, we recently found that nanodroplets-mediated sonothrombolysis could induce distinctive internal erosion in the middle of bovine clot samples compared to surface erosion generated by microbubble-mediated case [25]. The present example investigates whether MMBs can be a useful adjuvant to improve the nanodroplet conversion, permeation depth, and cavitation efficiency for the enhancement of thrombolysis treatment. As shown in FIG. 11, it appears that by oscillating and cavitating MMBs in an overlapping magnetic and acoustic field, a turbulent microstreaming induced in the clot region will enhance nanodroplet permeation into the clot fibrin network and consequently enhance the sonothrombolysis efficiency.

Figure 12:
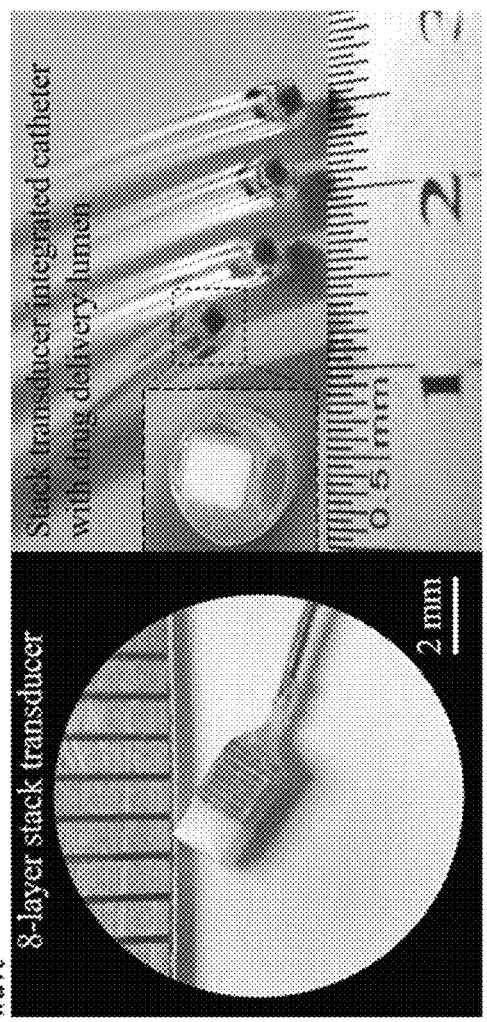
FIG. 12 illustrates images of a prototype of a developed 8-layer forward-looking stack transducer (left panel) integrated into a 9F catheter (right panel) with a drug delivery lumen (see insert) for MMBs and NDs injection.

This example investigates the influence of different treatment methods (ND+US, MMB+US, MMB+RMF, MMB+US+RMF, MMB+ND+US+RMF) on the thrombolysis of unretracted clot and retracted clot in a flow model. Then the cavitation effect (stable cavitation and inertial cavitation) and the correlation between clot mass reduction and cavitation doses were studied. The influence of tPA effects on the various treatment methods was also explored. To better understand the combined treatment effects of NDs and MMBs, the influence of NDs/MMB concentration ratios on thrombolysis rate was also evaluated. Finally, the influence of various sonication parameters (input voltage, duty cycle) and magnetic field parameters (flux density, frequency) on the thrombolysis efficiency was investigated Material and Methods Transducer Development A newly developed 8-layer PZT-5A forward-looking stacked ultrasound transducer was utilized in this study, as shown in FIG. 12. The specifics of the forward-looking transducer development method can be found in our prior work [42]. In brief, an 8-layer stacked piezoelectric transducer was built by using PZT-5A ceramic thin plates with alternating poling directions. The thickness of each PZT-5A layer was 200 µm, and the total thickness of the stacked transducer was 2.85 mm, including a 0.9 mm-thick matching layer. The electrically conductive adhesive (E-solder 3022, VonRoll USA, Inc.) was used to bond the layers, and the bonding layer thickness was about 30 µm. The transducer has a lateral width of 1.4 mm and can be installed on a 9F catheter (SonoVascular, Inc., Chapel Hill) for the intravascular test.

Blood Clot Preparation

Figure 14:
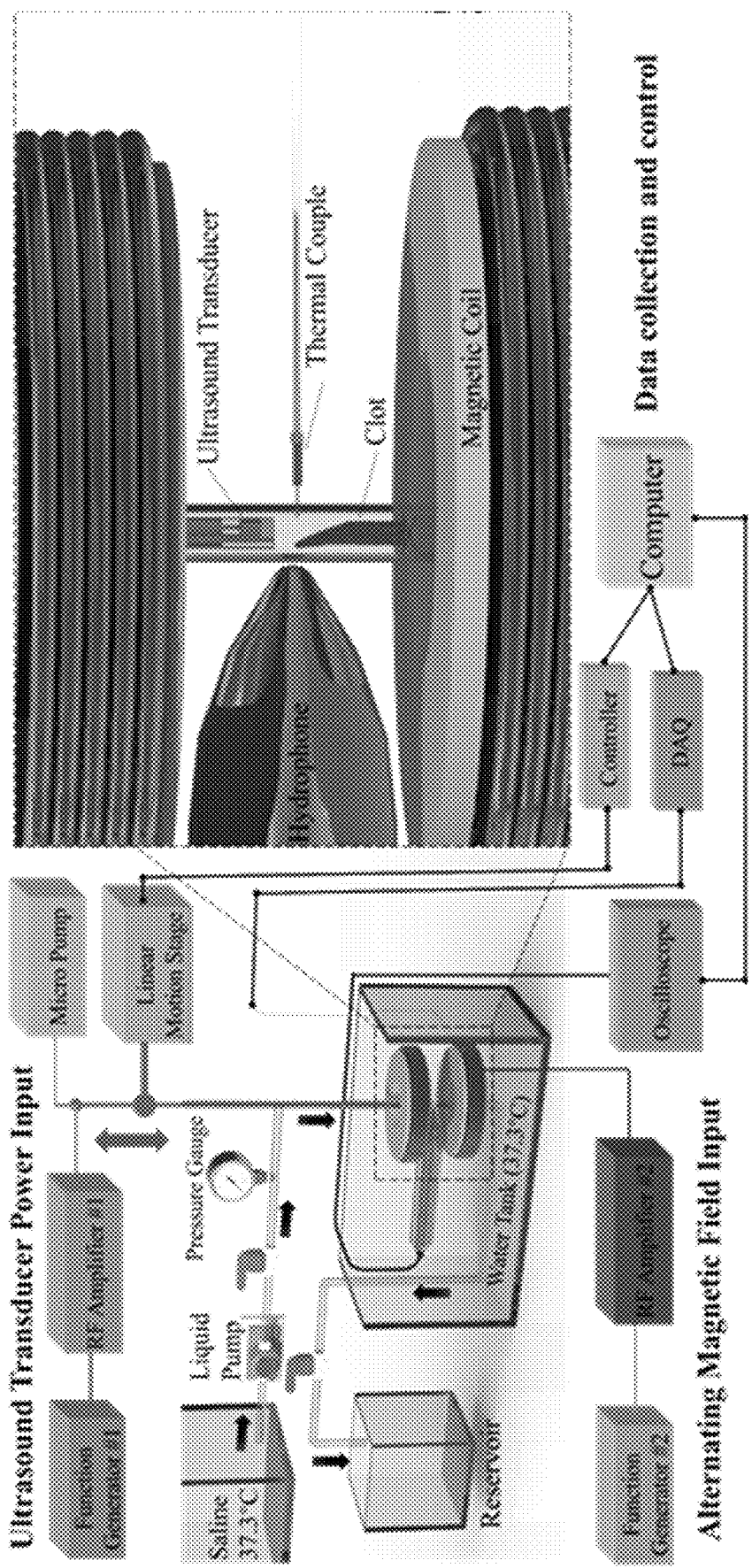
FIG. 14 illustrates an embodiment of an in vitro ultrasound thrombolysis system with magnetic microbubbles under a rotational magnetic field experiment setup

The unretracted and retracted clots were used in this study. The blood clots were prepared following a similar process used in our earlier work (Kim, et al., Sci. Rep. 2017, incorporated herein by reference). First, the fresh bovine blood acquired from Densco Marketing, Inc. (Wood-stock, Ill., USA) was mixed with 2.75% W/V Calcium Chloride solution (Fisher Scientific, Fair Lawn, NJ, USA) in a volume ratio of 10:1 (50 mL blood/5 mL $CaCl_2$ solution). Next, the blood mixture was transferred to plastic microcentrifuge tubes and borosilicate glass pipettes to form an unretracted clot and retracted clot, separately. Then the clots were incubated in a 37° C. water bath for 3 hours. Lastly, the clots were stored at low temperature (4° C.) for 3 to 14 days to generate different ages clot. Clot samples for thrombolysis experiments were cut into a cylindrical shape (length: 10±2 mm, diameter: 3±0.5 mm) and weighted as 120 mg±10% in mass and then positioned into a venous flow model, as shown in FIG. 14.

Magnetic Microbubbles Preparation

The magnetic microbubbles were formulated by a comparable method, as described in Gao, et al., NPG Asia Mater. 2016 (incorporated herein by reference). First, magnetic nanoparticles ($Fe_3O_4$, with a diameter around 50 nm, Sigma-Aldrich, St Louis, MO, USA) were combined with deionized water to create a 2 mg/mL stock mixture and then dispersed with ultrasound for 20 min. Next, a mixture containing 400 µl of a stock mixture of $Fe_3O_4$ nanoparticles, 150 µl of 10 mM sodium dodecyl sulfate (SDS), and 150 µl of deionized water was mixed by oscillating for 1 min [43]. Lastly, MMBs were left 24 hours before being washed with phosphate-buffered saline (PBS) three times before use. The prepared MMBs had a median diameter of ~3 µm.

Nanodroplets Preparation

The nanodroplets were prepared by a similar method, as previously described in Sheeran, et al., Biomaterials, 2012, and Kim et al., Ultrasound Med. Biol., 2020 (which are hereby incorporated herein by reference). First, nanodroplets precursors were formed by mechanical agitation of a 1:1 ratio of decafluorobutane and dodecafluoropentane. Then, the mixture was condensed under pressure and low temperature to form 240±65 nm diameter droplets. The concentration of each stock solution was about $1 \times 10^{10}$/mL. In this study, each solution was diluted into a concentration of $1 \times 10^8$/mL using sterile saline for the further in-vitro test.

The Rotational Magnetic Fields Generation

Figure 13A:
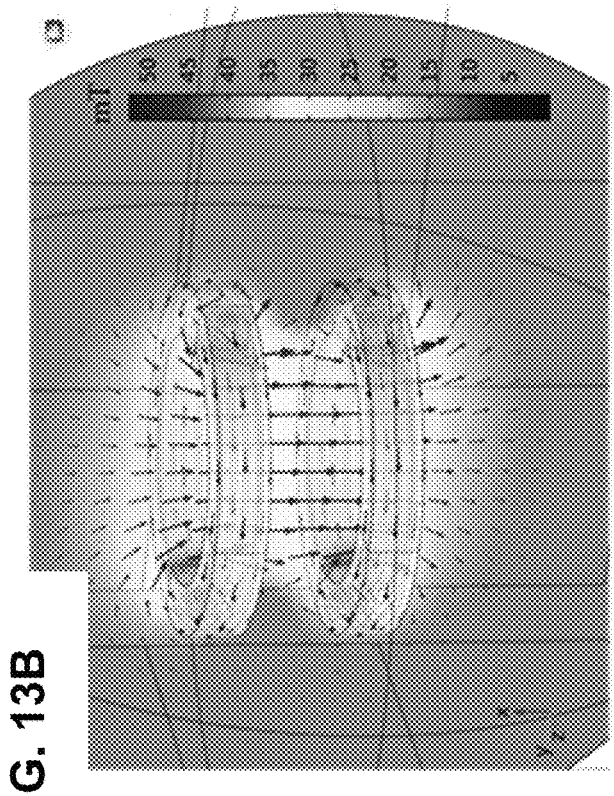
FIGS. 13A-13C illustrate a simulation of the magnetic field created by a Helmholtz coil in the space.

The rotational magnetic fields were generated by a Helmholtz pair, which consists of two identical circular magnetic coils (R=35 mm, N=200 turns, 22 AWG wire) that are placed symmetrically along a common axis. The Helmholtz coil can generate a region of the uniform magnetic field when the distance between each coil is equal to the coil radius, and the electric current shares the same direction. The Helmholtz coil was driven by a 40 dB RF power amplifier (Type 2706, Brüel & Kjæaer, Inc.), and the input signal was generated by a function generator (AFG 3101, Tektronix, Inc., Beaverton, OR, USA). By changing the frequency and amplitude of the input signal (sine wave), the rotational magnetic fields with a different frequency (0-100 Hz) and magnetic flux density (0-30 mT) were generated. As shown in FIG. 13A, the clot inside a flow model channel is positioned at the center of the Helmholtz coil center axis along with the direction of the magnetic flux density norm produced by the uniform rotational magnetic field.

The Simulation of the Rotational Magnetic Field

Figure 13B:
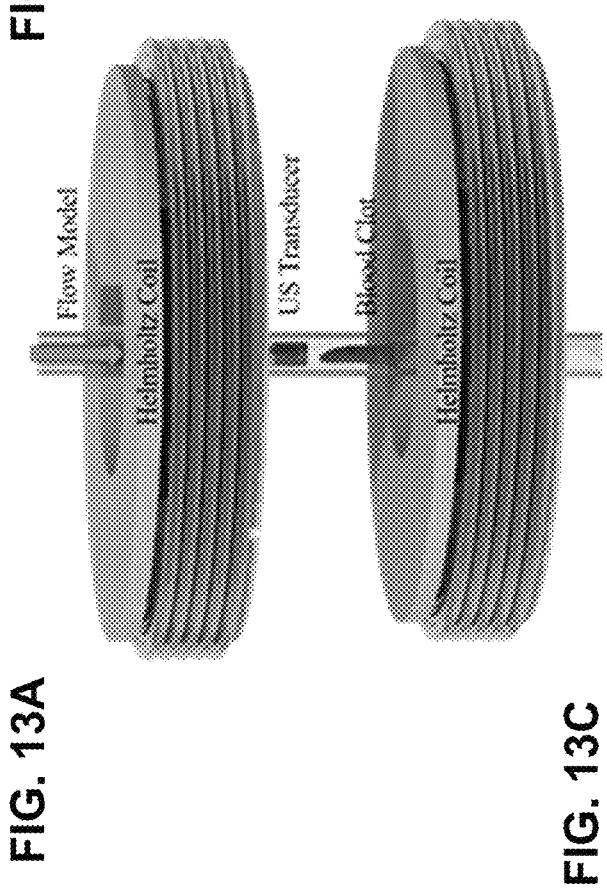
Figure 13C:
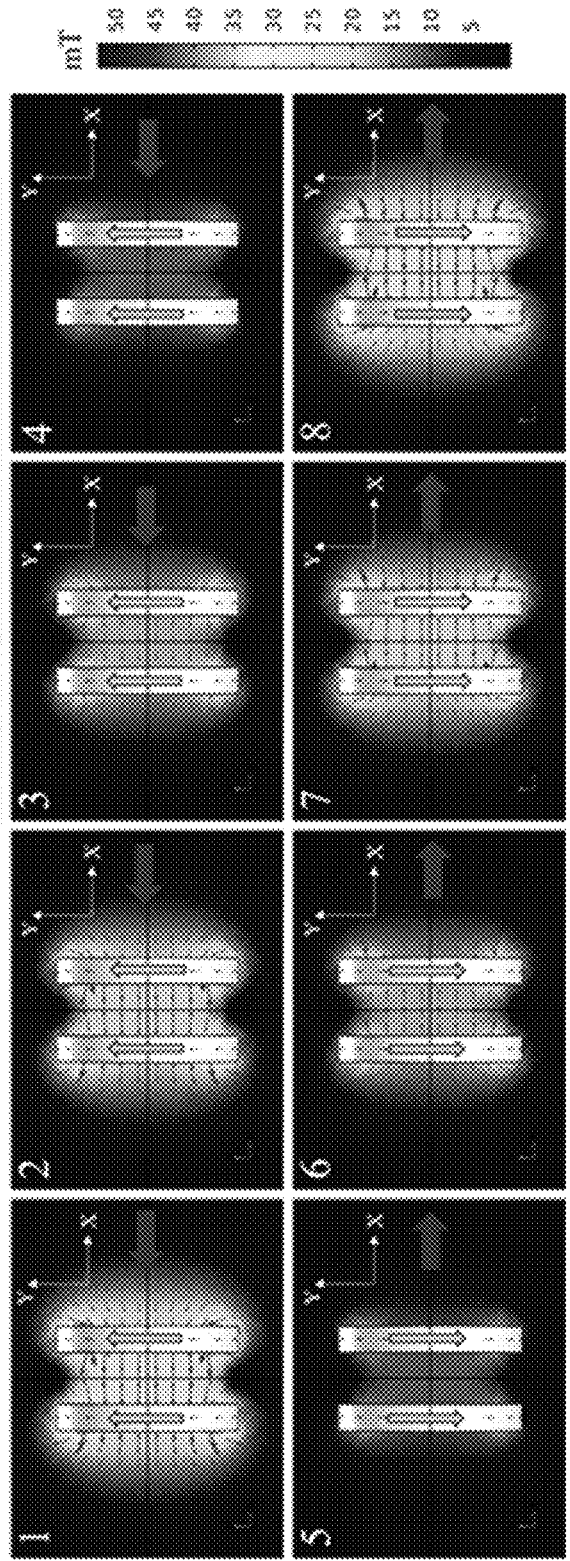

To better understand the physics of the rotational magnetic field, the magnetic field generated by the Helmholtz coil was simulated in the COMSOL® Multiphysics software (COMSOL, Inc., Burlington, MA, USA). The simulated magnetic flux density of the Helmholtz coil in the XY plane, as shown in FIG. 13B. The small arrows represent the direction of the magnetic flux density norm, and the circular bands of arrows represent the current direction in the coils. The simulation results showed a uniform magnetic field between the parallel coils, and all the magnetic flux density norm is uniformly aligned in one direction when the input current of the coil is in a clockwise direction. FIG. 3C showed the magnetic flux density change when the coil was driven by a sine wave signal with the frequency 50 Hz. First, The magnetic flux density at maximum (B=30 mT) in FIG. 3 (C1) was gradually decreased to a minimum (B=0 mT) in FIG. 3 (C4) while the magnetic flux density norm was pointing to (−X) direction (horizontal arrow) with alternating current (AC) direction in (+Y) direction (vertical arrow). Second, when the AC input reaches its minimum zero, the direction of AC (blue arrow) changes to the (−Y), as shown in FIG. 3 (C5). At the same time, the magnetic flux density gradually increased to its maximum (B=30 mT) in FIG. 3C (8) while the magnetic flux density norm was pointing to (+X) direction (red arrow). Therefore, under different driven frequency, the rotational magnetic field created a rotational force field that was converted inside the magnetic microbubbles into a magnetic flux field B, which applied the magnetic microbubbles with a magnetic Moment M and a moment of inertia I. The magnetic field generated torque and stimulated the rotation of the magnetic microbubbles around their axis. Thus, the rotational motion of magnetic microbubbles can be controlled by changing the rotational magnetic field frequency and amplitude.

In Vitro Tests

As shown in FIG. 14, for each in vitro treatment test, a 120 mg±10% clot sample was positioned into a Tygon tube (ID=4 mm, OD=5.5 mm) in a flow model. The flow model started with a water tank filled with saline at a temperature of 37.3±0.3° C. The saline was pumped from the saline reservoir into the flow model tube by a peristaltic pump (INTL-LAB, China). The blue color water valve after the liquid pump was used to adjust the inlet flow speed and water pressure. The liquid pressure inside the flow model was measured by a digital pressure gauge (DPGA-04, Dwyer Instruments, Inc., Michigan City, IN, USA) and kept at 3.7 mmHg pressure level by controlling the liquid pump and water valve before the reservoir. The flow outlet of the tube was connected to a reservoir to collect the saline and clot debris after the thrombolysis treatment. The clot region temperature change during the treatment was measured by a thermocouple (OMEGA Engineering, Norwalk, CT, USA), and the data was collected by a DAQ device (USB-6356, NI Inc., Austin, TX, USA) through a computer. The ultrasound transducer was mounted on an 8F catheter (OD=2.67 mm), and the transducer position was controlled by a linear motion stage (NRT100, Thorlabs, Inc., Newton, NJ, USA) to control the distance between the transducer and the clot front surface (~0.5 mm). The ultrasound transducer was driven by a 53 dB RF power amplifier (75A250A, AR, Inc., Souderton, PA, USA), and the input signal was generated by a function generator (33250A, Agilent Technologies, Inc., Loveland, CO, USA). The Helmholtz coil was positioned inside the water tank at a temperature of 37.3±0.3° to prevent the coil overheat during the treatment.

To deliver the magnetic microbubbles and nanodroplets solution into the tube, a micropump (DUAL-NE-1010-US, New Era Pump Systems Inc., Farmingdale, NY, USA) was used, and the injection flow rate was maintained at 100 μL/min. The cavitation signal was detected by a hydrophone (HGL-0085, ONDA Corp., Sunnyvale, CA, USA), which was positioned in the water tank at 1 mm from the clot. To investigate the influence of different thrombolysis treatment methods in a flow model, the retracted clot and unretracted clot were used. First, the blood clot was cut into a small-sized cylindrical shape (length: 10±2 mm, diameter: 3±0.5 mm) and weighted as 120 mg±10% in mass and then positioned into a flow model tube as shown in FIG. 14. The 3D printed cross-shape stopper (OD=4 mm) with meshes (d=300 μm) was used to fix the clot at the center position of the magnetic fields and prevent the clot from flowing away during thrombolysis treatment. Since the tube was partially occluded by the blood clot before the treatment, there will be a small amount of liquid flow out from the outlet of the tube into the reservoir. However, during the thrombolysis treatment, the clot size slowly decreased and caused the increasing amount of outlet flow. Therefore, to maintain a steady flow speed and pressure inside the flow model, the valve was manually adjusted during the treatment process.

The magnetic microbubbles (concentration: $10^9$/mL, average diameter ~3 μm) and nanodroplets (concentration: $10^8$/mL, average diameter ~300 nm) solutions were injected through a biocompatible silicone microtube (ID=0.64 mm, OD=1.19 mm, REF 60-411-42, Freudenberg Medical, LLC., Carpinteria, CA, USA) by a micropump at 100 μL/min infusion rate. The rotational magnetic field (RMF) with magnetic flux density B=20 mT, and frequency f=40 Hz generated by Helmholtz coil was applied to the clot area to activate the magnetic microbubbles. Finally, the ultrasound transducer with a sine-wave input signal as 80 $V_{pp}$ input voltage and 10% duty cycle was aligned and positioned near the clot surface (~0.5 mm) to cavitate the magnetic microbubbles and nanodroplets for the 30 min thrombolysis treatment.

To evaluate the influence of ultrasound and rotational magnetic fields on magnetic microbubbles and nanodroplets mediated thrombolysis treatment process, different treatment methods were operated under the similar procedure described above. To be specific, the control group was only injected with MMBs and NDs solution without any ultrasound or magnetic field exposure. The ND+US group was treated with nanodroplets (concentration: $10^8$/mL) and ultrasound. The MMB+US group was treated with magnetic microbubbles and ultrasound only without a magnetic field. The MMB+RMF group was treated with magnetic microbubbles and rotational magnetic fields only without ultrasound. The MMB+US+RMF group was treated with magnetic microbubbles and both ultrasound and rotational magnetic fields at the same time. The MMB+ND+US+RMF was treated with magnetic microbubbles and nanodroplets under the rotational magnetic field and ultrasound. The cavitation signals were detected by a hydrophone for each treatment group, and the data was sampled by the oscilloscope (DSO7104B, Agilent Technologies, Santa Clara, CA, USA). The cavitation doses for stable and inertial cavitation were calculated using MATLAB (MathWorks, Natick, MA, USA) following a similar process in Example 1, above.

Moreover, to clarify the influence of tPA effects in the MMBs and NDs-mediated thrombolysis treatment in a flow model, different treatment groups with low dose tPA (0.75 μg/mL) were used in the test.

To clarify the influence of MMBs and NDs concentration mixture ratio on the thrombolysis treatment, different NDs/MMBs concentration mixture ratios were investigated. The control group was only injected with NDs (concentration: $10^8$/mL) without MMBs and treated with ultrasound only. In other treatment group, the NDs concentration was kept at same value ($10^8$/mL) while changing the MMBs concentration as $10^6$/mL, $10^7$/mL, $10^8$/mL, $10^9$/mL and $10^{10}$/mL to have a NDs/MMBs mixture ratio as 100:1, 10:1, 1:1, 1:10 and 1:100.

Finally, to clarify the thrombolysis effect of ultrasound, rotational magnetic field, nanodroplets, and magnetic microbubbles (MMB+ND+US+RMF) combined treatment method, various treatment cases were considered. Both retracted and unretracted clot were exposed to ultrasound with different duty cycle (2.35%, 3.52%, 4.7%, 7.36%, 10%), input voltage (10 $V_{pp}$ to 120 $V_{pp}$), and rotational magnetic fields with different magnetic flux density (5 mT, 10 mT, 15 mT, 20 mT, 25 mT, 30 mT), and frequency (Static, 10 Hz to 100 Hz). The results shown in this study were stated as the mean±SD (n=3). Statistical analysis was performed using the MATLAB Statistical Toolbox (MathWorks, Natick, MA, USA). The student's t-test was employed to estimate the statistical significance of tests with various treatment conditions.

Results and Discussion

Thrombolysis with Different Treatment Methods in a Flow Model

Figure 15:
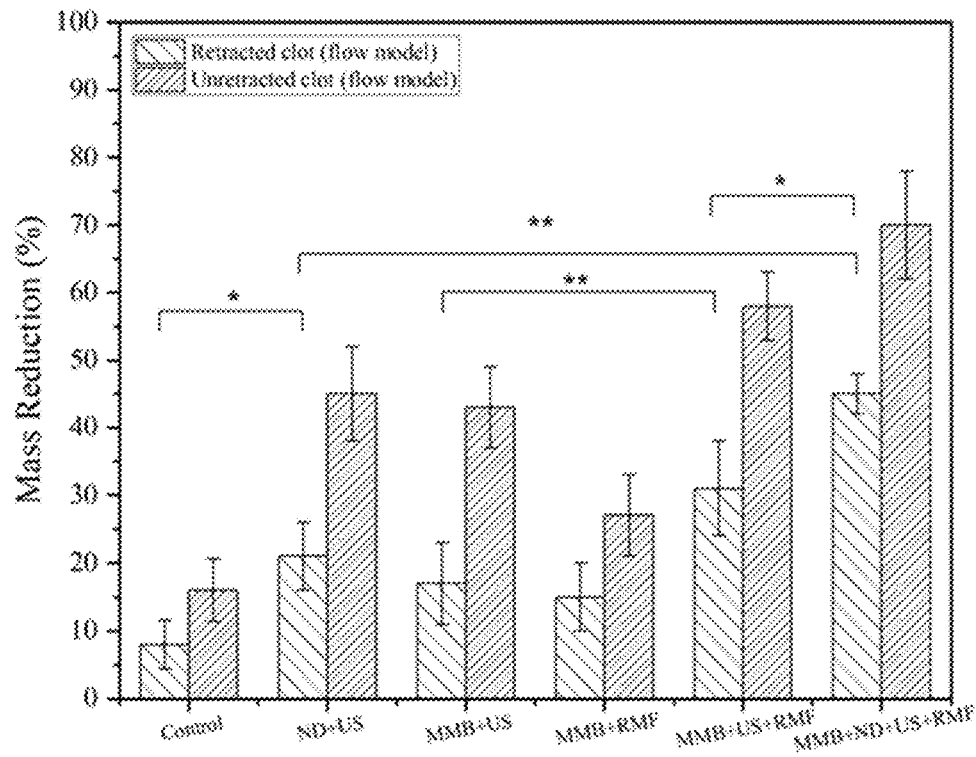
FIG. 15 is a bar graph illustrating in vitro test results using different treatment methods for retracted and unretracted clot in a flow model. (Treatment time: 30 min, ultrasound parameters: 80 $V_{pp}$ input voltage, 4.7% duty cycle, f=850 kHz, magnetic field: B=20 mT, f=40 Hz) (*P<0.05, **P<0.01).

While Example 1 demonstrated the effectiveness of sonothrombolysis with MMBs under a rotational magnetic field for the unretracted clot, the feasibility of MMBs and NDs-mediated sonothrombolysis under a rotational magnetic field in a flow model for both retracted and unretracted clots was unexplored. Therefore, to investigate the combined thrombolysis effect of MMBs and NDs on the retracted and unretracted clot, different groups of methods (ND+US, MMB+US, MMB+RMF, MMB+US+RMF, MMB+ND+US+RMF) were used for the thrombolysis treatment in a flow model. For each treatment, the same treatment parameters were used: 30 min treatment time, ultrasound input parameters (80 $V_{pp}$ input voltage, 4.7% duty cycle, f=850 kHz) and magnetic field parameters (magnetic field flux density B=20 mT, magnetic field frequency f=40 Hz). As shown in FIG. 15, among all the treatment groups, the clot mass reduction rate of the unretracted clot (average: 48.6±6.1%) was much higher than the retracted clot (average: 22.8±4.9%). This outcome was likely because the retracted clot was denser and stiffer than the unretracted clot, which might prevent the clot from being dissolved during thrombolysis treatment.

Moreover, the clot mass reduction rate using magnetic microbubbles and nanodroplets treated by a combined method of ultrasound and the rotational magnetic field (MMB+US+RMF, MMB+ND+US+RMF) was much higher than the group that treated with ultrasound only (ND+US, MMB+US) or rotational magnetic field only (MMB+RMF). The statistics result also showed there was a significant difference (P<0.01) between the MMB+US group (43±6%) and MMB+ND+US+RMF group (70±8%) for the unretracted clot. For the retracted clot, the ND+US (21±5%), MMB+US (17±6%), and MMB+RMF (15±5%) groups were not shown a significant difference (P<0.01) compared to the control group (8±3.6%). However, by using the combined treatment method, the clot mass reduction (MMB+US+RMF (31±7%) and MMB+ND+US+RMF (45±3%)) for retracted clot was significantly improved (P<0.01) compared to ultrasound only group (ND+US (21±5%) and MMB+US (17±6%)). On the one hand, this indicated that the rotational magnetic fields applied with the magnetic microbubbles could enhance the nanodroplets-mediated ultrasound thrombolysis treatment. On the other hand, by combining MMBs and NDs with ultrasound and rotational magnetic field, the retracted clot could realize a two times higher lysis rate (1.5±0.1%/min) than the NDs with ultrasound only (0.7±0.16%/min) and MMBs with ultrasound only (0.57±0.2%/min) case, indicating possible synergistic effects.

Cavitation Dose Comparison for Different Treatment Methods

Figure 16:
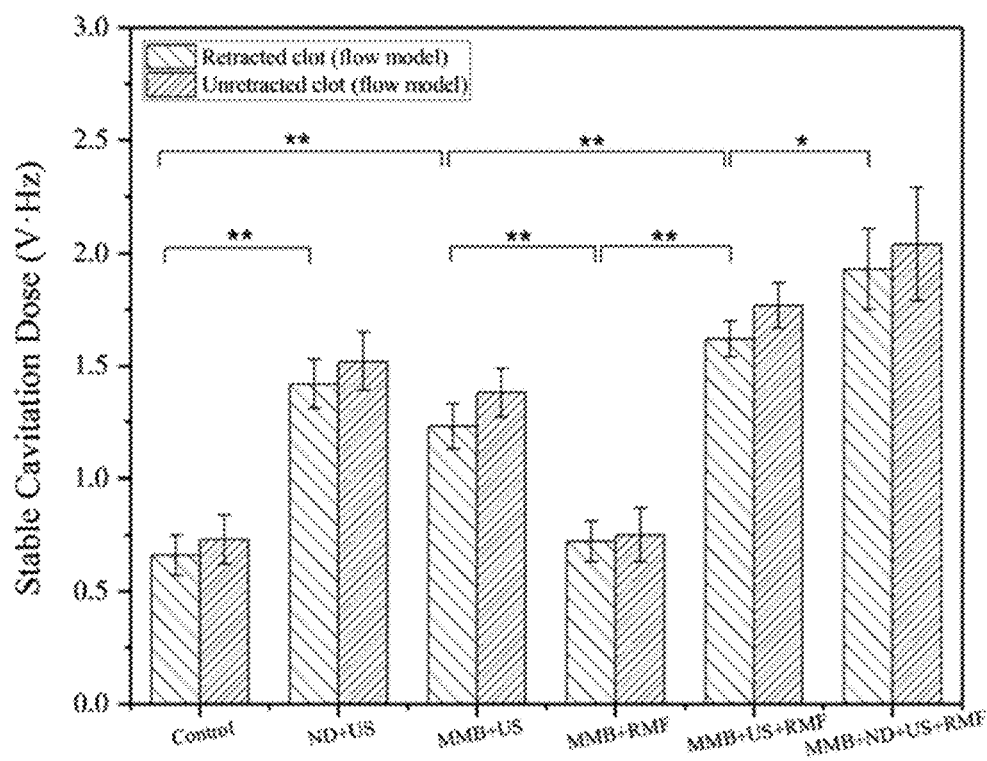
FIG. 16 is a graph illustrating stable cavitation dose (V·Hz) using different treatment methods for retracted and unretracted clot in a flow model. (Treatment time: 30 min, ultrasound parameters: 80 $V_{pp}$ input voltage, 4.7% duty cycle, f=850 kHz, magnetic field: B=20 mT, f=40 Hz) (*P<0.05, **P<0.01).

To clarify the influence of cavitation effects on different treatment methods, the cavitation signals detected from a hydrophone during each treatment process were analyzed. The stable and inertial cavitation doses were calculated for each treatment method following a previous procedure [44], and the correlation between cavitation dose and clot mass reduction was studied. As shown in FIG. 16, there was no significant difference for the stable cavitation dose between the retracted clot and unretracted clot among all the treatment groups. However, the results showed that there was a significant difference (p<0.01) between the ultrasound alone group ND+US (1.42±0.11 V·Hz), MMB+US (1.23±0.10 V·Hz), and the control group (0.66±0.09 V·Hz) for the retracted clot. This result indicated that the stable cavitation played an essential role in the NDs and MMBs mediated ultrasound thrombolysis treatment methods.

Moreover, for the retracted clot, the rotational magnetic field enhanced thrombolysis treatment methods MMB+US+RMF (1.62±0.08 V·Hz), and MMB+ND+US+RMF (1.93±0.18 V·Hz) have significantly higher (p<0.01) stable cavitation dose compared to ultrasound alone group MMB+US (1.23±0.10 V·Hz). This finding indicated that the rotational magnetic field with magnetic microbubbles could significantly enhance (>31.7%) the stable cavitation during the ultrasound thrombolysis treatment. This outcome was likely because the magnetic field could retain the MMBs against the flow so that the concentration of cavitation nuclei was increased, which resulted in higher stable cavitation activity.

Figure 17:
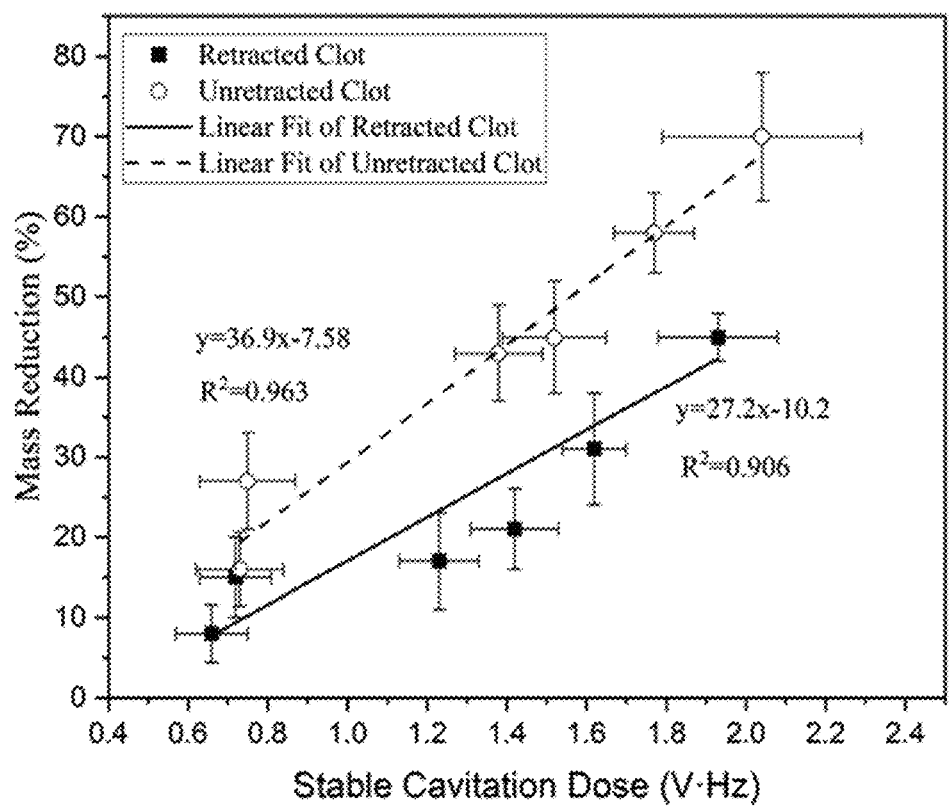
FIG. 17 is a graph illustrating the correlation between clot mass reduction (%) and stable cavitation dose (V·Hz) using different treatment methods for a retracted and unretracted clot in a flow model.

To clarify the relationship between stable cavitation and mass reduction of the retracted clot and unretracted clot using different treatment methods, the linear regression analysis was performed, as shown in FIG. 17. The results showed that for the stable cavitation, the coefficient of determination value $r^2$ of the unretracted clot ($r^2$=0.963) was higher than the retracted clot ($r^2$=0.906), which indicated that the stable cavitation played a more correlated role in the thrombolysis treatment of unretracted clot than the retracted clot.

Figure 18:
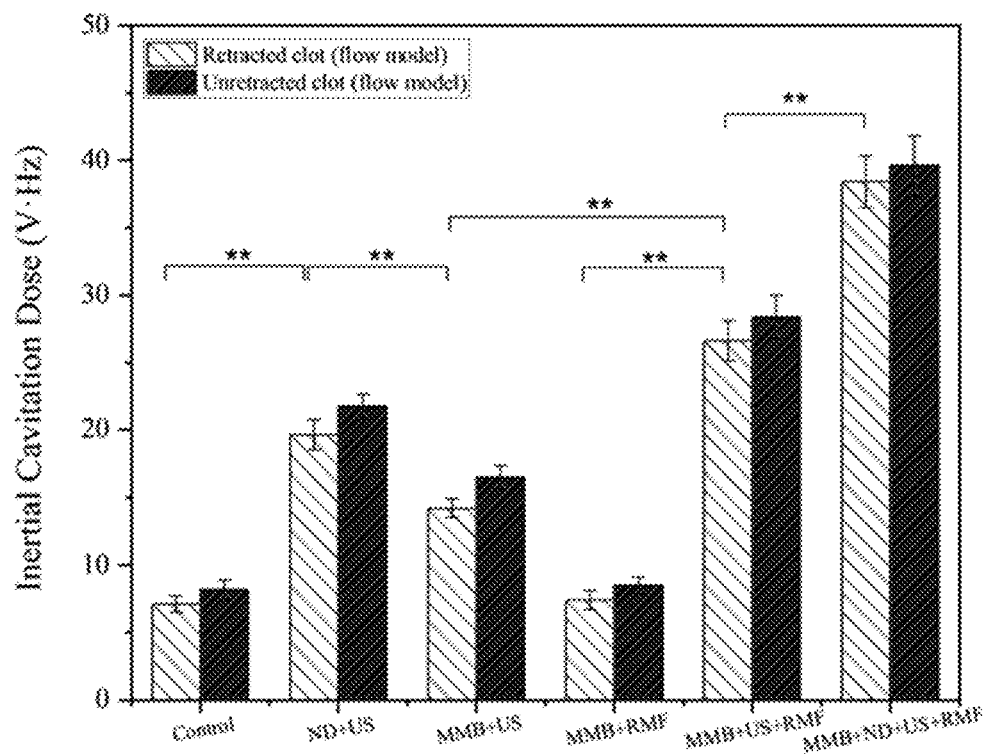
FIG. 18 is a bar graph illustrating the inertial cavitation dose (V·Hz) using different treatment methods for retracted and unretracted clot in a flow model. (Treatment time: 30 min, ultrasound parameters: 80 $V_{pp}$ input voltage, 4.7% duty cycle, f=850 kHz, magnetic field: B=20 mT, f=40 Hz) (*P<0.05, **P<0.01).

For the inertial cavitation dose, as shown in FIG. 18, there was no significant difference between the retracted clot and the unretracted clot among all the treatment groups. However, the results showed that there was a significant difference (p<0.01) between the ultrasound alone group ND+US (19.6±1.10 V·Hz), MMB+US (14.2±0.70 V·Hz), and the control group (7.10±0.60 V·Hz), which suggested that the inertia cavitation played a vital role in the MMBs and NDs mediated ultrasound thrombolysis treatment of retracted clot. Moreover, there was a significant difference (p<0.01) of the inertial cavitation dose between the MMB+US+RMF group (26.6±1.5 V·Hz) and MMB+US group (14.2±0.70 V·Hz) for the retracted clot treatment. This result revealed that the rotational magnetic field with magnetic microbubbles could significantly improve (>87.3%) in the inertial cavitation during the ultrasound thrombolysis treatment. Besides, the results showed that there was a significant higher (P<0.01) inertial cavitation dose of MMB+ND+US+RMF group (38.4±1.9 V·Hz) than the MMB+US+RMF group (26.6±1.5 V·Hz) for the retracted clot, which suggested that the combined of MMBs and NDs treatment method could induce more (>44.3%) inertial cavitation dose and therefore helped the thrombolysis of retracted clot.

Figure 19:
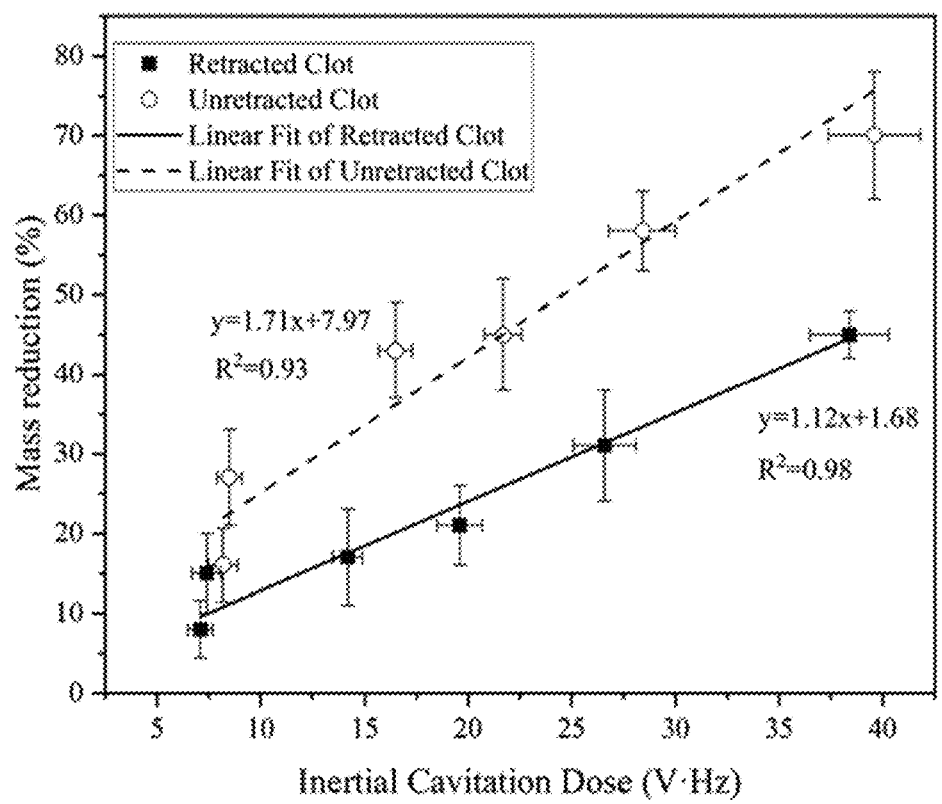
FIG. 19 is a graph of the correlation between clot mass reduction (%) and inertial cavitation dose (V·Hz) using different treatment methods for a retracted and unretracted clot in a flow model.

To clarify the relationship between inertial cavitation and mass reduction of the retracted clot and unretracted clot using different treatment methods, the linear regression analysis was performed, as shown in FIG. 19. The results showed that for the inertial cavitation, the coefficient of determination $r^2$ of the retracted clot ($r^2$=0.98) was higher than the unretracted clot ($r^2$=0.93), which revealed that the inertial cavitation played an essential role in the thrombolysis treatment of retracted clot.

tPA Mediated Thrombolysis with Different Treatment Methods

Figure 20:
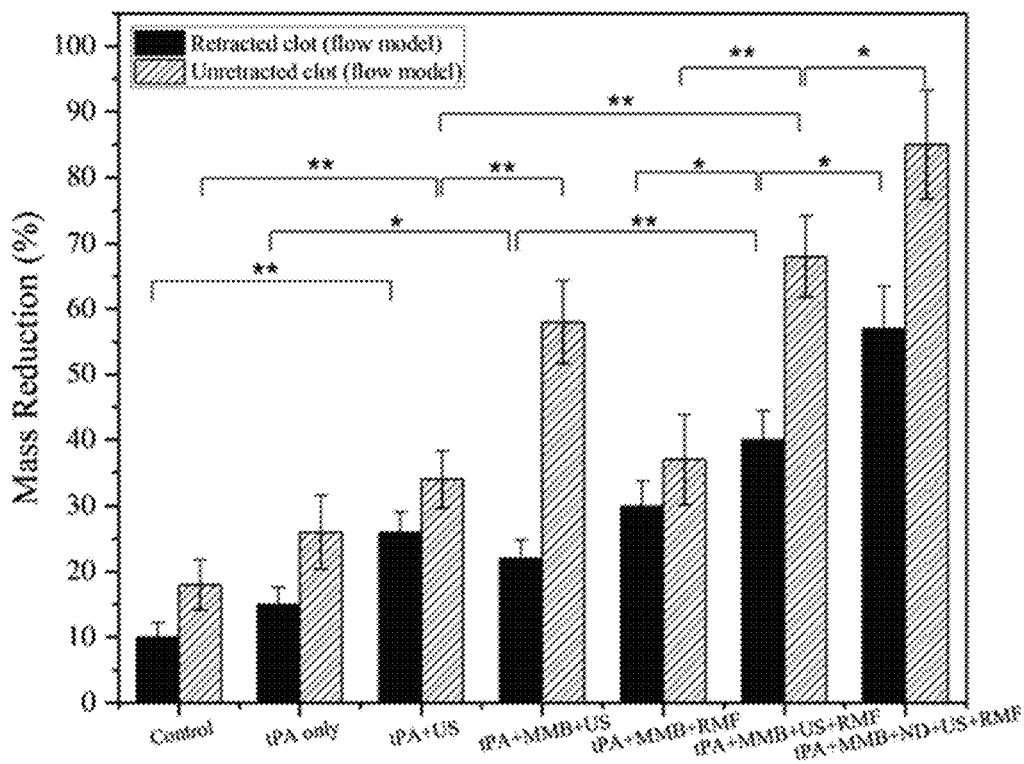
FIG. 20 is a graph illustrating in vitro test results using different treatment methods with tPA for retracted and unretracted clot in a flow model. (Treatment time: 30 min, ultrasound parameters: 80 $V_{pp}$ input voltage, 4.7% duty cycle, f=850 kHz, magnetic field: B=20 mT, f=40 Hz) (*P<0.05, **P<0.01).

To better understand the influence of tPA on the MMBs and NDs-mediated thrombolysis treatment in a flow model, different treatment methods with low dose tPA (0.75 μg/mL) were investigated. The same treatment parameters as 30 min treatment time, ultrasound input parameters (80 $V_{pp}$ input voltage, 4.7% duty cycle, f=850 kHz) and magnetic field parameters (magnetic field flux density B=20 mT, magnetic field frequency f=40 Hz) were used for each treatment. The control group was only injected with MMBs and NDs without any ultrasound and magnetic field exposure. As shown in FIG. 20, among all the treatment groups, the clot mass reduction rate of unretracted clots (average:

51.3±5.9%) was higher (>19.6%) than the retracted clot (average: 31.6±3.6%). Although the overall mass reduction rate of the unretracted clot was increased with the addition of tPA, there was no significant difference between tPA only group (15±2.6%) and the tPA+US group (26±3.1%) for the retracted clot. This result indicated that the tPA-mediated ultrasound thrombolysis treatment was more effective for unretracted clot lysis than retracted clot lysis.

However, there was a significant difference (P<0.05) between tPA only group (15±2.6%) and the tPA+MMB+US group (22±2.8%), which indicated that the magnetic microbubbles with ultrasound treatment could enhance (>46.7%) the tPA treatment outcome on the retracted clot. Moreover, the significant difference (p<0.01) between the tPA+MMB+US group (22±2.8%) and the tPA+MMB+US+RMF group (40±4.4%) showed that the rotational magnetic field could enhance (>81.8%) the thrombolytic effect of tPA mediated sonothrombolysis outcome. Besides, by combining nanodroplets with the tPA+MMB+US+RMF group, the mass reduction of the tPA+MMB+ND+US+RMF group for both unretracted clot (85±8.3%) and retracted clot (57±6.5%) was significantly enhanced (p<0.05). The above results suggested that the small size nanodroplets (~300 nm) could be used to further improve the tPA mediated ultrasound thrombolysis with magnetic microbubbles under the rotational magnetic field.

Thrombolysis with Different ND/MMB Concentration Ratio

To better understand the NDs and MMBs-mediated sonothrombolysis under the rotational magnetic field, the different NDs/MMBs concentration ratio was applied in this test. To be specific, the nanodroplets concentration was fixed at $10^8$/mL and the magnetic microbubbles concentration was varied as $10^6$/mL, $10^7$/mL, $10^8$/mL, $10^9$/mL, $10^{10}$/mL in order to obtain the mixed NDs/MMBs concentration ratio as 100:1, 10:1, 1:1, 1:10, 1:100. As shown in FIG. 21, the overall mass reduction of the unretracted clot and retracted clot was increased as the mixed NDs/MMBs concentration increase. This result indicated that the higher magnetic microbubbles concentration was mixed with nanodroplets; the higher mass reduction of the retracted clot could be achieved. Moreover, the results showed that there was a significant difference (p<0.01) between the control group (7±3%) and NDs/MMBs concentration ratio=1:1 group (27±5%) for the retracted clot; however, there was no significant difference among the NDs/MMBs concentration ratio=100:1, 10:1 and control group. This outcome suggested that when the NDs/MMBs concentration ratio was higher than 1:1, the mass reduction of the retracted clot could be significantly improved. However, there was no significant difference (P<0.05) between NDs/MMBs concentration ratio=1:10 group and 1:100 group for both unretracted clot and retracted clot, which indicated that a reasonable NDs/MMBs concentration ratio of around 1:10 provided better thrombolysis outcome.

Thrombolysis Treatment with Different Input Parameters

To clarify the thrombolysis effect of NDs, MMBs-mediated ultrasound, and rotational magnetic field combined treatment, various treatment cases were considered. As shown in FIG. 22A, different input voltages were used as the ultrasound input parameter. The result showed that the clot mass reduction of unretracted (average: 55.96±5.9%) was higher (>18.9%) than the retracted clot (average: 37.0±3.2%) when the input voltage increased. As shown in FIG. 22B, when the duty cycles increased from 0 to 4.7%, the clot mass reduction of the retracted clot (average: 30.5±3.15%) and the unretracted clot (average: 51.02±5.97%) was considerably increased by 192.9% and 156.8%, respectively. However, it showed a saturated trend (+5.47%) for retracted clot (average: 46.8±3.42%) when the duty cycles increased from 4.7% to 10% and a slightly increasing trend (+9.76%) for the unretracted clot (average: 74.3±5.60%). This result suggested that the reasonable duty cycle should be around ~4.7% for a better ND+MMB+US+RMF method treatment outcome.

The in vitro test results using combined NDs and MMBs with various ultrasound parameters had a similar tendency with the previously reported sonothrombolysis results obtained using microbubbles [42] and magnetic microbubbles [41]. The input voltages range from 0 to 120 $V_{pp}$ were selected according to our previous study [41]: the higher input voltages, the higher peak negative pressure (PNP), and the mechanical index (MI) can be obtained. However, due to the constraint of ultrasound transducer material limitation (45% of the AC depoling voltage for PZT-5A ceramics), 120 $V_{pp}$ was applied as an input voltage upper limit to maintain the transducer operating in an unfailing voltage range. Besides, the duty cycles range from 0 to 10% were used in this study, according to our previous study [41]. The 10% (5 ms burst duration and 425 cycle-burst) was applied as a duty cycle upper limit to maintain the transducer working in a safe state.

Next, the influence of the rotational magnetic field on nanodroplets was explored, along with magnetic microbubbles mediated ultrasound thrombolysis treatment using the same ultrasound input parameter (80 $V_{pp}$ input voltage, 4.7% duty cycle, 850 kHz). As shown in FIG. 23A, the higher the magnetic field flux density, the higher the clot mass reduction can be achieved for both unretracted clot (average: 58.24±4.46%) and retracted clot (average: 31.73±3.50%). This result was likely because, on the one hand, the higher magnetic flux density would generate a higher magnetic force applied on the magnetic microbubbles and increased the vortex-like microstreaming generated by oscillating magnetic nanoparticles to help the diffusion of nanodroplets to clot surface. On the other hand, the higher magnetic force applied to the magnetic microbubbles would increase the number of magnetic microbubbles against the flow, which increased the local clot region MMBs concentration. Due to the input power limitation of our customized Helmholtz coil, the magnetic flux density higher than 30 mT was not tested in this study. However, according to our previous study [41], the desired range of magnetic flux density for MMB+US+RMF thrombolysis was from 20 mT to 50 mT.

To further investigate the influence of rotational magnetic field frequency on the clot mass reduction rate, we performed the in vitro test with different magnetic field frequency from static, 10 Hz to 100 Hz. As shown in FIG. 23B, the mass reduction of both unretracted clot (average: 56.38±5.34%) and retracted clot (average: 32.24±2.70%) were increased significantly (unretracted clot: +83.8%, retracted clot: +188.5%) from 0 to 40 Hz and remained a decrease tendency (unretracted clot: −25.0%, retracted clot: −52.4%) from 40 Hz to 100 Hz. This outcome was likely because the higher frequency would increase the oscillation magnitude of the MMBs, the microstreaming induced by oscillating MMBs would promote the diffusion of NDs better seep into the clot surface. As a result, the nanodroplets and magnetic microbubbles were more likely to be activated by the ultrasound and therefore induce more cavitation effect and microstreaming underneath the clot surface.

Temperature Changes and Effects During the Treatment

To study the temperature changes during the thrombolysis treatment, a thermocouple, as shown in FIG. 14, was used to monitor the temperature of the clot region. As shown in FIG. 24, the control group was only injected with saline without the ultrasound stimulation and magnetic field applied. The MMB+RMF treatment group was treated with magnetic microbubbles in a rotational magnetic field (B=20 mT, f=40 Hz). The temperature increase (~0.7° C.) in MMB+RMF group (37.5±0.3° C.) was not significant compared to the control group (36.8±0.2° C.). This outcome indicated that the rotational magnetic field in the low-frequency range (f<40 Hz) was not inducing heating above the physiological temperature range. The MMB+US group (37.0±0.3° C.) and ND+US group (36.9±0.3° C.) both showed no significant temperature changes compared to the control group. Moreover, the temperature of MMB+US+RMF group (37.6±0.5° C.) was slightly increased compared to the control group but showed no significant difference compared to the MMB+RMF group, which indicated that the thrombolysis rate increase in the MMB+US+RMF group was not mainly attributed by the temperature changes and effects. Besides, the temperature changes of the ND+MMB+US+RMF group (38.0±0.6° C.) indicated that the combined treatment would induce a minor temperature rise (~1.2° C.), thus no effect on the clot lysis.

The Mechanism of Sonothrombolysis with ND and MMBs Under RMF

FIG. 25 is a schematic illustration of the mechanism of nanodroplets (NDs) and magnetic microbubbles (MMBs) mediated intravascular sonothrombolysis by using a catheter-tipped forward-looking ultrasound transducer under a rotational magnetic field (RMF). First, the magnetic microbubbles were delivered from the catheter drug delivery lumen and then were trapped and confined by the magnetic field around the clot region against blood flow. As a result, the total concentration of magnetic microbubbles that engaged at the clot surface for further ultrasound excitation was increased. Second, when the external rotational magnetic field was applied to the clot region, the magnetic microbubbles were forced to vibrate and oscillate at a certain frequency and amplitude according to the magnetic field frequency and flux density change, resulting in a pair of counter-rotating vortices around the magnetic microbubbles, inducing high shear flows, microjets and microstreaming, which would cause the mechanical injury to the fibrin network and create micro-channels on the surface of the clot. The clots with disrupted fibrin networks structure and surface were more likely to induce more magnetic microbubbles to diffuse underneath the clot surface. Third, the injected nanodroplets were pushed forward under ultrasound radiation force and microstreaming, resulting in the penetration of the clot surface through the micro-channels. Finally, the nanodroplets inside the micro-channels could be excited by ultrasound for cavitation effects and results in the expansion of micro-channels into the micro-holes, which allow more magnetic microbubbles to go through and create new micro-channels for further nanodroplets to deploy and cavitate as in a chain effect. Therefore, the combined mechanical force and cavitation bio-effects from the excitation of nanodroplets and magnetic microbubbles under the rotational magnetic field and ultrasound exposure could significantly enhance the thrombolysis outcomes.

Conclusions

This example demonstrated that the combination of nanodroplets with magnetic microbubbles could significantly enhance in vitro lysis of both unretracted clot and retracted clot in a flow model. First, we compared the thrombolysis effects of different treatment methods (ND+US, MMB+US, MMB+RMF, MMB+US+RMF, MMB+ND+US+RMF) on retracted and unretracted clot in a flow model. Second, we investigated the cavitation effect (stable cavitation, inertial cavitation) of different treatment methods and explored the correlation between clot mass reduction and cavitation doses. Third, we examined the influence of tPA effects on the various treatment method for the retracted and unretracted clot. Fourth, we studied the influence of the ND/MMB concentration ratio on thrombolysis rate to better understanding the combined therapy effect of ND and MMB. Finally, we explored the influence of various ultrasound parameters (input voltage, duty cycle), and magnetic field parameters (flux density, frequency) on the thrombolysis rate. This discovery provides innovative technology, which could employ the combined magnetic microbubbles and nanodroplets to improve the thrombolysis therapy of in vivo intravascular occlusions References for Example 2

[1] S. S. Virani, A. Alonso, E. J. Benjamin, M. S. Bittencourt, C. W. Callaway, A. P. Carson, A. M. Chamberlain, A. R. Chang, S. Cheng, F. N. Delling, *Circulation.* 2020, E139.

[2] M. NORDSTRÖM, B. LINDBLAD, D. BERGQVIST, T. KJELLSTRÖM, *J. Intern. Med.* 1992, 232, 155.

[3] C. M. Bulger, C. Jacobs, N. H. Patel, *Tech. Vasc. Interv. Radiol.* 2004, 7, 50.

[4] J. H. Rha, J. L. Saver, *Stroke* 2007, 38, 967.

[5] W. Hacke, M. Kaste, E. Bluhmki, M. Brozman, A. Dávalos, D. Guidetti, V. Larrue, K. R. Lees, Z. Medeghri, T. Machnig, D. Schneider, R. von Kummer, N. Wahlgren, D. Toni, *N. Engl. J. Med.* 2008, 359, 1317.

[6] C. Longstaff, K. Kolev, *J. Thromb. Haemost.* 2015, 13, S98.

[7] D. J. Miller, J. R. Simpson, B. Silver, *The Neurohospitalist* 2011, 1, 138.

[8] J. T. DeVries, C. J. White, M. C. Cunningham, S. R. Ramee, *Catheter. Cardiovasc. Interv.* 2008, 72, 705.

[9] C. A. Molina, A. D. Barreto, G. Tsivgoulis, P. Sierzenski, M. D. Malkoff, M. Rubiera, N. Gonzales, R. Mikulik, G. Pate, J. Ostrem, W. Singleton, G. Manvelian, E. C. Unger, J. C. Grotta, P. D. Schellinger, A. V. Alexandrov, *Ann. Neurol.* 2009, 66, 28.

[10] L. Goel, X. Jiang, *Sensors (Switzerland)* 2020, 20.

[11] S. Ricci, L. Dinia, M. Del Sette, P. Anzola, T. Mazzoli, S. Cenciarelli, C. Gandolfo, in *Cochrane Database Syst. Rev.* (Ed: S. Ricci), John Wiley & Sons, Ltd, Chichester, UK, 2012.

[12] O. A. Berkhemer, P. S. S. Fransen, D. Beumer, L. A. van den Berg, H. F. Lingsma, et al., *N. Engl. J. Med.* 2015, 372, 11.

[13] T. R. Porter, R. F. LeVeen, R. Fox, A. Kricsfeld, F. Xie, *Am. Heart J.* 1996, 132, 964.

[14] M. De Saint Victor, D. Carugo, L. C. Barnsley, J. Owen, C. C. Coussios, E. Stride, *Phys. Med. Biol.* 2017, 62, 7451.

[15] S. R. Sirsi, M. A. Borden, *Bubble Sci. Eng. Technol.* 2009, 1, 3.

[16] P. S. Sheeran, S. H. Luois, L. B. Mullin, T. O. Matsunaga, P. A. Dayton, *Biomaterials* 2012, 33, 3262.

[17] T. D. Martz, D. Bardin, P. S. Sheeran, A. P. Lee, P. A. Dayton, *Small* 2012, 8, 1876.

[18] R. J. Paproski, A. Forbrich, E. Huynh, J. Chen, J. D. Lewis, G. Zheng, R. J. Zemp, *Small* 2016, 12, 371.

[19] Y. Xu, Q. Lu, L. Sun, S. Feng, Y. Nie, X. Ning, M. Lu, *Small* 2020, 2002950.

[20] N. Rapoport, *Wiley Interdiscip. Rev. Nanomedicine Nanobiotechnology* 2012, 4, 492.

[21] L. C. Moyer, K. F. Timbie, P. S. Sheeran, R. J. Price, G. W. Miller, P. A. Dayton, *J. Ther. Ultrasound* 2015, 3, 1.

[22] S. Guo, X. Guo, X. Wang, D. Zhou, X. Du, M. Han, Y. Zong, M. Wan, *Ultrason. Sonochem.* 2019, 54, 183.

[23] Y. Zhong, Y. Zhang, J. Xu, J. Zhou, J. Liu, M. Ye, L. Zhang, B. Qiao, Z. G. Wang, H. T. Ran, D. Guo, ACS Nano 2019, 13, 3387.

[24] L. Ma, Y. Wang, S. Zhang, X. Qian, N. Xue, Z. Jiang, O. U. Akakuru, J. Li, Y. Xu, A. Wu, *Bioconjug. Chem.* 2020, 31, 369.

[25] J. Kim, R. M. DeRuiter, L. Goel, Z. Xu, X. Jiang, P. A. Dayton, *Ultrasound Med. Biol.* 2020, DOI 10.1016/j.ultrasmedbio.2020.07.008.

[26] N. Reznik, O. Shpak, E. C. Gelderblom, R. Williams, N. De Jong, M. Versluis, P. N. Burns, in *Ultrasonics, Elsevier,* 2013, pp. 1368-1376.

[27] S. T. Kang, Y. C. Lin, C. K. Yeh, *Ultrason. Sonochem.* 2014, 21, 1866.

[28] L. Duan, F. Yang, W. He, L. Song, F. Qiu, N. Xu, L. Xu, Y. Zhang, Z. Hua, N. Gu, *Adv. Funct. Mater.* 2016, 26, 8313.

[29] S. Wang, X. Guo, L. Ren, B. Wang, L. Hou, H. Zhou, Q. Gao, Y. Gao, L. Wang, *Ultrason. Sonochem.* 2020, 67, 105188.

[30] B. Zhang, X. Mo, F. Yu, Y. Ma, F. Yan, *Biomater. Sci.* 2020, 8, 3628.

[31] B. Chertok, R. Langer, *Theranostics* 2018, 8, 341.

[32] Z. Liu, T. Lammers, J. Ehling, S. Fokong, J. Bornemann, F. Kiessling, J. Gätjens, *Biomaterials* 2011, 32, 6155.

[33] J. Wu, H. Leong-Poi, J. Bin, L. Yang, Y. Liao, Y. Liu, J. Cai, J. Xie, Y. Liu, *Radiology* 2011, 260, 463.

[34] X. Cai, F. Yang, N. Gu, *Theranostics* 2012, 2, 103.

[35] L. C. Barnsley, M. D. Gray, E. Beguin, D. Carugo, E. Stride, *Adv. Mater. Technol.* 2018, 3, 1800081.

[36] M. D. Torno, M. D. Kaminski, Y. Xie, R. E. Meyers, C. J. Mertz, X. Liu, W. D. O'Brien, A. J. Rosengart, *Thromb. Res.* 2008, 121, 799.

[37] M. de Saint Victor, L. C. Barnsley, D. Carugo, J. Owen, C. C. Coussios, E. Stride, *Ultrasound Med. Biol.* 2019, 45, 1151.

[38] X. Chen, W. Wu, S. Wang, J. Zhong, N. M. Djama, G. Wei, Y. Lai, X. Si, S. Cao, W. Liao, Y. Liao, H. Li, J. Bin, *Thromb. Haemost.* 2019, 119, 1752.

[39] S. Wang, X. Guo, W. Xiu, Y. Liu, L. Ren, H. Xiao, F. Yang, Y. Gao, C. Xu, L. Wang, *Sci. Adv.* 2020, 6, eaaz8204.

[40] B. Zhang, X. Jiang, H. Wu, in 2018 *IEEE 13th Nanotechnol. Mater. Devices Conf. NMDC* 2018, 2019.

[41] B. Zhang, H. Kim, H. Wu, Y. Gao, X. Jiang, *Ultrasonics* 2019, 98, 62.

[42] J. Kim, B. D. Lindsey, W. Y. Chang, X. Dai, J. M. Stavas, P. A. Dayton, X. Jiang, *Sci. Rep.* 2017, 7, 1.

[43] Y. Gao, C. U. Chan, Q. Gu, X. Lin, W. Zhang, D. C. L. Yeo, A. M. Alsema, M. Arora, M. S. K. Chong, P. Shi, C. D. Ohl, C. Xu, *NPG Asia Mater.* 2016, 8, 260.

[44] L. Goel, H. Wu, H. Kim, B. Zhang, J. Kim, P. A. Dayton, Z. Xu, X. Jiang, *Ultrasound Med. Biol.* 2020, 46, 1698.

The invention claimed is:

1. A system comprising:
a plurality of magnetic microbubbles (MMBs) having a gas core and a layer of superparamagnetic nanoparticles around the gas core,
an ultrasound transducer effective to induce cavitation of the MMBs, wherein the ultrasound transducer is configured to generate an acoustic frequency of about 100 kHz to about 5 MHz, with an ultrasound duty cycle of about 0.5% to about 25%, and an input voltage of about $10V_{pp}$ to $250 V_{pp}$, and
a rotational magnetic field generator effective to accumulate MMBs in a target region and increase cavitation of the MMBs induced by the ultrasound transducer.

2. The system of claim 1, wherein the system is a sonothrombolysis system and the ultrasound transducer and the rotational magnetic field generator are adapted for placement near a target clot region of a patient, and further comprising a catheter configured for in vivo intravascular delivery of the MMBs to the target clot region of the patient, wherein the rotational magnetic field generator is effective to accumulate the MMBs in the target clot region and increase cavitation of the MMBs induced by the ultrasound transducer, such that cavitating MMBs are effective to induce partial or complete thrombolysis of a blood clot in the target clot region.

3. The system of claim 1, further comprising a plurality of nanodroplets (NDs).

4. The system of claim 3, wherein the system is a sonothrombolysis system and further comprises a catheter configured for in vivo intravascular delivery of the MMBs and the NDs to the target clot region of a patient.

5. The system of claim 3, wherein the NDs comprise:
a liquid core comprising one or more materials selected from the group consisting of: decafluorobutane (DFB) ($C_4F_{10}$), perfluorohexane (PFH) ($C_6F_{14}$), octafluoropropane (OFP) ($C_3F_8$), perfluoropentane (PFP) ($C_5F_{12}$), mesoporous silica nanoparticles (MSNs), magnetic nanodroplets (MNDs); and
an outer shell comprising one or more materials from the group consisting of: oil, polymers, surfactants, lipids, albumin, fluorosurfactant (Zonyl FSO), MSPC, DSPC, DPPC, DSPG, DSPE-PEG-2000, DSPE-PEG-5000, cholesterol, and 1,2-distearoyl-sn-glycero-3-phosphocholine,
wherein the NDs have an average diameter of about 150 nm-350 nm.

6. The system of claim 1, wherein the ultrasound transducer is selected from: an external HIFU transducer or an intravascular ultrasound (IVUS) transducer.

7. The system of claim 6, wherein the IVUS transducer is a forward-looking stacked IVUS transducer.

8. The system of claim 7, wherein the IVUS transducer comprises three or more stacked piezoelectric plates having alternating poling directions.

9. The system of claim 1, wherein the superparamagnetic nanoparticles in the MMBs comprise iron oxide superparamagnetic nanoparticles having an average size of 10-100 nm.

10. The system of claim 9, wherein the MMBs comprise a surface coating around the layer of superparamagnetic nanoparticles, the surface coating comprising a material selected from the group consisting of oils, polymers, surfactants, lipids, albumin, fluorosurfactant (Zonyl FSO), MSPC, DSPC, DPPC, DSPG, DSPE-PEG-2000, DSPE-PEG-5000, cholesterol, 1,2-distearoyl-sn-glycero-3-phosphocholine, and combinations thereof.

11. The system of claim 1, wherein the MMBs have an average diameter of about 1 μm to 100 μm.

12. The system of claim 1, wherein the rotational magnetic field generator includes a cylindrical permanent magnet coupled to a power source to rotate the magnet cylinder.

13. A method of treating blood clots, the method comprising:
administering magnetic microbubbles (MMBs) intravascularly to a patient in need of treatment for a blood clot in a blood vessel, the MMBs having a gas core and a layer of superparamagnetic nanoparticles around the gas core;
localizing the MMBs to a target clot region in the blood vessel by application of a magnetic field;
generating a rotational magnetic field in the target clot region to retain the MMBs in the target clot region and enhance ultrasound-induced movement of the MMBs; and
using an ultrasound transducer to acoustically activate the MMBs to generate movement of the MMBs within the blood vessel in the target clot region, wherein the ultrasound transducer generates an acoustic frequency of about 100 kHz to about 5 MHz, has an ultrasound duty cycle of about 0.5% to about 25%, and has an input voltage of about 10 $V_{pp}$ to 250 $V_{pp}$, and wherein movement of the MMBs induced by the ultrasound is increased under the rotational magnetic field, such that the movement of the MMBs is effective to reduce the blood clot in size.

14. The method of claim 13, wherein the ultrasound-induced movement is selected from the group consisting of: cavitation of the MMBs, microstreaming, and combinations thereof.

15. The method of claim 13, further comprising administering a plurality of nanodroplets (NDs) to the patient with the MMBs.

16. The method of claim 15, wherein the concentration of NDs administered is about $10^8$-$10^{12}$ NDs/mL.

17. The method of claim 15, wherein the concentration ratio of NDs/MMBs is from about 10:1 to 1:10.

18. The method of claim 13, wherein the ultrasound transducer is selected from the group consisting of: an external HIFU transducer and an intravascular ultrasound (IVUS) transducer.

19. The method of claim 13, wherein the MMBs are iron oxide MMBs having an average diameter of about 1 μm to 100 μm.

20. The method of claim 13, wherein acoustic activation of the MMBs under the rotational magnetic field increases a lysis rate of the blood clot as compared to acoustic activation of non-magnetic microbubbles with an ultrasound transducer alone.

21. The method of claim 13, wherein the concentration of MMBs administered is about $10^7$-$10^{12}$ MMBs/mL.

22. The method of claim 13, wherein the rotational magnetic field has a magnetic frequency of about 1 Hz to about 300 Hz and a magnetic flux density of about 1 mT to 80 mT.

23. A kit comprising:
an ultrasound transducer effective to induce in vivo cavitation of a plurality of magnetic microbubbles (MMBs) in a target region of a subject,
a portable, targeted rotational magnetic field generator effective to accumulate MMBs in a target region and increase cavitation of the MMBs induced by the ultrasound transducer, and
instructions for using the ultrasound transducer and portable, targeted rotational magnetic field generator with a composition of MMBs and optional NDs to treat a subject, wherein the instructions describe the use of the ultrasound transducer to generate an acoustic frequency of about 100 kHz to about 5 MHz, with an ultrasound duty cycle of about 0.5% to about 25%, and an input voltage of about 10 $V_{pp}$ to 250 $V_{pp}$.

24. The kit of claim 23, wherein the kit further includes nanodroplets (NDs), and wherein the ultrasound transducer is an intravascular ultrasound (IVUS) transducer that is integrated into a catheter, the catheter further comprising an integrated delivery lumen for administration of a composition comprising MMBs to the target region of the subject, and wherein the instructions describe the use of the IVUS transducer, the portable, targeted rotational magnetic field generator and composition of MMBs and NDs for intravascular sonothrombolysis of a blood clot in a subject.

* * * * *